(12) United States Patent
Fischer et al.

(10) Patent No.: US 10,596,250 B2
(45) Date of Patent: *Mar. 24, 2020

(54) METHODS OF TREATING AND PREVENTING INFLUENZA INFECTIONS

(71) Applicant: Longhorn Vaccines and Diagnostics, LLC, Bethesda, MD (US)

(72) Inventors: Gerald W. Fischer, Bethesda, MD (US); Luke T. Daum, San Antonio, TX (US)

(73) Assignee: Longhorn Vaccines and Diagnostics, LLC, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/983,215

(22) Filed: May 18, 2018

(65) Prior Publication Data

US 2018/0250383 A1 Sep. 6, 2018

Related U.S. Application Data

(63) Continuation of application No. 15/447,972, filed on Mar. 2, 2017, now Pat. No. 10,004,799, which is a continuation-in-part of application No. 15/205,476, filed on Jul. 8, 2016, now Pat. No. 9,777,045, which is a continuation-in-part of application No. 14/473,605, filed on Aug. 29, 2014, now Pat. No. 9,388,220, which is a continuation of application No. 12/199,729, filed on Aug. 27, 2008, now Pat. No. 8,821,885, said application No. 15/447,972 is a continuation of application No. 13/750,771, filed on Jan. 25, 2013, now Pat. No. 9,598,462.

(60) Provisional application No. 61/591,113, filed on Jan. 26, 2012, provisional application No. 60/968,145, filed on Aug. 27, 2007.

(51) Int. Cl.
| | | |
|---|---|---|
| A61K 39/145 | (2006.01) |
| C07K 14/35 | (2006.01) |
| C07K 14/005 | (2006.01) |
| C07K 16/12 | (2006.01) |
| C07K 16/10 | (2006.01) |
| A61K 39/04 | (2006.01) |
| C12N 7/00 | (2006.01) |
| A61K 39/12 | (2006.01) |
| C07K 14/33 | (2006.01) |
| A61K 39/00 | (2006.01) |

(52) U.S. Cl.
CPC .......... *A61K 39/145* (2013.01); *A61K 39/04* (2013.01); *A61K 39/12* (2013.01); *C07K 14/005* (2013.01); *C07K 14/33* (2013.01); *C07K 14/35* (2013.01); *C07K 16/1018* (2013.01); *C07K 16/1289* (2013.01); *C12N 7/00* (2013.01); *A61K 2039/525* (2013.01); *A61K 2039/5252* (2013.01); *A61K 2039/5254* (2013.01); *A61K 2039/53* (2013.01); *A61K 2039/543* (2013.01); *A61K 2039/545* (2013.01); *A61K 2039/55566* (2013.01); *A61K 2039/575* (2013.01); *A61K 2039/6037* (2013.01); *A61K 2039/6043* (2013.01); *A61K 2039/6068* (2013.01); *A61K 2039/70* (2013.01); *C07K 2319/40* (2013.01); *C07K 2319/42* (2013.01); *C12N 2760/16122* (2013.01); *C12N 2760/16134* (2013.01); *C12N 2760/16161* (2013.01)

(58) Field of Classification Search
CPC ............... C12N 7/00; C12N 15/11; C12N 2760/16122; C12N 2310/344; C12N 2760/16022; C12N 2760/16161; C12N 2760/16134; A61K 39/12; A61K 39/145; A61K 2039/70; A61K 39/04; A61K 2039/525; A61K 2039/5252; A61K 2039/5254; A61K 2039/543; A61K 2039/545; A61K 2039/55566; A61K 2039/6037; A61K 2039/6043; A61K 2039/6068; A61K 2039/575; A61K 2039/53; C07K 14/005; C07K 2317/34; C07K 2317/31; C07K 2317/33; C07K 7/06; C07K 7/08; C07K 14/33; C07K 14/35; C07K 16/1289; C07K 16/1018; C07K 2319/40; C07K 2319/42

See application file for complete search history.

(56) References Cited

U.S. PATENT DOCUMENTS

| | | | |
|---|---|---|---|
| 1,307,416 | A | 6/1919 | Pine |
| 2,697,373 | A | 12/1954 | Siekmann et al. |
| 4,116,777 | A | 9/1978 | Takatsy et al. |
| 4,196,265 | A | 4/1980 | Koprowski et al. |

(Continued)

FOREIGN PATENT DOCUMENTS

| | | |
|---|---|---|
| EP | 0313224 | 4/1989 |
| EP | 0621339 | 10/1994 |

(Continued)

OTHER PUBLICATIONS

IN Exam Report for Application No. 1354/KOLNP/2014, dated Nov. 1, 2018.

(Continued)

*Primary Examiner* — Rachel B Gill
(74) *Attorney, Agent, or Firm* — Remenick PLLC

(57) ABSTRACT

The invention relates to composite antigens comprising a peptide with contiguous amino acid sequence derived from a plurality of antigenic epitopes of one or more pathogens that induces an immune response in a mammal that is protective against infection by the one or more pathogens. In addition, the invention relates to vaccines comprising composite antigens and to method for treating and preventing an infection.

30 Claims, 16 Drawing Sheets

Specification includes a Sequence Listing.

(56) References Cited

U.S. PATENT DOCUMENTS

| | | | |
|---|---|---|---|
| 4,235,244 A | 11/1980 | Abele et al. | |
| 4,315,073 A | 2/1982 | Brown et al. | |
| 4,355,102 A | 10/1982 | Quash | |
| 4,356,170 A | 10/1982 | Jennings et al. | |
| 4,371,091 A | 2/1983 | Gelina | |
| 4,372,945 A | 2/1983 | Likhite | |
| 4,474,757 A | 10/1984 | Arnon et al. | |
| 4,529,702 A | 7/1985 | Bryan | |
| 4,554,101 A | 11/1985 | Hopp | |
| 4,559,231 A | 12/1985 | Bjerre et al. | |
| 4,578,770 A | 3/1986 | Mitani | |
| 4,588,680 A | 5/1986 | Bucher et al. | |
| 4,596,792 A | 6/1986 | Vyas | |
| 4,599,230 A | 7/1986 | Milich et al. | |
| 4,599,231 A | 7/1986 | Milich et al. | |
| 4,601,903 A | 7/1986 | Frasch | |
| 4,608,251 A | 8/1986 | Mia | |
| 4,634,664 A | 1/1987 | Oestberg | |
| 4,634,666 A | 1/1987 | Engleman et al. | |
| 4,668,476 A | 5/1987 | Bridgham et al. | |
| 4,683,195 A | 7/1987 | Mullis et al. | |
| 4,683,202 A | 7/1987 | Mullis | |
| 4,707,450 A | 11/1987 | Nason | |
| 4,744,982 A | 5/1988 | Hunter et al. | |
| 4,746,490 A | 5/1988 | Saneii | |
| 4,749,490 A | 6/1988 | Smyth et al. | |
| 4,800,159 A | 1/1989 | Mullis et al. | |
| 4,803,998 A | 2/1989 | Kezes et al. | |
| 4,816,513 A | 3/1989 | Bridgham et al. | |
| 4,883,750 A | 11/1989 | Whiteley et al. | |
| 4,954,449 A | 9/1990 | Hunter et al. | |
| 4,981,782 A | 1/1991 | Judd et al. | |
| 4,996,143 A | 2/1991 | Heller et al. | |
| 5,091,316 A | 2/1992 | Monthony et al. | |
| 5,108,927 A | 4/1992 | Dorn | |
| 5,136,019 A | 8/1992 | Judd et al. | |
| 5,145,684 A | 9/1992 | Liversidge et al. | |
| 5,149,653 A | 9/1992 | Roser | |
| 5,163,441 A | 11/1992 | Monthony et al. | |
| 5,168,039 A | 12/1992 | Crawford et al. | |
| 5,182,109 A | 1/1993 | Tamura et al. | |
| 5,186,898 A | 2/1993 | Bridgham et al. | |
| 5,187,060 A | 2/1993 | Cerutti et al. | |
| 5,234,809 A | 8/1993 | Boom et al. | |
| 5,243,030 A | 9/1993 | Judd et al. | |
| 5,252,458 A | 10/1993 | Liav et al. | |
| 5,290,686 A | 3/1994 | Kendal et al. | |
| 5,316,910 A | 5/1994 | Rota et al. | |
| 5,399,363 A | 3/1995 | Liversidge et al. | |
| 5,482,856 A | 1/1996 | Fell, Jr. et al. | |
| 5,503,841 A | 4/1996 | Doyle et al. | |
| 5,543,158 A | 8/1996 | Gref et al. | |
| 5,545,555 A | 8/1996 | Racioppi et al. | |
| 5,552,157 A | 9/1996 | Yagi et al. | |
| 5,565,213 A | 10/1996 | Nakamori et al. | |
| 5,565,322 A | 10/1996 | Heller | |
| 5,567,434 A | 10/1996 | Szoka, Jr. | |
| 5,571,511 A | 11/1996 | Fischer | |
| 5,589,174 A | 12/1996 | Okuno et al. | |
| 5,591,823 A | 1/1997 | Hung | C07K 14/005 424/184.1 |
| 5,612,037 A | 3/1997 | Huebner | A61K 39/145 424/193.1 |
| 5,627,071 A | 5/1997 | Triva | |
| 5,631,350 A | 5/1997 | Okuno et al. | |
| 5,641,515 A | 6/1997 | Ramtoola | |
| 5,656,016 A | 8/1997 | Ogden | |
| 5,663,055 A | 9/1997 | Turner et al. | |
| 5,679,356 A | 10/1997 | Bonnem et al. | |
| 5,691,299 A | 11/1997 | Fabry | |
| 5,697,899 A | 12/1997 | Hillman et al. | |
| 5,702,944 A | 12/1997 | Racioppi et al. | |
| 5,719,020 A | 2/1998 | Liav et al. | |
| 5,736,333 A | 4/1998 | Livak et al. | |
| 5,738,868 A | 4/1998 | Shinkarenko | |
| 5,741,516 A | 4/1998 | Webb et al. | |
| 5,766,841 A | 6/1998 | Liav et al. | |
| 5,770,219 A | 6/1998 | Chiang et al. | |
| 5,779,708 A | 7/1998 | Wu | |
| 5,783,208 A | 7/1998 | Venkateshwaran et al. | |
| 5,785,975 A | 7/1998 | Parikh | |
| 5,795,582 A | 8/1998 | Wright | |
| 5,795,587 A | 8/1998 | Gao et al. | |
| 5,797,898 A | 8/1998 | Santini, Jr. et al. | |
| 5,800,810 A | 9/1998 | Doyle et al. | |
| 5,849,489 A | 12/1998 | Heller | |
| 5,891,624 A | 4/1999 | Huang | |
| 5,945,515 A | 8/1999 | Chomczynski | |
| 5,955,074 A | 9/1999 | Fischer | |
| 5,958,379 A | 9/1999 | Regenold et al. | |
| 6,015,664 A | 1/2000 | Henrickson et al. | |
| 6,033,673 A | 3/2000 | Clements | |
| 6,060,068 A | 5/2000 | Doyle et al. | |
| 6,136,585 A | 10/2000 | Ball et al. | 435/236 |
| 6,162,603 A | 12/2000 | Heller | |
| 6,168,915 B1 | 1/2001 | Scholl et al. | |
| 6,242,582 B1 | 6/2001 | Reece et al. | |
| 6,280,928 B1 | 8/2001 | Scholl et al. | |
| 6,306,404 B1 | 10/2001 | LaPosta et al. | |
| 6,306,582 B1 | 10/2001 | Scholl et al. | |
| 6,312,395 B1 | 11/2001 | Tripp et al. | |
| 6,376,172 B1 | 4/2002 | Scholl et al. | |
| 6,406,842 B2 | 6/2002 | Scholl et al. | |
| 6,440,423 B1 | 8/2002 | Clements et al. | |
| 6,451,325 B1 | 9/2002 | Van Nest et al. | |
| 6,458,577 B1 | 10/2002 | Huang | |
| 6,495,316 B1 | 12/2002 | Scholl et al. | |
| 6,500,432 B1 | 12/2002 | Dalemans et al. | |
| 6,503,745 B1 | 1/2003 | Chand et al. | |
| 6,534,065 B1 | 3/2003 | Makin et al. | |
| 6,572,866 B1 | 6/2003 | Torcia | |
| 6,573,080 B2 | 6/2003 | Scholl et al. | |
| 6,602,510 B1 | 8/2003 | Fikes et al. | |
| 6,603,908 B2 | 8/2003 | Dallas et al. | |
| 6,603,998 B1 | 8/2003 | King et al. | |
| 6,610,293 B1 | 8/2003 | Fischer et al. | |
| 6,610,474 B1 | 8/2003 | Huang | |
| 6,627,396 B1 | 9/2003 | Swanson et al. | |
| 6,632,432 B1 | 10/2003 | Fischer | |
| 6,680,308 B1 | 1/2004 | Hassan | |
| 6,689,363 B1 | 2/2004 | Sette et al. | 424/189.1 |
| 6,713,068 B1 | 3/2004 | Audonnet et al. | |
| 6,720,409 B2 | 4/2004 | Okuno et al. | |
| 6,734,292 B1 | 5/2004 | Omura et al. | |
| 6,759,241 B1 | 7/2004 | Hone et al. | |
| 6,780,421 B1 | 8/2004 | Haensler et al. | |
| 6,793,928 B1 | 9/2004 | van Scharrenburg et al. | |
| 6,811,971 B2 | 11/2004 | Klepp et al. | |
| 6,855,321 B1 | 2/2005 | Rappuoli et al. | 424/192.1 |
| 6,875,600 B2 | 4/2005 | Scholl et al. | |
| 6,881,835 B2 | 4/2005 | Bai et al. | |
| 6,893,814 B2 | 5/2005 | Swanson et al. | |
| 6,939,543 B2 | 9/2005 | Fischer et al. | |
| 6,946,291 B2 | 9/2005 | Scholl et al. | |
| 7,090,853 B2 | 8/2006 | Kapp et al. | |
| 7,122,640 B2 | 10/2006 | Gjerde et al. | |
| 7,223,409 B2 | 5/2007 | Nagata et al. | |
| 7,279,162 B1 | 10/2007 | Fischer | |
| 7,311,671 B2 | 12/2007 | Jung et al. | |
| 7,351,413 B2 | 4/2008 | Page et al. | |
| 7,357,936 B1 | 4/2008 | Garcon | |
| 7,361,352 B2 | 4/2008 | Birkett et al. | |
| 7,494,771 B2 | 2/2009 | Picard et al. | |
| 7,541,194 B2 | 6/2009 | Mink et al. | |
| 7,648,681 B2 | 1/2010 | Meyer et al. | |
| 7,718,402 B2 | 5/2010 | Gayral et al. | |
| 7,767,804 B2 | 8/2010 | Bair, Jr. et al. | |
| 7,794,001 B2 | 9/2010 | Blackwell et al. | |
| 8,080,645 B2 | 12/2011 | Fischer et al. | |
| 8,084,443 B2 | 12/2011 | Fischer et al. | |
| 8,097,419 B2 | 1/2012 | Fischer et al. | |
| 8,293,467 B2 | 10/2012 | Fischer et al. | |
| 2001/0021501 A1 | 9/2001 | Scholl et al. | |
| 2001/0034022 A1 | 10/2001 | Scholl et al. | |

(56) References Cited

U.S. PATENT DOCUMENTS

| | | | |
|---|---|---|---|
| 2001/0036628 A1 | 11/2001 | Scholl et al. | |
| 2002/0054882 A1 | 5/2002 | Okuno et al. | |
| 2002/0055094 A1 | 5/2002 | Reece et al. | |
| 2002/0081567 A1 | 6/2002 | Henrickson et al. | |
| 2002/0082395 A1 | 6/2002 | Fischer et al. | |
| 2002/0169140 A1 | 11/2002 | Prendergast | |
| 2003/0054337 A1 | 3/2003 | Birkett | 435/5 |
| 2003/0119209 A1 | 6/2003 | Kaylor et al. | |
| 2003/0143566 A1 | 7/2003 | Helftenbein | |
| 2003/0203357 A1 | 10/2003 | Huang | |
| 2003/0215796 A1 | 11/2003 | Scholl et al. | |
| 2003/0219442 A1 | 11/2003 | Mikayama et al. | |
| 2004/0009126 A1 | 1/2004 | Pilkiewicz et al. | |
| 2004/0009185 A1 | 1/2004 | Emtage | A61K 39/0011 424/185.1 |
| 2004/0013673 A1 | 1/2004 | Fischer et al. | |
| 2004/0071757 A1 | 4/2004 | Rolf | |
| 2004/0082549 A1 | 4/2004 | Jomaa | |
| 2004/0086849 A1 | 5/2004 | Shimasaki et al. | |
| 2004/0101869 A1 | 5/2004 | Berg et al. | |
| 2004/0126789 A1 | 7/2004 | Park et al. | |
| 2004/0142319 A1 | 7/2004 | Yu et al. | |
| 2004/0170965 A1 | 9/2004 | Scholl et al. | |
| 2004/0214272 A1 | 10/2004 | La Rosa et al. | 435/69.1 |
| 2004/0223976 A1 | 11/2004 | Bianchi et al. | 424/186.1 |
| 2005/0009008 A1 | 1/2005 | Robinson et al. | |
| 2005/0042229 A1 | 2/2005 | Yang et al. | |
| 2005/0090009 A1 | 4/2005 | Cormier et al. | |
| 2005/0106178 A1 | 5/2005 | O'Hagan | A61K 39/145 424/209.1 |
| 2005/0112656 A1 | 5/2005 | Iwaki | |
| 2005/0169941 A1 | 8/2005 | Lees | |
| 2005/0170334 A1 | 8/2005 | Mikayama et al. | |
| 2005/0181357 A1 | 8/2005 | Peiris et al. | |
| 2005/0187213 A1 | 8/2005 | Lang et al. | |
| 2005/0227269 A1 | 10/2005 | Lloyd, Jr. et al. | |
| 2006/0002939 A1 | 1/2006 | Fischer et al. | |
| 2006/0014185 A1 | 1/2006 | Ollikka et al. | |
| 2006/0105468 A1 | 5/2006 | Winkler et al. | |
| 2006/0121468 A1 | 6/2006 | Allnutt et al. | 435/6 |
| 2006/0134648 A1 | 6/2006 | Chou et al. | |
| 2006/0217338 A1 | 9/2006 | Lu et al. | 514/44 |
| 2006/0286557 A1 | 12/2006 | Basehore et al. | |
| 2007/0078025 A1 | 4/2007 | Pepe | |
| 2007/0102946 A1 | 5/2007 | Blackwell et al. | |
| 2007/0172835 A1 | 7/2007 | McBride et al. | |
| 2007/0196388 A1 | 8/2007 | Dowling et al. | |
| 2007/0202497 A1 | 8/2007 | Renuart et al. | |
| 2007/0202511 A1 | 8/2007 | Chen et al. | |
| 2007/0286871 A1 | 12/2007 | Hickle et al. | 424/202.1 |
| 2008/0032921 A1 | 2/2008 | Alexander et al. | 514/2 |
| 2008/0050737 A1 | 2/2008 | Arieli et al. | |
| 2008/0069821 A1 | 3/2008 | Yang et al. | |
| 2008/0074521 A1 | 3/2008 | Olsen | |
| 2008/0075708 A1 | 3/2008 | Yu et al. | |
| 2008/0078499 A1 | 4/2008 | Fenney | |
| 2008/0107665 A1 | 5/2008 | Suckow et al. | |
| 2008/0107687 A1 | 5/2008 | Poulet | |
| 2008/0118531 A1 | 5/2008 | Hoffmann et al. | |
| 2008/0139789 A1 | 6/2008 | Fischer | |
| 2008/0145373 A1 | 6/2008 | Arumugham et al. | |
| 2008/0181914 A1 | 7/2008 | Eichhorn | |
| 2008/0260763 A1 | 10/2008 | Feigner et al. | 424/186.1 |
| 2009/0081202 A1 | 3/2009 | Fiscehr | |
| 2009/0092582 A1 | 4/2009 | Bogin et al. | 424/85.5 |
| 2009/0098527 A1 | 4/2009 | Fischer et al. | |
| 2009/0233309 A1 | 9/2009 | Fischer et al. | |
| 2009/0304730 A1 | 12/2009 | Arnon | A61K 39/145 424/186.1 |
| 2009/0312285 A1 | 12/2009 | Fischer et al. | |
| 2010/0009343 A1 | 1/2010 | Fischer et al. | |
| 2010/0043546 A1 | 2/2010 | Kandori et al. | |
| 2010/0055672 A1 | 3/2010 | Saghbini | |
| 2010/0135955 A1 | 6/2010 | Moyle | A61K 39/145 424/85.2 |
| 2010/0151477 A1 | 6/2010 | Cawthon | |
| 2010/0221822 A1 | 9/2010 | Fischer et al. | |
| 2010/0311739 A1 | 12/2010 | Gunaratnam et al. | |
| 2011/0117128 A1 | 5/2011 | Powell et al. | 424/210.1 |
| 2011/0159497 A1 | 6/2011 | Lee et al. | |
| 2011/0182974 A1 | 7/2011 | Ben-Yedidia et al. | 424/450 |
| 2011/0281754 A1 | 11/2011 | Fischer et al. | |
| 2012/0014972 A1 | 1/2012 | Hodges et al. | 424/159.1 |
| 2012/0088231 A1 | 4/2012 | Fischer et al. | |
| 2012/0100529 A1 | 4/2012 | Fischer et al. | |
| 2012/0107799 A1 | 5/2012 | Daum | |
| 2012/0115126 A1 | 5/2012 | Fischer et al. | |
| 2012/0177701 A1 | 7/2012 | Ilyinskii et al. | 424/400 |
| 2012/0244527 A1 | 9/2012 | Trinh et al. | |
| 2013/0039884 A1 | 2/2013 | Bogin et al. | 424/85.2 |
| 2013/0195909 A1 | 8/2013 | Fischer et al. | 424/192.1 |

FOREIGN PATENT DOCUMENTS

| | | | |
|---|---|---|---|
| EP | 0675199 | 10/1995 | |
| EP | 0726316 | 8/1996 | |
| EP | 1081496 | 3/2001 | |
| RU | 2150281 | 6/2000 | |
| WO | WO 91/02740 | 3/1991 | |
| WO | WO1992016619 | 1/1992 | |
| WO | WO1992003454 | 3/1992 | |
| WO | WO1992003454 | 5/1992 | |
| WO | WO1992016619 | 10/1992 | |
| WO | WO1994009035 | 4/1994 | |
| WO | WO1994017106 | 4/1994 | |
| WO | WO1994017106 | 8/1994 | |
| WO | WO 1995/08348 | 3/1995 | |
| WO | WO1997005248 | 2/1997 | |
| WO | WO01/16163 A2 | 3/2001 | |
| WO | WO2003026567 | 3/2003 | |
| WO | WO2003026567 | 4/2003 | |
| WO | WO 2003/053462 | 7/2003 | |
| WO | WO2003053462 | 7/2003 | |
| WO | WO03/095646 | 11/2003 | |
| WO | WO2004/002451 A2 | 1/2004 | |
| WO | WO2004002451 | 1/2004 | |
| WO | WO2004004658 | 1/2004 | |
| WO | WO 2004/043407 | 5/2004 | |
| WO | WO2004043407 | 5/2004 | |
| WO | WO2004055205 | 7/2004 | |
| WO | WO2004072270 | 8/2004 | |
| WO | WO2004084876 | 10/2004 | |
| WO | WO2005010186 | 2/2005 | |
| WO | WO2005/042784 | 5/2005 | |
| WO | WO2005075642 | 8/2005 | |
| WO | WO2005085274 | 9/2005 | |
| WO | WO2006/041933 A2 | 4/2006 | |
| WO | WO2006041933 | 4/2006 | |
| WO | WO 2006/138444 | 12/2006 | |
| WO | WO2006138444 | 12/2006 | |
| WO | WO2007051036 | 3/2007 | |
| WO | WO 2007/051036 | 5/2007 | |
| WO | WO 2007/056266 | 5/2007 | |
| WO | WO2007051036 | 5/2007 | |
| WO | WO2007056266 | 5/2007 | |
| WO | WO 2007/091030 | 8/2007 | |
| WO | WO2007091030 | 8/2007 | |
| WO | WO2007133682 | 11/2007 | |
| WO | WO-2008054540 A2 | 5/2008 | A61K 39/145 |
| WO | WO2008079463 | 7/2008 | |
| WO | WO 2009/016639 | 2/2009 | |
| WO | WO2009/016639 | 2/2009 | |
| WO | WO2009/029686 | 3/2009 | |
| WO | WO 2009/029686 | 3/2009 | |
| WO | WO2009085355 | 7/2009 | |
| WO | WO1997005248 | 9/2009 | |
| WO | WO 2010/056796 | 5/2010 | |

OTHER PUBLICATIONS

Clementi Et Al. "A Human Monoclonal Antibody with Neutralizing Activity against Highly Divergent Influenza Subtypes", Plos One, vol. 6, No. 12, pp. 1-10, XP008150246 Dec. 5, 2011.

(56) References Cited

OTHER PUBLICATIONS

CA Exam Report for Application No. 2,863,083 dated Dec. 3, 2018.
Long NT, Hoa DM, Komadina N. Hemagglutinin [Influenza A virus (A/Muscovy Duck/VietNam/NCVD02/2005(H5N1))]. GenBank: ABQ09850. Dep. May 7, 2007.
Guo Y, Wang MG, Kawaoka Y, Gorman OT, Ito T, Webster RG. Hemagglutinin. UniProtKB/Swiss-Prot: Q03909. Dep. Mar. 1, 2004.
EP Exam Report for Application No. 13741334.0-1412, dated Jun. 13, 2017.
Austalian Exam Report for Application No. 2012239385, dated Oct. 9, 2013.
Austalian Exam Report for Application No. 2012211365, dated Oct. 9, 2013.
Max, et al Reliability of PCR-based detection of occult tumour cells: lessons from real-time RT-PCR.
EP Search Report for Application No. 13175959, dated Nov. 18, 2013.
PCT Search and Patentability Report for PCT/US2013/077038, dated Mar. 10, 2014.
CA Office Action for CA Application No. 2701168, dated Mar. 4, 2014.
EP Search Report and Opinion for Application No. 13741334, dated Jul. 20, 2015.
Giles, et al., "Antibody Breadth and Protective Efficacy Are Increased by Vaccination with Computationally Optimized Hemagglutinin but not with Polyvalent Hemagglutinin-Based H5N1 Virus-Like Particle Vaccines," Clinical and Vaccine Immunology, vol. 19, No. 2, Feb. 1, 2012, pp. 128-139.
Shi et al., A Complete Analysis of HA and NA Genes of Influenza A Viruses, 2010, PLoS One, vol. 5. No. 12, e14454, pp. 1-15.
FluZone package insert, Seasonal influenza vaccine, 2009.
PCT Patentability Report for PCT/US2013/023269, dated Jul. 29, 2014.
Lin Y. Haemagglutinin, partial [Influenza A virus (A/Denmark/39/2000(H1N1))]. GenBank Acc. No. CAD29940.1. Sub. Apr. 15, 2005.
Garten R, Smith C, Barnes J, Myrick A, Klimov A, Cox N. hemagglutinin [Influenza A virus (A/Wisconsin/14/2009(H1N1))]. GenBank Acc. No. ACV72381.1. Dep. Sep. 19, 2009.
"Development of an Internal Positive Control for Rapid Diagnosis of Avian Influenza, etc.", A.Das, et al., Journal of Clinical Microbiology, Sep. 2006, vol. 44, No. 9, pp. 3065-3073.
De Moreau de Gerbehaye, A.I. et al., "Stable Hepatitis C Virus RNA Detection by RT-PCR During Four Days Storage," BioMed Central, BMC Infectious Diseases, 2:22 (2002).
"Evaluation of PCR Testing of Ethanol-Fixed Nasal Swab Specimens, etc." A.Krafft, et al., Journal of Clinical Microbiology, Apr. 2005, vol. 43, No. 4, pp. 1768-1775.
"Abstracts—27th Annual Meeting for the European Society for Paediatric Infectious Disease, Brussels, Belgium, Jun. 9-13, 2009," The Ped. Infect. Dis. J., 28(6):e1, e75, e229 (Jun. 2009).
"AgPath-ID One-Step RT-PCR Kit," Applied Biosystems, available at http://www.abion.com/techlib/prot/bp_1005.pdf (last visited Aug. 24, 2009).
Lin, B., et al., "Broad-Spectrum Respiratory Tract Pathogen Identification Using Resequencing DNA Microarrays." Genome Res., 16:527-35 (2006).
Buck et al. BioTechniques vol. 27, pp. 528-536, Sep. 1999.
Wolff, C. et al, "Single-Tube Nested PCR With Room-Temperature-Stable Reagents," Cold Spring Harbor Laboratory Press, PCR Methods and Appl., 4:376-79 (1995).
Schultz, C.L., et al., "A Lysis, Storage, and Transportation Buffer for Long-Term, Room-Temperature Preservation of Human Clinical Lymphoid Tissue Samples Yielding High Molecular Weight Genomic DNA Suitable for Molecular Diagnosis," Am. J. Clin. Pathol., 111(6):748-52 (1999).
Characterization of Novel Influenza 2005.
"Collecting, Preserving, Shipping Specimens for the Diagnosis of Avian Influenza (H5N1) Virus Infection: Guide for Field Operations," WHO/CDS/EPR/ARO/2006.1 (2006).
Daum, et al., Abstract—"A Molecular Transport Medium (MTM) for Pathogen Inactivation, Ambient Transport and Preservation of RNA from Clinical Samples," ICAAC, Boston, MA, Sep. 12-15, 2010.
Daum, et al., Abstract and Poster—"Development of a Real Time Reverse-Transcription PCT (RRT-PCR) Assay for Detection of Influenza A H1N1 2009 From Clinical Respiratory Specimens," Pediatric Infectious Disease Conference ESPID, Nice, France, May 5-8, 2009.
Daum, et al., Abstract and Poster"Development of a Real Time Reverse-Transcription PCR (RRT-PCR) Assay for Detection of Influenza A H1N1 2009 from Clinical Respiratory Specimens," Pediatric Infectious Disease Conference ESPID, Nice, France, May 5-8 2010.
De Silva at al. Influenza A virus (A/Nonthaburi/102/2009(H1N1)) segment 4 hemagglutinin (HA) gene, partial cds. Genbank Accession No. GQ 132184.1, submitted May 9, 2009.
Spackman, E., et al., "Development of a Real-Time Reverse Transcriptase PCR Assay for Type A Influenza Vrius and the Avian H5 and H7 Hemagglutinin Subtypes," J. Clinic. Mirobiol., 40(9): 3256-60 (2002).
Hindiyeh et al. Journal of Clinical Microbiology, vol. 43, No. 2, pp. 589-595, Feb. 2005.
J. Mahoney et al., "Multiplex RT-PCR for detecting nineteen respiratory viruses," Journal of Clinical Virology, vol. 36, Jan. 1, 2006, p. S9.
"Adamantane Resistance Among Influenza, etc.", JAMA, Feb. 22, 2006, vol. 295, No. 8, pp. 891-894.
Jamie A. Blow et al., "Viral nucleic acid stabilization by RNA extraction reagent," Journal of Virological Methods, 150 (2008), Feb. 4, 2008, pp. 41-44.
"KOD Hot Start DNA Polymerase," Novagen, available at http://www.emdbiosciences.com/ProductDisplay.asp?catno=71086 (last visited Aug. 24, 2009).
Kutyavin et al. 3'-Minor groove binder-DNA probes increase sequence specificity at PCR extension temperatures. Nucleic Acid Res. (2000) vol. 28, No. 2, pp. 655-661.
"Genetic and Antigenic Analysis of the First A/New Calendonia, etc.", L.Daum, et al., Emerging Infectious Diseases, vol. 8, No. 4, Apr. 2002, pp. 408-412.
Canas, L.C., "Clinical Laboratory: Selection, Collection and Transport of Specimens for Viral Cultures." Department of the Air Force, Air Force Institute of Operational Health (AFIOH), Epidemiological Surveillance Division, SDE O1 44-5001, Virol. Proc. Man., 1-8 (2005).
Daum L.T., et al., "Molecular Analysis of Isolates From Influenza B Outbreaks in the U.S. and Nepal, 2005," Arch. of Virol., 151:1863-1874 (2006).
Daum, L.T. et al., "Real-Time RT-PCR Assays for Type and Subtype Detection of Influneza A and B Viruses," Influenza & Other Resp. Viruses 1(4): 167-75 (2007).
Daum, L.T., et al., "Abstract—Quantification of Influenza A Virus From Nasal and Lung Tissue of Cotton Rats Using Real-Time RT-PCR and Culture," 26th Annual Meeting of the European Society for Pediatric Infectious Diseases, Graz, Austria (2008).
Daum, L.T., et al., "Abstract—Development and Clinical Evaluation of Rapid Real-Time RT-PCR Assays for Detection of Influenza A and B Viruses," 26th Annual Meeting of the European Society for Pediatric Infectious Diseases, Graz, Austria (2008).
Daum, L.T., et al., "Poster—A Novel Specimen Collection Solution for Molecular Diagnostic Applications," The Pediatric Academic Societies (PAS) Annual Meeting, Honolulu, HI (2008).
Daum, L.T., et al., "Poster—A Rapid, Simplified Collection-to-Detection System for Typing and Subtyping Influenza Viruses Using Real-Time RT-PCR and Culture," American Society for Microbiology (ASM) Conference on Emerging Technologies of Medical Importance for the Diagnosis of Infectious Diseases and the Detection of Pathogenic Microbes, Beijing, China (2008).
Daum, L.T., et al., "Poster—Real-Time RT-PCR Detection of Influenza A Virus in Asymptomatic Culture-Negative Cotton Rats," The Pediatric Academic Societies (PAS) Annual Meeting, Honolulu, HI (2008).

(56) References Cited

OTHER PUBLICATIONS

Daum, L.T., et al., "A Rapid, Single-Step Multiplex Reverse Transcription-PCR Assay for the Detection of Human H1N1, H3N2 and B Influenza Viruses." J. of Clinic. Virol., 25(3): 345-50 (2002).
Daum, L.T., et al., "Real-Time RT-PCR Detection of Influenza Virus Within Symptomatic and Asymptomatic Family Members," The 48th Annual IDSA/ICAAC, Washington D.C. (2008).
Lowe et al. A computer program for selection of oligonucleotide primers for polymerase chain reactions. Nucleic Acids Research (1990) vol. 18, No. 7, pp. 1757-1761.
Luke T. Daum et al., "Detection and Molecular Characterization of Clinical Influenza A and B Viruses from Original Nasal Wash Specimens Preserved in PrimeStore," (2008).
Luke T. Daum et al., "Portugal Meeting Poster (Introduction, Materials, and Methods, Results, Discussion)," (2008).
"Luminex Confirms Effectiveness of xTAG Respiratory Viral Panel for Swine Flu Surveillance," Medical News Today, available at http://www.medicalnewstoday.com/printerfriendlynews.php?newsid=148498 (May 1, 2009).
"Luminex Receives FDA Clearance for an Update to the xTAG Respiratory Panel Insert Package Insert to Include Data from Two New Publications on 2009 Influenza A/H1N1," available at http://phx.corporate-ir.net/phoenix.zhtml?c=79403&p=irol-newsArticle&ID=1307416&highlight= (Jul. 14, 2009).
Borns, M. et al., "Most Accurate PCR Enzyme Inproved With Hot Start Feature," Biocompare, available at http://www.biocompare.com/technicalarticle/212/Most-Accurate-PCR-Enzyme-Improved-With-Hot-Start-Feature-from-Startagene.html (last visited Aug. 24, 2009).
Denhart, M., and Doraiswamy, V., "Master Your PCR Domain!" Promega Notes, 78: 9-12 (2001).
Master Your PCR Domain.
"Tools of Biochemistry 5A—Ways to Isolate and Purify Proteins and Other Macromolecules", Matthews, et al., Biochemistry, Second Edition, 1996, pp. 152-155.
Tortora, et al., "Tools of Biochemistry 5A—Ways to Isolate and Purify Proteins and Other Macromolecules," Microbiology—An Introduction, pp. 152-155, 4th Ed., The Benjamin/Cummings Publishing Company, Inc., United States (1992).
Matthews, et al., "Immunofluorescence and Fluorescent Antibody Techniques," Biochemistry, pp. 461-463, 2nd Ed., The Benjamin/Cummings Publishing Company, Inc., United States (1996).
Morre, et al., "RNA Amplification by Nucleic Acid Sequence-Based Amplification with an Internal Standard Enables Reliable Detection of *Chlamydia trachomatis* in Cervical Scrapings and Urine Samples," J. of Clinical Microbiol, 34(12): 3108-3114 (1996).
http://www.ncbi.nim.nih.gov/genomes/FLU/SwineFlu2009.html. NCBI Influenza Virus Resource "CLE I. GenBank Sequence from Pandemic (H1N1) 2009 Viruses". 1237 pages.
Pheng, O.C. Et al., "Temperature Related Storage Evaluation of an RT-PCR Test Kit for the Detection of Dengue Infection in Mosquitoes," (Research Note), Tropical Biomedicine, 22(1):73-6 (2005).
"Single-Step Method of RNA Isolation by Acid Guanidinium, etc.", P. Chomczyniski, et al., Analytical Biochemistry 162, 1987, pp. 156-159.
Pamphlet—"Prime PCR System"—Longhorn Vaccines & Disagnostics.
"PCR Optimization: Reaction Conditions and Components," Applied Biosystems, Part No. 4371091, Revision C, pp. 1-6 available at http://www.appliedbiosystems.com/cms/groups/mcb_marketing/documents/generaldocuments/cms_042520.pdf (last visited Aug. 24, 2009).
"PCR-Ready Clear Supreme," Syntezza Bioscience Ltd., available at http://www.syntezza.com/egt/PCR-Ready_Clear Supreme.pdf (2006).
European Patent Office, "PCT Notification of Transmittal of the International Search Report and the Written Opinion of the International Searching Authority or the Declaration, PCT International Search Report, PCT Written Opinion of the International Searching Authority—Application No. PCT/US2007/078025," Nov. 13, 2008, 10 pages, Munich.
European Patent Office, "PCT Notification of Transmittal of the International Search Report and the Written Opinion of the International Searching Authority—Application No. PCT/US2008/078499," dated Aug. 4, 2009, 13 pages.
Ramanujam, R. et al., "Room-Temperature-Stable PCR Reagents," Cold Spring Harbor Laboratory Press, PCR Methods and Appl., 3:75-76 (1993).
Bright, R.A., et al., "Adamantane Resistance Among Influenza A Viruses Isolated Early During the 2005-2006 Influenza Season in the United States," JAMA, 295(8):891-4 (Feb. 22, 2006).
Fouchier, R.A.M. et al., "Characterization of a Novel Influenza A Virus Hemagglutinin Subtype (H16) Obtained From Black-Headed Gulls," J. of Virol. 79(5):2814-22 (Mar. 2005).
"R.A.P.I.D System," Idaho Technology Inc., available at http://www.idahotech.com/RAPID/Rapid-Water.html (last visited Aug. 24, 2009).
Magari, R.T., Assessing shelf life using real-time and accelerated stability tests, BioPharm Nov. 2003.
Rosenstraus, et al., "An Internal Control for Routine Diagnostic PCR: Design, Properties, and Effect on Clinical Performance," J. of Clinical Microbial, 36(1): 191-197 (1998).
Blacksell, S.D. et al., "The Effect of Sample Degradation and RNA Stabilization on Classical Swine Fever Virus RT-PCR and Elisa methods," J. Virol. Methods, 118(1):33-7 (2004).
"Single Tube PCR Kit Manual," Takara Bio Inc., Cat #RR021, V.02.09, pp. 1-6 available at http://www.takara-bio.us/files/manuels/TAK_RR021_TM.pdf (last visited Aug. 24, 2009).
"Taq PCR Master Mix (2x)," USB Corp., (2007).
"TechNotes Newsletter," Applied Biosystems, 14(4):1-37 (2007).
"Immunoflourescence and Fluorescent-Antibody Techniques", Tortora, et al., Microbiology—An Introduction, Fourth Edition, 1992, pp. 461-463.
"USB Taq PCR Master Mix in qPCR," USB Corporation, Tech Tips, 207 (2005).
World Health Organization, "CDC protocol of realtime RTPCR for influenza A (H1N1)," Apr. 28, 2009.
Wiecek, A., "Pocket PCR: The Whole Chain Reaction in His Hand," Biotechniques.com, Oct. 26, 2010.
Wang, Z., et al., "Identifying Influenza Viruses with Resequencing Microarrays," Emerg. Infect. Dis. 12(4):638-46 (2006).
Danila Valmori et al. "Use of human universally antigenic tetanus toxin T cell epitopes as carriers for human vaccination" Journal of Immunology Jul. 15, 1992.
PCT Search Report for PCT/US2008/074521 dated Feb. 13, 2009.
PCT Written Opinion for PCT/US2008/074521 dated May 3, 2009.
PCT Search Report for PCT/US10/43546 dated Nov. 16, 2010.
PCT Search Report for PCT/US10/31716 dated Jul. 28, 2010.
PCT Written Opinion for PCT/US10/31716 dated Oct. 25, 2011.
De Folette et al. Vaccine 2006, Jun. 12, vol. 24, No. 44-46, pp. 6597-6601.
Galarza et al. Viral Immunity 2005, vol. 18, No. 2, pp. 365-372.
Arend et al. Infection and Immunity, 2000, vol. 68, No. 6, pp. 3314-3321.
Geysen, et al., "Use of Peptide Synthesis to Probe Viral Antigens for Epitopes to a Resolution of a Single Amino Acid," Proc. Natl. Acad. Sci., 81, pp. 3998-4002 (1984).
Tolman, et al., "Cyclic V3-Loop Related HIV-1 Conjugate Vaccines," Int. J. Peptide Protein Res., 41, pp. 455-466 (1993).
Conley, et al., "Immunogenicity of Synthetic HIV-1 Gp120 V3-Loop Peptide-Conjugate Immunogens," Vaccine, 12(5), pp. 445-451 (1994).
Schneider, et al., "Induction of CD8+T Cells Using Heterologous Prime-Boost Immunisation Strategies," Immunol. Rev., 170, pp. 29-38 (1999).
Tanghe, et al., "Improved Immunogenicity and Protective Efficacy of a Tuberculosis DNA Vaccine Encoding Ag85 by Protein Boosting," Infect. and Immun., 69(5), pp. 3041-3047 (2001).
Gonzalo, et al., "A Heterologous Prime-Boost Regime Using DNA and Recombinant Vaccinia Virus Expressing the Leishmania infantum P36/LACK Antigen Protects BALB/c Mice from Cutaneous Leishmaniasis," Vaccine, 20, pp. 1226-1231 (2002).
Meyer, et al., "Complement-Mediated Enhancement of Antibody Function for Neutralization of Pseudotype Virus Containing Hepatitis C Virus E2 Chimeric Glycoprotein," J. of Virol., 76(5) pp. 2150-2158 (2002).

(56) References Cited

OTHER PUBLICATIONS

Robinson, "New Hope for an Aids Vaccine," Nat. Rev. Immunol., 2, pp. 239-250 (Apr. 2002).
Lu, et al., "Multiepitope Trojan Antigen Peptide Vaccines for the Induction of Antitumor CTL and Th Immune Responses," J. of Immunol., 172, pp. 4575-4582 (2004).
Westerfield, et al., "Peptides Delivered by Immunostimulating Reconsituted Influenza Virosomes," J. of Peptide Sci., 11(11), pp. 707-712 (2005).
Gerhard, et al., "Prospects for Universal Influenza Virus," Emerging Infectious Diseases, 12(4), pp. 569-574 (Apr. 2006).
Luo, "Structural Biology: Antiviral Drugs Fit for a Purpose," Nature, 443, pp. 37-38 (Sep. 1, 2006).
PepTcell Ltd., "Technology," http://www.peptcell.com/technology.aspx (2007).
Stoloff, et al., "Synthetic Multi-Epitope Peptides Idenitifed in Silico Induce Protective Immunity Against Multiple Influeza Serotypes," Eur. J. of Immunol., 37(9), pp. 2441-2449 (Aug. 2, 2007).
Depla, et al., "Rational Design of a Multiepitope Vaccine Encoding T-Lymphocyte Epitopes for Treatment of Chronic Hepatitis B Virus Infections," J. of Virol., 82(1), pp. 435-450 (Jan. 2008).
Chien et al. J. Clin. Microbiol. 1999, vol. 37, No. 5, 1393-1397.
Ishioka et al. J. Immunol. vol. 162, pp. 3915-3925.
Lederman et al. Molecular Immunology 1991, vol. 28, No. 11, pp. 1171-1181.
PCT Search Report for PCT/US2007/078025 dated Oct. 28, 2008.
PCT Written Opinion for PCT/US2007/078025 dated Mar. 17, 2009.
PCT Search Report for PCT/US2008/078499 dated Jul. 23, 2009.
CA Office Action for PCT/US2007/078025, dated Jan. 4, 2011.
EPO Exam Report for PCT/US2007/078025, dated Dec. 30, 2011.
EPO Exam Report for PCT/US2007/078025, dated Aug. 26, 2010.
EPO Exam Report for PCT/US2007/078025, dated Jul. 6, 2009.
EPO Exam Report for PCT/US2007/078025, dated May 18, 2009.
AU Exam Report for PCT/US2007/078025, dated Nov. 19, 2010.
IL Exam Report for PCT/US2007/078025, dated Mar. 16, 2011.
NZ Exam Report for PCT/US2007/078025, dated Jul. 7, 2010.
Israel Office Action dated Jul. 19, 2012.
EPO Supplementary Search Report for PCT/US10/31761, dated Jul. 13, 2012.
CA Office Action for PCT/US2008/078499, dated Mar. 29, 2012.
PCT Written Opinion for PCT/US2008/078499, dated Jul. 4, 2010.
"Monolithic Silica Extraction Tips for Sample Preparation," CP-Analytica, available at http://cp-analytica (last visited Oct. 25, 2010).
Barnard, et al., "Suitability of new chlamydia transport medium for transport of herpes simplex virus," J. of Clin. Microbiol., 24(5): 692-695 (1986).
Eroglu, et al., "Successful cyropreservation of mouse oocytes by using low concentrations of trehalose and dimethylsylfoxide," Biol. of Rep. 80:70-78 (2009).
Gelmi, et al., "Bacertial survival in different transport media," European Congress of Clinical Microbiology and Infectious Diseases (ECCMID), May 28-31, 2000 (poster).
Higashiyama, T., "Novel functions and applications of terhalose," Pure Appl. Chem. 74(7): 1263-1269.
H1N1 RTPCR Primer/Probe Sets, Intergrated DNA Technologies—H1N1, available at http://www.idtdna.com/catalog/h1n1/page1.aspx.
Johnson, F.B., "Transport of viral specimens," Clin. Microbiol. Rev. 3(2): 120-131 (1990).
Sponseller, et al., "Influenza A pandemic (H1N1) 2009 virus infection in domestic cat," Emerg. Infect. Dis. (e-publication) (2010).
PCT Patentability Report for PCT/US2010/043546, dated Jan. 31, 2012.
PCT Search Report and Patentability Report for PCT/US2008/074521, dated Mar. 2, 2010.
Miyazaki, et al., "Development of a monolithic silica extraction top for the analysis of proteins," J. Chromatogr. A., 1043(1): 19-25 (2004) [abstract only].

PCT Patentability Report for PCT/US2012/35253, dated Sep. 21, 2012.
Taiwan Office Action dated Aug. 20, 2012.
Henke et al., Nucleic Acids Research 25(19): 3957-3958 (1997).
Yue et al., Diagnostic Microbiology and Infectious Disease, 48(1): 47-54 (2004).
Canadian Office Action for application No. 2697373, dated Feb. 19, 2013.
IL Exam Report for PCT/US2007/078025, dated Mar. 7, 2013.
EPO Exam Report for EP12180376, dated Feb. 8, 2013.
Canadian Office Action for application No. 2759028, dated Apr. 12, 2013.
Shapira M, Jibson M, Muller G, Arnon R. Immunity and protection against influenza virus by synthetic peptide corresponding to antigenic sites of hemagglutinin. Proc Natl Acad Sci U S A. Apr. 1984;81(8):2461-5.
Shah S, Raghupathy R, Singh O, Talwar GP, Sodhi A. Prior immunity to a carrier enhances antibody responses to hCG in recipients of an hCG-carrier conjugate vaccine. Vaccine. Aug. 6, 1999;17(23-24):3116-23. PubMed PMID: 10462248.
"Influenza: Immunogenicity and Vaccine Efficacy." Centers for Disease Control and Prevention (CDC) Pink Sheet. pp. 151-172. May 7, 2012.
"Tetanus: Immunogenicity and Vaccine Efficacy." Centers for Disease Control and Prevention (CDC) Pink Sheet. pp. 291-300. May 7, 2012.
Chamnanpood,P., Chamnanpood,C., Sanguansermsri,P. and Sanguansermsri,D. Characterization of HPAI H5N1 in Thailand: Jul.-Sep. 2004. NCBI GenBank Direct Submission. Apr. 25, 2005. Deposit No. AAY41867.
Fairweather,N.F., Lyness,V.A., Pickard,D.J., Allen,G, Thomson,R. O. Cloning, nucleotide sequencing, and expression of tetanus toxin fragment C in *Escherichia coli*. NCBI GenBank Dep. No. AAA23282, Apr. 26, 1993.
Hsu CT, Ting CY, Ting CJ, Chen TY, Lin CP, Whang-Peng J, Hwang J. Vaccination against gonadotropin-releasing hormone (GnRH) using toxin receptor-binding domain-conjugated GnRH repeats. Cancer Res. Jul. 15, 2000;60(14):3701-5.
Johansson J, Hellman L. Modifications increasing the efficacy of recombinant vaccines; marked increase in antibody titers with moderately repetitive variants of a therapeutic allergy vaccine. Vaccine. Feb. 19, 2007;25(9):1676-82. Epub Nov. 13, 2006.
Yankai Z, Rong Y, Yi H, Wentao L, Rongyue C, Ming Y, Taiming L, Jingjing L, Jie W. Ten tandem repeats of beta-hCG 109-118 enhance immunogenicity and anti-tumor effects of beta-hCG C-terminal peptide carried by mycobacterial heat-shock protein HSP65. Biochem Biophys Res Commun. Jul. 14, 2006;345(4):1365-71. Epub May 11, 2006.
PCT Search Report for PCT/US13/32354, dated May 31, 2013.
Chinese Office Action for Application No. 201080028416.4.
Chinese Search Report for Application No. 201080028416.4.
Henke et al., "Betaine Improves the PCR Amplification of GC-Rich DNA Sequences," Nucleic Acids Research 25(19): 3957-3958 (1997).
Yue et al., "Detection of rifampin-resistant *Mycobacterium tuberculosis* strains by using a specialized oligonucleotide microarray," Diagnostic Microbiology and Infectious Disease, 48(1): 47-54 (2004).
CA Office action for PCT/US08/78499, dated Mar. 29, 2012.
Daum, et al., Abstract and Poster—"Development of a Real Time Reverse-Transcription PCR (RRT-PCR) Assay for Detection of Influenza A H1N1 2009 From Clinical Respiratory Specimens," Pediatric Infectious Disease Conference ESPID, Nice, France, May 5-8, 2009.
RU 2150281.
Valmori, et al., "Use of Human Universally Antigenic Tetanus Toxin T Cell Epitopes as Carriers for Human Vaccination," *J. of Immunol.*, 149(2), pp. 717-721 (1992).
Westerfeld, et al., "Peptides Delivered by Immunostimulating Reconstituted Influenza Virosomes," *J. of Peptide Sci.*, 11(11), pp. 707-712 (2005).
Stoloff, et al., "Synthetic Multi-Epitope Peptides Identified in Silico Induce Protective Immunity Against Multiple Influenza Serotypes," *Eur. J. of Immunol.*, 37(9), pp. 2441-2449 (Aug. 2, 2007).

(56) References Cited

OTHER PUBLICATIONS

Blow, et al., "Viral Nucleic Acid Stabilization by RNA Extraction Reagent," *J. of Virol. Meth.,* 150, pp. 41-44 (Apr. 2, 2008).
CA Exam Report for Application No. 2,863,083 dated Nov. 28, 2019.

| VACCINE DESIGNATION | SERUM ID | ANTISERA MEAN OD |
|---|---|---|
| PEP 3 | 2741 | 0.861 |
| PEP 3 | 2741 | 0.786 |
| PEP 3 | 2743 | 0.794 |
| PEP 3 | 2744 | 0.048 - PREBLEED |
| PEP 3 | 2745 | 0.053 - PREBLEED |
| PEP 3 | 2746 | 0.047 - PREBLEED |
| PEP 6 | 59576 | 0.057 - PREBLEED |
| PEP 6 | 59576 | 0.216 |
| PEP 6 | 59576 | 0.369 |
| PEP 6 | 59577 | 0.057 - PREBLEED |
| PEP 6 | 59578 | 0.476 |
| PEP 6 | 59578 | 0.068 - PREBLEED |
| PEP 6 | 59578 | 0.215 |
| PEP 6 | 59578 | 0.476 |
| PEP 9 | 2731 | 1.428 |
| PEP 9 | 2731 | 0.537 |
| PEP 9 | 2732 | 1.707 |
| PEP 9 | 2734 | 1.862 |
| PEP 9 | 2735 | 1.693 |
| PEP 10 | 8241 | 0.711 |
| PEP 10 | 8242 | 2.026 |
| PEP 10 | 8255 | 1.373 |
| PEP 10 | 8256 | 2.874 |
| PEP 10 | 8256 | 1.405 |
| PEP 10 | 8257 | 1.457 |
| PEP 11 | 61758 | 2.611 |
| PEP 11 | 61758 | 1.962 |
| PEP 11 | 61759 | 0.099 - PREBLEED |
| PEP 11 | 61759 | 0.504 |
| PEP 11 | 61759 | 1.282 |
| PEP 11 | 61760 | 0.976 |
| PEP 11 | 1759 | 1.450 |

*FIG. 1*

ANTISERA TITERS FOR MICE IMMUNIZED WITH PEP11 ON H5N1 AT VARIOUS DILUTIONS

— ● — SERUM 758 D-42
— ■ — SERUM 759 D-42

FIG. 7

| DESIGNATION | DESIGNATION | PEPTIDE | N-TERM | FLU PEPTIDE SEQUENCE | SEQ ID NO |
|---|---|---|---|---|---|
| 9007 / PEP1<br>PEP1 +CAGA* | LH-PSEQ-001A<br>LH-PSEQ-001A +CAGA* | 1<br>1 | NH2<br>NH2 | GNFIAP<br>CAGAGNFIAP | 4<br>80 |
| 9009 / PEP2<br>PEP2 +CAGA* | LH-PSEQ-002A<br>LH-PSEQ-002A +CAGA* | 2<br>2 | NH2<br>NH2 | GNLIAP<br>CAGAGNLIAP | 5<br>81 |
| 9011 / PEP3<br>PEP3<br>PEP3 +CAGA* | LH-PSEQ-003A<br><br>LH-PSEQ-003A +CAGA* | 3<br>3<br>3 | NH2<br>NH2<br>NH2 | GNLFIAP<br>GNLFIAP<br>CAGAGNLFIAP | 6<br>6<br>82 |
| 9013 / PEP4<br>PEP4 +CAGA* | LH-PSEQ-004A<br>LH-PSEQ-004A +CAGA* | 4<br>4 | NH2<br>NH2 | WGVHHP<br>CAGAWGVHHP | 53<br>83 |
| 9015 / PEP5<br>PEP5 +CAGA* | LH-PSEQ-005A<br>LH-PSEQ-005A +CAGA* | 5<br>5 | NH2<br>NH2 | WGIHHP<br>CAGAWGIHHP | 52<br>84 |
| 9017 / PEP6<br>PEP6<br>PEP6 + CAGA* | LH-PSEQ-006A<br>LH-PSEQ-006B<br>LH-PSEQ-006A +CAGA* | 6<br>6<br>6 | NH2<br>NH2<br>NH2 | WGVIHHP<br>WGVIHHP<br>CAGAWGVIHHP | 54<br>54<br>85 |
| 9019 / PEP7<br>PEP7<br>PEP7 + CAGA* | LH-PSEQ-007A<br>LH-PSEQ-007B<br>LH-PSEQ-007A +CAGA* | 7<br>7<br>7 | NH2<br>NH2<br>NH2 | WGIVHHP<br>WGIVHHP<br>CAGAWGIVHHP | 55<br>55<br>86 |
| 9021 / PEP8<br>PEP8 + CAGA* | LH-PSEQ-008A<br>LH-PSEQ-008A +CAGA* | 8<br>8 | NH2<br>NH2 | GNLIAPWGVIHHP<br>CAGAGNLIAPWGVIHHP | 87<br>88 |
| 9023 / PEP9<br>PEP9<br>PEP9 + CAGA* | LH-PSEQ-009A<br>LH-PSEQ-009B<br>LH-PSEQ-009A +CAGA* | 9<br>9<br>9 | NH2<br>NH2<br>NH2 | GNLFIAPWGVIHHP<br>GNLFIAPWGVIHHP<br>CAGAGNLFIAPWGVIHHP | 89<br>89<br>90 |

* SEQ ID NO:116

FIG. 8-1

| FIG. 8-1 | FIG. 8-2 |
|---|---|
| FIG. 8-3 | FIG. 8-4 |
| FIG. 8-5 | FIG. 8-6 |

| C-TERM | CAGA YES/NO | IMPORTANT NOTES |
|---|---|---|
| COOH COOH | NO YES | NATIVE; H5; HEMAGGLUTININ |
| COOH COOH | NO YES | NATIVE; H1 & H3; HEMAGGLUTININ |
| COOH COOH COOH | NO NO YES | COMPOSITE; H1, H3 & H5; BINDS TO ANTIBODY |

| DESIGNATION | DESIGNATION | PEPTIDE | N-TERM | FLU PEPTIDE SEQUENCE | SEQ ID NO |
|---|---|---|---|---|---|
| 9025 / PEP10 | LH-PSEQ-010A | 10 | NH2 | HYEECSCY | 91 |
| PEP10 | LH-PSEQ-010B | 10 | NH2 | HYEECSCY | 91 |
| PEP10 + CAGA* | LH-PSEQ-010A +CAGA* | 10 | NH2 | CAGAHYEECSCY | 92 |
| 9027 / PEP11 | LH-PSEQ-011A | 11 | NH2 | GNLFIAPWGVIHHPHYEECSCY | 93 |
| PEP11 | LH-PSEQ-011B | 11 | NH2 | GNLFIAPWGVIHHPHYEECSCY | 93 |
| PEP11 + CAGA* | LH-PSEQ-011A +CAGA* | 11 | NH2 | CAGAGNLFIAPWGVIHHPHYEECSCY | 94 |
| 9029 / PEP12 | LH-PSEQ-012A | 12 | NH2 | GNLFIAPWGVIHHPGNLFIAPWGVIHHP | 95 |
| PEP12 + CAGA* | LH-PSEQ-012A +CAGA* | 12 | NH2 | CAGAGNLFIAPWGVIHHPGNLFIAPWGVIHHP | 96 |
| 50 | LH-PSEQ-018A | 50 | NH2 | HYEECSCYGNLFIAPWGVIHHP | 97 |
| 51 | LH-PSEQ-019A | 51 | NH2 | GNLFIAPHYEECSCYWGVIHHP | 98 |
| 52 | LH-PSEQ-020A | 52 | NH2 | ETPIRNE | 2 |
| 5906 | LH-PSEQ-021A | 5906 | NH2 | SLLTEVETPIRNEWGLLTEVETPIRQYIKANSKFIGITE | 99 |
| 5906 | LH-PSEQ-021B | 5906 | NH2 | SLLTEVETPIRNEWGLLTEVETPIRQYIKANSKFIGITE | 99 |
| 5907 | LH-PSEQ-022A | 5907 | NH2 | GNLFIAPGNLFIAPQYIKANSKFIGITEGNLFIAP | 100 |
| 5908 | LH-PSEQ-023A | 5908 | NH2 | HYEECSCYDWSGYSGSFVQHPELTGLHYEECSCYQYIKANSKFIGITE | 101 |
| 5909 | LH-PSEQ-024A | 5909 | NH2 | VTREPYVSCDPKSCINRCFYVELIRGRVTREPYVSCDPQYIKANSKFIGITE | 102 |
| 5910 | LH-PSEQ-025A | 5910 | NH2 | GNLFIAP | 6 |
| 5911 | LH-PSEQ-026A | 5911 | NH2 | HYEECSCY | 91 |
| 5912 | LH-PSEQ-027A | 5912 | NH2 | DWSGYSGSFVQHPELTGL | 103 |
| 5913 | LH-PSEQ-028A | 5913 | NH2 | ITGFAPFSKDNSIRLSAGGDIWVTREPYVSCDP | 104 |
| 5914 | LH-PSEQ-029A | 5914 | NH2 | KSCINRCFYVELIRGR | 105 |

* SEQ ID NO:116

FIG. 8-3

| FIG. 8-1 | FIG. 8-2 |
|---|---|
| FIG. 8-3 | FIG. 8-4 |
| FIG. 8-5 | FIG. 8-6 |

| C-TERM | CAGA YES/NO | IMPORTANT NOTES |
|---|---|---|
| COOH<br>COOH<br>COOH | NO<br>NO<br>YES | NEUR

| DESIGNATION | DESIGNATION | PEPTIDE | N-TERM | FLU PEPTIDE SEQUENCE | SEQ ID NO |
|---|---|---|---|---|---|
| PEPTIDE 6 / PEP1B | LH-PSEQ-013A | 1 | NH2 | GNLFIAPRYAFA | 106 |
| PEP1B +CAGA | LH-PSEQ-013A +CAGA* | 1 | NH2 | CAGAGNLFIAPRYAFA | 107 |
| PEPTIDE 6 / PEP1C | LH-PSEQ-013A | 1 | NH2 | GNLFIAPRYAFA | 106 |
| PEP1C +CAGA* | LH-PSEQ-013A +CAGA* | 1 | NH2 | CAGAGNLFIAPRYAFA | 107 |
| PEPTIDE 7 / PEP2 NEW | LH-PSEQ-014A | 2 | NH2 | GNLVVPRYAFA | 108 |
| PEP2 NEW +CAGA* | LH-PSEQ-014A +CAGA* | 2 | NH2 | CAGAGNLVVPRYAFA | 109 |
| PEPTIDE 8 / PEP3 NEW | LH-PSEQ-015A | 3 | NH2 | GNLIAPRYAFA | 110 |
| PEP3 NEW +CAGA* | LH-PSEQ-015A +CAGA* | 3 | NH2 | CAGAGNLIAPRYAFA | 111 |
| PEPTIDE 9 / PEP4 NEW | LH-PSEQ-016A | 4 | NH2 | GNLVVP | 112 |
| PEP4 NEW +CAGA* | LH-PSEQ-016A +CAGA* | 4 | NH2 | CAGAGNLVVP | 113 |
| PEPTIDE 10 / PEP5 NEW | LH-PSEQ-017A | 5 | NH2 | FVIREPFISCSHLEC | 114 |
| PEP5 NEW +CAGA* | LH-PSEQ-017A +CAGA* | 5 | NH2 | CAGAFVIREPFISCSHLEC | 115 |

* SEQ ID NO:116

FIG. 8-5

| C-TERM | CAGA YES/NO | IMPORTANT NOTES |
|---|---|---|
| COOH COOH COOH COOH | NO YES NO YES | |
| COOH COOH | NO YES | |
| COOH COOH | NO YES | |
| COOH COOH | NO YES | |
| COOH COOH | NO YES | |

*FIG. 8-6*

| FIG. 8-1 | FIG. 8-2 |
|---|---|
| FIG. 8-3 | FIG. 8-4 |
| FIG. 8-5 | FIG. 8-6 |

```
SEQUENCE LISTING

<160> NUMBER OF SEQ ID NOS: 116

<210> SEQ ID NO 1
<211> LENGTH: 19
<212> TYPE: PRT
<213> ORGANISM: Influenza virus

<400> SEQUENCE: 1

Asp Trp Ser Gly Tyr Ser Gly Ser Phe Val Gln His Pro Glu Leu Thr
1               5                   10                  15

Gly Leu Asp

<210> SEQ ID NO 2
<211> LENGTH: 7
<212> TYPE: PRT
<213> ORGANISM: Influenza virus

<400> SEQUENCE: 2

Glu Thr Pro Ile Arg Asn Glu
1               5

<210> SEQ ID NO 3
<211> LENGTH: 15
<212> TYPE: PRT
<213> ORGANISM: Influenza virus

<400> SEQUENCE: 3

Phe Val Ile Arg Glu Pro Phe Ile Ser Cys Ser His Leu Glu Cys
1               5                   10                  15

<210> SEQ ID NO 4
<211> LENGTH: 6
<212> TYPE: PRT
<213> ORGANISM: Influenza virus

<400> SEQUENCE: 4

Gly Asn Phe Ile Ala Pro
1               5

<210> SEQ ID NO 5
<211> LENGTH: 6
<212> TYPE: PRT
<213> ORGANISM: Influenza virus

<400> SEQUENCE: 5

Gly Asn Leu Ile Ala Pro
1               5
```

```
<210> SEQ ID NO 6
<211> LENGTH: 7
<212> TYPE: PRT
<213> ORGANISM: Influenza virus

<400> SEQUENCE: 6

Gly Asn Leu Phe Ile Ala Pro
1               5

<210> SEQ ID NO 7
<211> LENGTH: 7
<212> TYPE: PRT
<213> ORGANISM: Influenza virus

<400> SEQUENCE: 7

Gly Asn Leu Ile Phe Ala Pro
1               5

<210> SEQ ID NO 8
<211> LENGTH: 8
<212> TYPE: PRT
<213> ORGANISM: Influenza virus

<400> SEQUENCE: 8

His Tyr Glu Glu Cys Ser Cys Tyr
1               5

<210> SEQ ID NO 9
<211> LENGTH: 10
<212> TYPE: PRT
<213> ORGANISM: Influenza virus

<400> SEQUENCE: 9

Leu Leu Thr Glu Val Glu Thr Pro Ile Arg
1               5                   10

<210> SEQ ID NO 10
<211> LENGTH: 11
<212> TYPE: PRT
<213> ORGANISM: Influenza virus

<400> SEQUENCE: 10

Leu Leu Thr Glu Val Glu Thr Pro Ile Arg Asn
1               5                   10

<210> SEQ ID NO 11
<211> LENGTH: 12
<212> TYPE: PRT
<213> ORGANISM: Influenza virus

<400> SEQUENCE: 11

Leu Leu Thr Glu Val Glu Thr Pro Ile Arg Asn Glu
1               5                   10

<210> SEQ ID NO 12
<211> LENGTH: 18
<212> TYPE: PRT
<213> ORGANISM: Influenza virus

<400> SEQUENCE: 12

Asp Trp Ser Gly Tyr Ser Gly Ser Phe Val Gln His Pro Glu Leu Thr
1               5                   10                  15

Gly Leu
```

-continued

<210> SEQ ID NO 13
<211> LENGTH: 9
<212> TYPE: PRT
<213> ORGANISM: Influenza virus

<400> SEQUENCE: 13

Glu Val Glu Thr Pro Ile Arg Asn Glu
1 5

<210> SEQ ID NO 14
<211> LENGTH: 38
<212> TYPE: PRT
<213> ORGANISM: Influenza virus

<400> SEQUENCE: 14

Phe Leu Leu Pro Glu Asp Glu Thr Pro Ile Arg Asn Glu Trp Gly Leu
1 5 10 15

Leu Thr Asp Asp Glu Thr Pro Ile Arg Tyr Ile Lys Ala Asn Ser Lys
20 25 30

Phe Ile Gly Ile Thr Glu
35

<210> SEQ ID NO 15
<211> LENGTH: 64
<212> TYPE: PRT
<213> ORGANISM: Influenza virus

<400> SEQUENCE: 15

Gly Asn Leu Phe Ile Ala Pro Gly Asn Leu Phe Ile Ala Pro His Tyr
1 5 10 15

Glu Glu Cys Ser Cys Tyr His Tyr Glu Glu Cys Ser Cys Tyr Gln Tyr
20 25 30

Ile Lys Ala Asn Ser Lys Phe Ile Gly Ile Thr Glu His Tyr Glu Glu
35 40 45

Cys Ser Cys Tyr Thr Pro Ile Arg Asn Glu Thr Pro Ile Arg Asn Glu
50 55 60

<210> SEQ ID NO 16
<211> LENGTH: 35
<212> TYPE: PRT
<213> ORGANISM: Influenza virus

<400> SEQUENCE: 16

Gly Asn Leu Phe Ile Ala Pro Gly Asn Leu Phe Ile Ala Pro Gln Tyr
1 5 10 15

Ile Lys Ala Asn Ser Lys Phe Ile Gly Ile Thr Glu Gly Asn Leu Phe
20 25 30

Ile Ala Pro
35

<210> SEQ ID NO 17
<211> LENGTH: 48
<212> TYPE: PRT
<213> ORGANISM: Influenza virus -continued

```
<400> SEQUENCE: 17

His Tyr Glu Glu Cys Ser Cys Tyr Asp Trp Ser Gly Tyr Ser Gly Ser
1               5                   10                  15

Phe Val Gln His Pro Glu Leu Thr Gly Leu His Tyr Glu Glu Cys Ser
                20                  25                  30

Cys Tyr Gln Tyr Ile Lys Ala Asn Ser Lys Phe Ile Gly Ile Thr Glu
            35                  40                  45

<210> SEQ ID NO 18
<211> LENGTH: 33
<212> TYPE: PRT
<213> ORGANISM: Influenza virus

<400> SEQUENCE: 18

Ile Thr Gly Phe Ala Pro Phe Ser Lys Asp Asn Ser Ile Arg Leu Ser
1               5                   10                  15

Ala Gly Gly Asp Ile Trp Val Thr Arg Glu Pro Tyr Val Ser Cys Asp
                20                  25                  30

Pro

<210> SEQ ID NO 19
<211> LENGTH: 7
<212> TYPE: PRT
<213> ORGANISM: Influenza virus

<400> SEQUENCE: 19

Ile Trp Gly Ile His His Pro
1               5

<210> SEQ ID NO 20
<211> LENGTH: 7
<212> TYPE: PRT
<213> ORGANISM: Influenza virus

<400> SEQUENCE: 20

Ile Trp Gly Val His His Pro
1               5

<210> SEQ ID NO 21
<211> LENGTH: 8
<212> TYPE: PRT
<213> ORGANISM: Influenza virus

<400> SEQUENCE: 21

Ile Trp Gly Val Ile His His Pro
1               5

<210> SEQ ID NO 22
<211> LENGTH: 8
<212> TYPE: PRT
<213> ORGANISM: Influenza virus

<400> SEQUENCE: 22

Ile Trp Gly Ile Val His His Pro
1               5

<210> SEQ ID NO 23
<211> LENGTH: 16
<212> TYPE: PRT
<213> ORGANISM: Influenza virus
```

```
<400> SEQUENCE: 23

Lys Ser Cys Ile Asn Arg Cys Phe Tyr Val Glu Leu Ile Arg Gly Arg
1               5                   10                  15

<210> SEQ ID NO 24
<211> LENGTH: 27
<212> TYPE: PRT
<213> ORGANISM: Influenza virus

<400> SEQUENCE: 24

Leu Leu Thr Glu Val Glu Thr Pro Ile Arg Asn Glu Ser Leu Leu Thr
1               5                   10                  15

Glu Val Glu Thr Pro Ile Arg Asn Glu Trp Gly
            20                  25

<210> SEQ ID NO 25
<211> LENGTH: 13
<212> TYPE: PRT
<213> ORGANISM: Influenza virus

<400> SEQUENCE: 25

Leu Leu Thr Glu Val Glu Thr Pro Ile Arg Asn Glu Trp
1               5                   10

<210> SEQ ID NO 26
<211> LENGTH: 14
<212> TYPE: PRT
<213> ORGANISM: Influenza virus

<400> SEQUENCE: 26

Leu Leu Thr Glu Val Glu Thr Pro Ile Arg Asn Glu Trp Gly
1               5                   10

<210> SEQ ID NO 27
<211> LENGTH: 11
<212> TYPE: PRT
<213> ORGANISM: Influenza virus

<400> SEQUENCE: 27

Leu Thr Glu Val Glu Thr Pro Ile Arg Asn Glu
1               5                   10

<210> SEQ ID NO 28
<211> LENGTH: 12
<212> TYPE: PRT
<213> ORGANISM: Influenza virus

<400> SEQUENCE: 28

Leu Thr Glu Val Glu Thr Pro Ile Arg Asn Glu Trp
1               5                   10

<210> SEQ ID NO 29
<211> LENGTH: 13
<212> TYPE: PRT
<213> ORGANISM: Influenza virus

<400> SEQUENCE: 29

Leu Thr Glu Val Glu Thr Pro Ile Arg Asn Glu Trp Gly
1               5                   10

<210> SEQ ID NO 30
<211> LENGTH: 9
<212> TYPE: PRT
<213> ORGANISM: Influenza virus
```

<400> SEQUENCE: 30

Met Ser Leu Leu Thr Glu Val Glu Thr
1               5

<210> SEQ ID NO 31
<211> LENGTH: 10
<212> TYPE: PRT
<213> ORGANISM: Influenza virus

<400> SEQUENCE: 31

Met Ser Leu Leu Thr Glu Val Glu Thr Pro
1               5                   10

<210> SEQ ID NO 32
<211> LENGTH: 11
<212> TYPE: PRT
<213> ORGANISM: Influenza virus

<400> SEQUENCE: 32

Met Ser Leu Leu Thr Glu Val Glu Thr Pro Ile
1               5                   10

<210> SEQ ID NO 33
<211> LENGTH: 12
<212> TYPE: PRT
<213> ORGANISM: Influenza virus

<400> SEQUENCE: 33

Met Ser Leu Leu Thr Glu Val Glu Thr Pro Ile Arg
1               5                   10

<210> SEQ ID NO 34
<211> LENGTH: 13
<212> TYPE: PRT
<213> ORGANISM: Influenza virus

<400> SEQUENCE: 34

Met Ser Leu Leu Thr Glu Val Glu Thr Pro Ile Arg Asn
1               5                   10

<210> SEQ ID NO 35
<211> LENGTH: 14
<212> TYPE: PRT
<213> ORGANISM: Influenza virus

<400> SEQUENCE: 35

Met Ser Leu Leu Thr Glu Val Glu Thr Pro Ile Arg Asn Glu
1               5                   10

<210> SEQ ID NO 36
<211> LENGTH: 20
<212> TYPE: PRT
<213> ORGANISM: Influenza virus

<400> SEQUENCE: 36

Met Ser Leu Leu Thr Glu Val Glu Thr Pro Ile Arg Asn Glu Thr Pro
1               5                   10                  15

Ile Arg Asn Glu
            20

<210> SEQ ID NO 37
<211> LENGTH: 15
<212> TYPE: PRT
<213> ORGANISM: Influenza virus

<400> SEQUENCE: 37

Met Ser Leu Leu Thr Glu Val Glu Thr Pro Ile Arg Asn Glu Trp
1               5                   10                  15

<210> SEQ ID NO 38
<211> LENGTH: 16
<212> TYPE: PRT
<213> ORGANISM: Influenza virus

<400> SEQUENCE: 38

Met Ser Leu Leu Thr Glu Val Glu Thr Pro Ile Arg Asn Glu Trp Gly
1               5                   10                  15

<210> SEQ ID NO 39
<211> LENGTH: 24
<212> TYPE: PRT
<213> ORGANISM: Influenza virus

<400> SEQUENCE: 39

Met Ser Leu Leu Thr Glu Val Glu Thr Pro Ile Arg Asn Glu Trp Gly
1               5                   10                  15

Cys Arg Cys Asn Asp Ser Ser Asp
            20

<210> SEQ ID NO 40
<211> LENGTH: 8
<212> TYPE: PRT
<213> ORGANISM: Influenza virus

<400> SEQUENCE: 40

Ser Leu Leu Thr Glu Val Glu Thr
1               5

<210> SEQ ID NO 41
<211> LENGTH: 13
<212> TYPE: PRT
<213> ORGANISM: Influenza virus

<400> SEQUENCE: 41

Ser Leu Leu Thr Glu Val Glu Thr Pro Ile Arg Asn Glu
1               5                   10

<210> SEQ ID NO 42
<211> LENGTH: 14
<212> TYPE: PRT
<213> ORGANISM: Influenza virus

<400> SEQUENCE: 42

Ser Leu Leu Thr Glu Val Glu Thr Pro Ile Arg Asn Glu Trp
1               5                   10

<210> SEQ ID NO 43
<211> LENGTH: 15
<212> TYPE: PRT
<213> ORGANISM: Influenza virus

<400> SEQUENCE: 43

Ser Leu Leu Thr Glu Val Glu Thr Pro Ile Arg Asn Glu Trp Gly
1               5                   10                  15

<210> SEQ ID NO 44
<211> LENGTH: 21
<212> TYPE: PRT
<213> ORGANISM: Influenza virus -continued

```
<400> SEQUENCE: 44

Ser Leu Leu Thr Glu Val Glu Thr Pro Ile Arg Asn Glu Trp Gly Thr
1               5                   10                  15

Pro Ile Arg Asn Glu
            20

<210> SEQ ID NO 45
<211> LENGTH: 27
<212> TYPE: PRT
<213> ORGANISM: Influenza virus

<400> SEQUENCE: 45

Ser Leu Leu Thr Glu Val Glu Thr Pro Ile Arg Asn Glu Trp Gly Thr
1               5                   10                  15

Pro Ile Arg Asn Glu Thr Pro Ile Arg Asn Glu
            20                  25

<210> SEQ ID NO 46
<211> LENGTH: 33
<212> TYPE: PRT
<213> ORGANISM: Influenza virus

<400> SEQUENCE: 46

Ser Leu Leu Thr Glu Val Glu Thr Pro Ile Arg Asn Glu Trp Gly Thr
1               5                   10                  15

Pro Ile Arg Asn Glu Thr Pro Ile Arg Asn Glu Thr Pro Ile Arg Asn
            20                  25                  30

Glu

<210> SEQ ID NO 47
<211> LENGTH: 39
<212> TYPE: PRT
<213> ORGANISM: Influenza virus

<400> SEQUENCE: 47

Ser Leu Leu Thr Glu Val Glu Thr Pro Ile Arg Asn Glu Trp Gly Leu
1               5                   10                  15

Leu Thr Glu Val Glu Thr Pro Ile Arg Gln Tyr Ile Lys Ala Asn Ser
            20                  25                  30

Lys Phe Ile Gly Ile Thr Glu
        35

<210> SEQ ID NO 48
<211> LENGTH: 10
<212> TYPE: PRT
<213> ORGANISM: Influenza virus

<400> SEQUENCE: 48

Thr Glu Val Glu Thr Pro Ile Arg Asn Glu
1               5                   10

<210> SEQ ID NO 49
<211> LENGTH: 6
<212> TYPE: PRT
<213> ORGANISM: Influenza virus

<400> SEQUENCE: 49

Thr Pro Ile Arg Asn Glu
1               5
```

```
<210> SEQ ID NO 50
<211> LENGTH: 8
<212> TYPE: PRT
<213> ORGANISM: Influenza virus

<400> SEQUENCE: 50

Val Glu Thr Pro Ile Arg Asn Glu
1               5

<210> SEQ ID NO 51
<211> LENGTH: 52
<212> TYPE: PRT
<213> ORGANISM: Influenza virus

<400> SEQUENCE: 51

Val Thr Arg Glu Pro Tyr Val Ser Cys Asp Pro Lys Ser Cys Ile Asn
1               5                   10                  15

Arg Cys Phe Tyr Val Glu Leu Ile Arg Gly Arg Val Thr Arg Glu Pro
            20                  25                  30

Tyr Val Ser Cys Asp Pro Trp Tyr Ile Lys Ala Asn Ser Lys Phe Ile
        35                  40                  45

Gly Ile Thr Glu
    50

<210> SEQ ID NO 52
<211> LENGTH: 6
<212> TYPE: PRT
<213> ORGANISM: Influenza virus

<400> SEQUENCE: 52

Trp Gly Ile His His Pro
1               5

<210> SEQ ID NO 53
<211> LENGTH: 6
<212> TYPE: PRT
<213> ORGANISM: Influenza virus

<400> SEQUENCE: 53

Trp Gly Val His His Pro
1               5

<210> SEQ ID NO 54
<211> LENGTH: 7
<212> TYPE: PRT
<213> ORGANISM: Influenza virus

<400> SEQUENCE: 54

Trp Gly Val Ile His His Pro
1               5

<210> SEQ ID NO 55
<211> LENGTH: 7
<212> TYPE: PRT
<213> ORGANISM: Influenza virus

<400> SEQUENCE: 55

Trp Gly Ile Val His His Pro
1               5

<210> SEQ ID NO 56
<211> LENGTH: 8
<212> TYPE: PRT
<213> ORGANISM: Influenza virus
```

```
<400> SEQUENCE: 56

Tyr Ile Trp Gly Ile His His Pro
1               5

<210> SEQ ID NO 57
<211> LENGTH: 8
<212> TYPE: PRT
<213> ORGANISM: Influenza virus

<400> SEQUENCE: 57

Tyr Ile Trp Gly Val His His Pro
1               5

<210> SEQ ID NO 58
<211> LENGTH: 9
<212> TYPE: PRT
<213> ORGANISM: Influenza virus

<400> SEQUENCE: 58

Tyr Ile Trp Gly Val Ile His His Pro
1               5

<210> SEQ ID NO 59
<211> LENGTH: 9
<212> TYPE: PRT
<213> ORGANISM: Influenza virus

<400> SEQUENCE: 59

Tyr Ile Trp Gly Ile Val His His Pro
1               5

<210> SEQ ID NO 60
<211> LENGTH: 14
<212> TYPE: PRT
<213> ORGANISM: Influenza virus

<400> SEQUENCE: 60

Gln Tyr Ile Lys Ala Asn Ser Lys Phe Ile Gly Ile Thr Glu
1               5                   10

<210> SEQ ID NO 61
<211> LENGTH: 15
<212> TYPE: PRT
<213> ORGANISM: Influenza virus

<400> SEQUENCE: 61

Pro Ile Arg Asn Glu Trp Gly Cys Arg Cys Asn Asp Ser Ser Asp
1               5                   10                  15

<210> SEQ ID NO 62

<400> SEQUENCE: 62

000

<210> SEQ ID NO 63

<400> SEQUENCE: 63

000
```

<210> SEQ ID NO 64

<400> SEQUENCE: 64

000

<210> SEQ ID NO 65
<211> LENGTH: 372
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

```
Ser Glu Tyr Ala Tyr Gly Ser Phe Val Arg Thr Val Ser Leu Pro Val
1               5                   10                  15

Gly Ala Asp Glu Gly Asn Leu Phe Ile Ala Pro Trp Gly Val Ile His
            20                  25                  30

His Pro His Tyr Glu Glu Cys Ser Cys Tyr Gly Leu Pro Val Glu Tyr
        35                  40                  45

Leu Gln Val Pro Ser Pro Ser Met Gly Arg Asp Ile Lys Val Gln Phe
    50                  55                  60

Gln Ser Gly Gly Ala Asn Ser Pro Ala Leu Tyr Leu Leu Asp Gly Leu
65                  70                  75                  80

Arg Ala Gln Asp Asp Phe Ser Gly Trp Asp Ile Asn Thr Pro Ala Phe
                85                  90                  95

Glu Trp Tyr Asp Gln Ser Gly Leu Ser Val Val Met Pro Val Gly Gly
            100                 105                 110

Gln Ser Ser Phe Tyr Ser Asp Trp Tyr Gln Pro Ala Cys Arg Lys Ala
        115                 120                 125

Gly Cys Gln Thr Tyr Lys Trp Glu Thr Phe Leu Thr Ser Glu Leu Pro
    130                 135                 140

Gly Trp Leu Gln Ala Asn Arg His Val Gln Pro Thr Gly Ser Ala Val
145                 150                 155                 160

Val Gly Leu Ser Met Ala Ala Ser Ser Ala Leu Thr Leu Ala Ile Tyr
                165                 170                 175

His Pro Gln Gln Phe Val Tyr Ala Gly Ala Met Ser Gly Leu Leu Asp
            180                 185                 190

Pro Ser Gln Ala Met Gly Pro Thr Leu Ile Gly Leu Ala Met Gly Asp
        195                 200                 205

Ala Gly Gly Tyr Lys Ala Ser Asp Met Trp Gly Pro Lys Glu Asp Pro
    210                 215                 220

Ala Trp Gln Arg Asn Asp Pro Leu Leu Asn Val Gly Lys Leu Ile Ala
225                 230                 235                 240

Asn Asn Thr Arg Val Trp Val Tyr Cys Gly Asn Gly Lys Pro Ser Asp
                245                 250                 255

Leu Gly Gly Asn Asn Leu Pro Ala Lys Phe Leu Glu Gly Phe Val Arg
            260                 265                 270

Thr Ser Asn Ile Lys Phe Gln Asp Ala Tyr Asn Ala Gly Gly His Asn
        275                 280                 285

Gly Val Phe Asp Phe Pro Asp Ser Gly Thr His Ser Trp Glu Tyr Trp
    290                 295                 300

Gly Ala Gln Leu Asn Ala Met Lys Pro Asp Leu Gln Arg His Trp Val
305                 310                 315                 320

Pro Arg Pro Thr Pro Gly Pro Pro Gln Gly Ala Phe Asp Phe Pro Asp
                325                 330                 335
```

```
Ser Gly Thr His Ser Trp Glu Tyr Trp Gly Ala Gln Leu Asn Ala Met
                340                 345                 350

Lys Pro Asp Leu Gln Arg His Trp Val Pro Arg Pro Thr Pro Gly Pro
        355                 360                 365

Pro Gln Gly Ala
    370

<210> SEQ ID NO 66
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Asn Leu Phe Ile Ala Pro Trp Gly Val Ile His His Pro His Tyr
1               5                   10                  15

Glu Glu Cys Ser Cys Tyr
            20

<210> SEQ ID NO 67
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Trp Gly Val Ile His His Pro Gly Asn Leu Phe Ile Ala Pro His Tyr
1               5                   10                  15

Glu Glu Cys Ser Cys Tyr
            20

<210> SEQ ID NO 68
<211> LENGTH: 294
<212> TYPE: PRT
<213> ORGANISM: Mycobacterium tuberculosis

<400> SEQUENCE: 68

Ser Arg Pro Gly Leu Pro Val Glu Tyr Leu Gln Val Pro Ser Pro Ser
1               5                   10                  15

Met Gly Arg Asp Ile Lys Val Gln Phe Gln Ser Gly Gly Ala Asn Ser
            20                  25                  30

Pro Ala Leu Tyr Leu Leu Asp Gly Leu Arg Ala Gln Asp Asp Phe Ser
        35                  40                  45

Gly Trp Asp Ile Asn Thr Pro Ala Phe Glu Trp Tyr Asp Gln Ser Gly
    50                  55                  60

Leu Ser Val Val Met Pro Val Gly Gly Gln Ser Ser Phe Tyr Ser Asp
65                  70                  75                  80

Trp Tyr Gln Pro Ala Cys Gly Lys Ala Gly Cys Gln Thr Tyr Lys Trp
                85                  90                  95

Glu Thr Phe Leu Thr Ser Glu Leu Pro Gly Trp Leu Gln Ala Asn Arg
            100                 105                 110

His Val Lys Pro Thr Gly Ser Ala Val Val Gly Leu Ser Met Ala Ala
        115                 120                 125

Ser Ser Ala Leu Thr Leu Ala Ile Tyr His Pro Gln Gln Phe Val Tyr
    130                 135                 140
```

Ala Gly Ala Met Ser Gly Leu Leu Asp Pro Ser Gln Ala Met Gly Pro
145                 150                 155                 160

Thr Leu Ile Gly Leu Ala Met Gly Asp Ala Gly Gly Tyr Lys Ala Ser
            165                 170                 175

Asp Met Trp Gly Pro Lys Glu Asp Pro Ala Trp Gln Arg Asn Asp Pro
            180                 185                 190

Leu Leu Asn Val Gly Lys Leu Ile Ala Asn Asn Thr Arg Val Trp Val
            195                 200                 205

Tyr Cys Gly Asn Gly Lys Pro Ser Asp Leu Gly Asn Asn Leu Pro
    210                 215                 220

Ala Lys Phe Leu Glu Gly Phe Val Arg Thr Ser Asn Ile Lys Phe Gln
225                 230                 235                 240

Asp Ala Tyr Asn Ala Gly Gly His Asn Gly Val Phe Asp Phe Pro
                245                 250                 255

Asp Ser Gly Thr His Ser Trp Glu Tyr Trp Gly Ala Gln Leu Asn Ala
            260                 265                 270

Met Lys Pro Asp Leu Gln Arg Ala Leu Gly Ala Thr Pro Asn Thr Gly
            275                 280                 285

Pro Ala Pro Gln Gly Ala
    290

<210> SEQ ID NO 69
<211> LENGTH: 882
<212> TYPE: DNA
<213> ORGANISM: Mycobacterium tuberculosis

<400> SEQUENCE: 69
tcccggccgg gcttgccggt ggagtacctg caggtgccgt cgccgtcgat gggccgtgac      60
atcaaggtcc aattccaaag tggtggtgcc aactcgcccg ccctgtacct gctcgacggc     120
ctgcgcgcgc aggacgactt cagcggctgg acatcaaca ccccggcgtt cgagtggtac      180
gaccagtcgg gcctgtcggt ggtcatgccg gtgggtggcc agtcaagctt ctactccgac    240
tggtaccagc ccgcctgcgg caaggccggt tgccagactt acaagtggga gaccttcctg    300
accagcgagc tgccggggtg gctgcaggcc aacaggcacg tcaagcccac cggaagcgcc    360
gtcgtcggtc tttcgatggc tgcttcttcg gcgctgacgc tggcgatcta tcaccccag     420 cagttcgtct acgcgggagc gatgtcgggc ctgttggacc cctcccaggc gatgggtccc    480
accctgatcg gcctggcgat gggtgacgct ggcggctaca aggcctccga catgtggggc    540
ccgaaggagg accggcgtg gcagcgcaac gaccgctgt tgaacgtcgg gaagctgatc      600
gccaacaaca cccgcgtctg ggtgtactgc ggcaacggca gccgtcgga tctgggtggc     660 aacaacctgc cggccaagtt cctcgagggc ttcgtgcgga ccagcaacat caagttccaa    720
gacgcctaca cgccggtgg cggccacaac ggcgtgttcg acttcccgga cagcggtacg    780
cacagctggg agtactgggg cgcgcagctc aacgctatga gcccgacct gcaacgggca    840 ctgggtgcca cgcccaacac cgggcccgcg ccccagggcg cc                      882

<210> SEQ ID NO 70
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Ser Glu Phe Ala Tyr Gly Ser Phe Val Arg Thr Val Ser Leu Pro Val
1               5                   10                  15

Gly Ala Asp Glu Gly Asn Leu Phe Ile Ala Pro Trp Gly Val Ile His
            20                  25                  30

His Pro His Tyr Glu Glu Cys Ser Cys Tyr Ser Arg Pro Gly Leu Pro
        35                  40                  45

Val Glu Tyr Leu Gln Val Pro Ser Pro Ser Met Gly Arg Asp Ile Lys
    50                  55                  60

Val Gln Phe Gln Ser Gly Gly Ala Asn Ser Pro Ala Leu Tyr Leu Leu
65                  70                  75                  80

Asp Gly Leu Arg Ala Gln Asp Asp Phe Ser Gly Trp Asp Ile Asn Thr
                85                  90                  95

Pro Ala Phe Glu Trp Tyr Asp Gln Ser Gly Leu Ser Val Val Met Pro
            100                 105                 110

Val Gly Gly Gln Ser Ser Phe Tyr Ser Asp Trp Tyr Gln Pro Ala Cys
        115                 120                 125

Gly Lys Ala Gly Cys Gln Thr Tyr Lys Trp Glu Thr Phe Leu Thr Ser
    130                 135                 140

Glu Leu Pro Gly Trp Leu Gln Ala Asn Arg His Val Lys Pro Thr Gly
145                 150                 155                 160

Ser Ala Val Val Gly Leu Ser Met Ala Ala Ser Ser Ala Leu Thr Leu
                165                 170                 175

Ala Ile Tyr His Pro Gln Gln Phe Val Tyr Ala Gly Ala Met Ser Gly
            180                 185                 190

Leu Leu Asp Pro Ser Gln Ala Met Gly Pro Thr Leu Ile Gly Leu Ala
        195                 200                 205

Met Gly Asp Ala Gly Gly Tyr Lys Ala Ser Asp Met Trp Gly Pro Lys
    210                 215                 220

Glu Asp Pro Ala Trp Gln Arg Asn Asp Pro Leu Leu Asn Val Gly Lys
225                 230                 235                 240

Leu Ile Ala Asn Asn Thr Arg Val Trp Val Tyr Cys Gly Asn Gly Lys
                245                 250                 255

Pro Ser Asp Leu Gly Gly Asn Asn Leu Pro Ala Lys Phe Leu Glu Gly
            260                 265                 270

Phe Val Arg Thr Ser Asn Ile Lys Phe Gln Asp Ala Tyr Asn Ala Gly
        275                 280                 285

Gly Gly His Asn Gly Val Phe Asp Phe Pro Asp Ser Gly Thr His Ser
    290                 295                 300

Trp Glu Tyr Trp Gly Ala Gln Leu Asn Ala Met Lys Pro Asp Leu Gln
305                 310                 315                 320

Arg Ala Leu Gly Ala Thr Pro Asn Thr Gly Pro Ala Pro Gln Gly Ala
                325                 330                 335
```

<210> SEQ ID NO 71
<211> LENGTH: 1038
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
tttgggccca ttatgtcgga attcgcgtac ggttccttcg ttcgcacggt gtcgctgccg      60
gtaggtgctg acgaggggaa tctattcatt gctccttggg gggttattca ccacccgcat     120
```

```
tatgaggaat gttcctgtta ctcccggccg ggcttgccgg tggagtacct gcaggtgccg    180
tcgccgtcga tgggccgtga catcaaggtc caattccaaa gtggtggtgc caactcgccc    240
gccctgtacc tgctcgacgg cctgcgcgcg caggacgact tcagcggctg ggacatcaac    300
accccggcgt cgagtggta cgaccagtcg ggcctgtcgg tggtcatgcc ggtgggtggc    360
cagtcaagct tctactccga ctggtaccag cccgcctgcg gcaaggccgg ttgccagact    420
tacaagtggg agaccttcct gaccagcgag ctgccggggt ggctgcaggc caacaggcac    480
gtcaagccca ccggaagcgc cgtcgtcggt ctttcgatgg ctgcttcttc ggcgctgacg    540
ctggcgatct atcaccccca gcagttcgtc tacgcgggag cgatgtcggg cctgttggac    600
ccctcccagg cgatgggtcc caccctgatc ggcctggcga tgggtgacgc tggcggctac    660
aaggcctccg acatgtgggg cccgaaggag gaccccgcgc ggcagcgcaa cgacccgctg    720
ttgaacgtcg ggaagctgat cgccaacaac accccgcgtct gggtgtactg cggcaacggc    780
aagccgtcgg atctgggtgg caacaacctg ccggccaagt tcctcgaggg cttcgtgcgg    840
accagcaaca tcaagttcca agacgcctac aacgccggtg cggccacaa cggcgtgttc    900 gacttcccgg acagcggtac gcacagctgg gagtactggg cgcgcagct caacgctatg    960 aagcccgacc tgcaacgggc actgggtgcc acgcccaaca ccgggcccgc gccccagggc   1020
gcctagtttc ttaagttt                                                 1038

<210> SEQ ID NO 72
<211> LENGTH: 21
<212> TYPE: DNA
<213> ORGANISM: Influenza virus

<400> SEQUENCE: 72
gggaatctat tcattgctcc t                                             21

<210> SEQ ID NO 73
<211> LENGTH: 21
<212> TYPE: DNA
<213> ORGANISM: Influenza virus

<400> SEQUENCE: 73 tgggggtta ttcaccaccc g                                              21

<210> SEQ ID NO 74
<211> LENGTH: 24
<212> TYPE: DNA
<213> ORGANISM: Influenza virus

<400> SEQUENCE: 74
cattatgagg aatgttcctg ttac                                          24

<210> SEQ ID NO 75
<211> LENGTH: 20
<212> TYPE: PRT
<213> ORGANISM: Mycobacterium tuberculosis

<400> SEQUENCE: 75

Ser Glu Phe Ala Tyr Gly Ser Phe Val Arg Thr Val Ser Leu Pro Val
1               5                   10                  15

Gly Ala Asp Glu
            20
```

```
<210> SEQ ID NO 76
<211> LENGTH: 60
<212> TYPE: DNA
<213> ORGANISM: Mycobacterium tuberculosis

<400> SEQUENCE: 76
tcggaattcg cgtacggttc cttcgttcgc acggtgtcgc tgccggtagg tgctgacgag    60

<210> SEQ ID NO 77
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Asn Leu Phe Ile Ala Pro Trp Gly Val Ile His His Pro His Tyr
1               5                  10                  15

Glu Glu Cys Ser Cys Tyr
            20

<210> SEQ ID NO 78
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gggaatctat tcattgctcc ttgggggtt attcaccacc cgcattatga ggaatgttcc     60
tgttac                                                               66

<210> SEQ ID NO 79
<211> LENGTH: 1008
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
tcggaattcg cgtacggttc cttcgttcgc acggtgtcgc tgccggtagg tgctgacgag    60
gggaatctat tcattgctcc ttgggggtt attcaccacc cgcattatga ggaatgttcc    120
tgttactccc ggccgggctt gccggtggag tacctgcagg tgccgtcgcc gtcgatgggc   180
cgtgacatca aggtccaatt ccaaagtggt ggtgccaact cgcccgccct gtacctgctc   240
gacggcctgc gcgcgcagga cgacttcagc ggctgggaca tcaacacccc ggcgttcgag   300
tggtacgacc agtcgggcct gtcggtggtc atgccggtgg gtggccagtc aagcttctac   360
tccgactggt accagcccgc ctgcggcaag gccggttgcc agacttacaa gtgggagacc   420
ttcctgacca gcgagctgcc ggggtggctg caggccaaca ggcacgtcaa gcccaccgga   480
agcgccgtcg tcggtctttc gatggctgct tcttcggcgc tgacgctggc gatctatcac   540
ccccagcagt tcgtctacgc gggagcgatg tcgggcctgt ggacccctc ccaggcgatg    600 ggtcccaccc tgatcggcct ggcgatgggt gacgctggcg gctacaaggc ctccgacatg   660
tggggcccga aggaggaccc ggcgtggcag cgcaacgacc cgctgttgaa cgtcgggaag   720
ctgatcgcca caacacccg cgtctgggtg tactgcggca acggcaagcc gtcggatctg    780
ggtggcaaca acctgccggc caagttcctc gagggcttcg tgcggaccag caacatcaag   840
```

```
ttccaagacg cctacaacgc cggtggcggc cacaacggcg tgttcgactt cccggacagc    900
ggtacgcaca gctgggagta ctggggcgcg cagctcaacg ctatgaagcc cgacctgcaa    960
cgggcactgg gtgccacgcc caacaccggg cccgcgcccc agggcgcc                 1008
```

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Cys Ala Gly Ala Gly Asn Phe Ile Ala Pro
1               5                   10
```

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Cys Ala Gly Ala Gly Asn Leu Ile Ala Pro
1               5                   10
```

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

```
Cys Ala Gly Ala Gly Asn Leu Phe Ile Ala Pro
1               5                   10
```

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

```
Cys Ala Gly Ala Trp Gly Val His His Pro
1               5                   10
```

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

```
Cys Ala Gly Ala Trp Gly Ile His His Pro
1               5                   10
```

```
<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Cys Ala Gly Ala Trp Gly Val Ile His His Pro
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Cys Ala Gly Ala Trp Gly Ile Val His His Pro
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Asn Leu Ile Ala Pro Trp Gly Val Ile His His Pro
1               5                   10

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Cys Ala Gly Ala Gly Asn Leu Ile Ala Pro Trp Gly Val Ile His His
1               5                   10                  15

Pro

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Asn Leu Phe Ile Ala Pro Trp Gly Val Ile His His Pro
1               5                   10

<210> SEQ ID NO 90
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 90

Cys Ala Gly Ala Gly Asn Leu Phe Ile Ala Pro Trp Gly Val Ile His
1               5                   10                  15

His Pro

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

His Tyr Glu Glu Cys Ser Cys Tyr
1               5

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Cys Ala Gly Ala His Tyr Glu Glu Cys Ser Cys Tyr
1               5                   10

<210> SEQ ID NO 93
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Asn Leu Phe Ile Ala Pro Trp Gly Val Ile His His Pro His Tyr
1               5                   10                  15

Glu Glu Cys Ser Cys Tyr
            20

<210> SEQ ID NO 94
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Cys Ala Gly Ala Gly Asn Leu Phe Ile Ala Pro Trp Gly Val Ile His
1               5                   10                  15

His Pro His Tyr Glu Glu Cys Ser Cys Tyr
            20                  25

<210> SEQ ID NO 95
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 95

Gly Asn Leu Phe Ile Ala Pro Trp Gly Val Ile His His Pro Gly Asn
1               5                   10                  15

Leu Phe Ile Ala Pro Trp Gly Val Ile His His Pro
            20                  25

<210> SEQ ID NO 96
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Cys Ala Gly Ala Gly Asn Leu Phe Ile Ala Pro Trp Gly Val Ile His
1               5                   10                  15

His Pro Gly Asn Leu Phe Ile Ala Pro Trp Gly Val Ile His His Pro
            20                  25                  30

<210> SEQ ID NO 97
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

His Tyr Glu Glu Cys Ser Cys Tyr Gly Asn Leu Phe Ile Ala Pro Trp
1               5                   10                  15

Gly Val Ile His His Pro
            20

<210> SEQ ID NO 98
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Asn Leu Phe Ile Ala Pro His Tyr Glu Glu Cys Ser Cys Tyr Trp
1               5                   10                  15

Gly Val Ile His His Pro
            20

<210> SEQ ID NO 99
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Ser Leu Leu Thr Glu Val Glu Thr Pro Ile Arg Asn Glu Trp Gly Leu
1               5                   10                  15

Leu Thr Glu Val Glu Thr Pro Ile Arg Gln Tyr Ile Lys Ala Asn Ser
            20                  25                  30

Lys Phe Ile Gly Ile Thr Glu
        35
```

```
<210> SEQ ID NO 100
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gly Asn Leu Phe Ile Ala Pro Gly Asn Leu Phe Ile Ala Pro Gln Tyr
1               5                   10                  15

Ile Lys Ala Asn Ser Lys Phe Ile Gly Ile Thr Glu Gly Asn Leu Phe
                20                  25                  30

Ile Ala Pro
        35

<210> SEQ ID NO 101
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

His Tyr Glu Glu Cys Ser Cys Tyr Asp Trp Ser Gly Tyr Ser Gly Ser
1               5                   10                  15

Phe Val Gln His Pro Glu Leu Thr Gly Leu His Tyr Glu Glu Cys Ser
                20                  25                  30

Cys Tyr Gln Tyr Ile Lys Ala Asn Ser Lys Phe Ile Gly Ile Thr Glu
            35                  40                  45

<210> SEQ ID NO 102
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Val Thr Arg Glu Pro Tyr Val Ser Cys Asp Pro Lys Ser Cys Ile Asn
1               5                   10                  15

Arg Cys Phe Tyr Val Glu Leu Ile Arg Gly Arg Val Thr Arg Glu Pro
                20                  25                  30

Tyr Val Ser Cys Asp Pro Gln Tyr Ile Lys Ala Asn Ser Lys Phe Ile
            35                  40                  45

Gly Ile Thr Glu
    50

<210> SEQ ID NO 103
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asp Trp Ser Gly Tyr Ser Gly Ser Phe Val Gln His Pro Glu Leu Thr
1               5                   10                  15

Gly Leu
```

```
<210> SEQ ID NO 104
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ile Thr Gly Phe Ala Pro Phe Ser Lys Asp Asn Ser Ile Arg Leu Ser
1               5                   10                  15

Ala Gly Gly Asp Ile Trp Val Thr Arg Glu Pro Tyr Val Ser Cys Asp
            20                  25                  30

Pro

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Lys Ser Cys Ile Asn Arg Cys Phe Tyr Val Glu Leu Ile Arg Gly Arg
1               5                   10                  15

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Asn Leu Phe Ile Ala Pro Arg Tyr Ala Phe Ala
1               5                   10

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Cys Ala Gly Ala Gly Asn Leu Phe Ile Ala Pro Arg Tyr Ala Phe Ala
1               5                   10                  15

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Asn Leu Val Val Pro Arg Tyr Ala Phe Ala
1               5                   10

<210> SEQ ID NO 109
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 109

Cys Ala Gly Ala Gly Asn Leu Val Val Pro Arg Tyr Ala Phe Ala
1               5                   10                  15

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Asn Leu Ile Ala Pro Arg Tyr Ala Phe Ala
1               5                   10

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Cys Ala Gly Ala Gly Asn Leu Ile Ala Pro Arg Tyr Ala Phe Ala
1               5                   10                  15

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Asn Leu Val Val Pro
1               5

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Ala Gly Ala Gly Asn Leu Val Val Pro
1               5                   10

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Phe Val Ile Arg Glu Pro Phe Ile Ser Cys Ser His Leu Glu Cys
1               5                   10                  15
```

```
-continued

<210> SEQ ID NO 115
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Cys Ala Gly Ala Phe Val Ile Arg Glu Pro Phe Ile Ser Cys Ser His
1               5                   10                  15

Leu Glu Cys

<210> SEQ ID NO 116
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Cys Ala Gly Ala
1
```

METHODS OF TREATING AND PREVENTING INFLUENZA INFECTIONS

REFERENCE TO RELATED APPLICATIONS

This Application is a Continuation U.S. application Ser. No. 15/447,972 filed Mar. 2, 2017, which is a Continuation-in-Part of U.S. application Ser. No. 15/205,476 filed Jul. 8, 2016, which issued as U.S. Pat. No. 9,777,045 on Oct. 3, 2017, which is a Continuation of U.S. application Ser. No. 14/473,605 filed Aug. 29, 2014, which issued as U.S. Pat. No. 9,388,220 Jul. 12, 2016, which is a Continuation of U.S. application Ser. No. 12/199,729 filed Aug. 27, 2008, which issued as U.S. Pat. No. 8,821,885 Sep. 2, 2014, and claims priority to U.S. Provisional Application No. 60/968,145 filed Aug. 27, 2007, and a Continuation of U.S. application Ser. No. 13/750,771 filed Jan. 25, 2013 which issued as U.S. Pat. No. 9,598,462 Mar. 21, 2017, and claims priority to U.S. Provisional Application No. 61/591,113 filed Jan. 26, 2012, each of which is entirely incorporated by reference.

SEQUENCE LISTING

The instant application contains a Sequence Listing which has been submitted electronically in ASCII format and is hereby incorporated by reference in its entirety. Said ASCII copy, created on Sep. 30, 2019, is named 3022_015_USCP02_SL.txt and is 39,850 bytes in size.

BACKGROUND

1 Field of the Invention

The present invention is directed to composite antigens composed of a plurality of epitopes, and to tools and methods for generating an immune response with the composite antigens of the invention. The invention is also directed to compositions comprising composite antigenic sequences derived from multiple pathogens for the development of novel vaccines and to the vaccines developed.

2 Description of the Background

Microbial and viral pathogens are a primary source of infectious disease in animals. Pathogens and their hosts constantly adapt to one another in an endless competition for survival and propagation. Certain pathogens have become enormously successful at infecting mammalian hosts and surviving exposure to the host immune response, even over periods of years or decades. One example of an extremely successful mammalian pathogen is the influenza virus.

Influenza viruses are etiologic agents for a contagious respiratory illness (commonly referred to as the flu) that primarily affects humans and other vertebrates. Influenza is highly infectious and an acute respiratory disease that has plagued the human race since ancient times. Infection is characterized by recurrent annual epidemics and periodic major worldwide pandemics. Influenza virus infection can cause mild to severe illness, and can even lead to death. Every year in the United States, 5 to 20 percent of the population, on average, contracts the flu with more than 200,000 hospitalizations from complications and over 36,000 deaths. Because of the high disease-related morbidity and mortality, direct and indirect social economic impacts of influenza are enormous. Four pandemics occurred in the last century, together causing tens of millions of deaths worldwide.

Influenza virus spreads from host to host through coughing or sneezing. Airborne droplets are the primary transmission vectors between individuals. In humans, the virus typically spreads directly from person to person, although persons can also be infected from indirect contact with surfaces harboring the virus. Infected adults become infectious to others beginning as little as one day before primary symptoms of the disease develop. Thereafter, these persons remain infectious for up to 5 days or more after. Uncomplicated influenza illness is often characterized by an abrupt onset of constitutional and respiratory symptoms, including fever, myalgia, headache, malaise, nonproductive cough, sore throat, rhinitis, or a combination of one or more of these symptoms.

Currently, the spread of pathogenic influenza virus is controlled in animal populations by vaccination and/or treatment with one or more anti-viral compounds. Vaccines containing inactivated influenza virus or simply influenza antigen are currently in use worldwide and especially promoted for use by high-risk groups such as infants, the elderly, those without adequate health care and immunocompromised individuals. Most all viruses for vaccine use are propagated in fertile hen's eggs, inactivated by chemical means, and the antigens purified. The vaccines are usually trivalent, containing representative influenza A viruses (H1N1 and H3N2) and influenza B strains. The World Health Organization (WHO) regularly updates the specific strains targeted for vaccine development to those believed to be most prevalent and thereby maximize overall world efficacy. During inter-pandemic periods, it typically takes eight months or more before an updated influenza vaccine is ready for market. Historically, viral pandemics are spread to most continents within four to six months, and future viral pandemics are likely to spread even faster due to increased international travel. It is likely inevitable that an effective vaccine made by conventional means will be unavailable or in very short supply during the first wave of any future widespread outbreak or pandemic.

Pandemic flu can and does arise at any time. Although the severity of the next Influenza pandemic cannot be accurately predicted, modeling studies suggest that the impact of a pandemic on the United States, and the world as a whole, would be substantial. In the absence of any control measures (vaccination or drugs), it has been estimated that in the United States a "medium-level" pandemic could cause: 89,000 to 207,000 deaths; 314,000 and 734,000 hospitalizations; 18 to 42 million outpatient visits; and another 20 to 47 million people being sick. According to the Centers for Disease Control and Prevention (CDC) (Atlanta, Ga., USA), between 15 percent and 35 percent of the U.S. population could be affected by an influenza pandemic, and the economic impact could range between approximately $71 and $167 billion.

Vaccines capable of producing a protective immune response have been produced in the last half century. These include whole virus vaccines, split-virus vaccines, and surface-antigen vaccines and live attenuated virus vaccines. While formulations of any of these vaccine types are capable of producing a systemic immune response, live attenuated virus vaccines have the advantage of also being able to stimulate local mucosal immunity in the respiratory tract.

With the continual emergence (or re-emergence) of different influenza strains, new influenza vaccines are continually being developed. Because of the rapid mutation rate among Influenza viruses, it has been extremely difficult and at times not possible to identify the antigenic moieties of the emergent virus strains in sufficient time to develop a suitable vaccine. Thus, polypeptides and polynucleotides of newly emergent or re-emergent virus strains (especially sequences of antigenic genes) are highly desirable.

Influenza is typically caused by infection of two genera of influenza viruses: Influenzavirus A and Influenzavirus B. The third genus of influenza viruses, Influenzavirus C, exists as a single species, influenza C virus, which causes only minor common cold-like symptoms in susceptible mammals. Infections by influenza A virus and influenza B virus are typically initiated at the mucosal surface of the upper respiratory tract of susceptible mammals. Viral replication is primarily limited to the upper respiratory tract but can extend to the lower respiratory tract and cause bronchopneumonia that can be fatal.

Influenza A virus, in particular, has many different serotypes. Presently, there are sixteen known variations of HA (the hemaglutination antigen which is involved in virus to cell binding) and nine known variations of NA (the neuraminidase antigen which is involved in viral release) within influenza A viruses, thus yielding 144 possible "HN" serotypes of influenza A virus based on variations within these two proteins alone. Only a small number of these combinations are believed to be circulating within susceptible populations at any given time. Once a new influenza strain or serotype emerges and spreads, the historical pattern is that it becomes established within the susceptible population and then moves around or "circulates" for many years causing seasonal epidemics of the Flu. Three genera of influenza viruses currently comprise the Orthomyxoviridae Family:

Influenza virus A, Influenza virus B, and Influenza virus C. Each of these genera contains a single species of influenza virus: The genus Influenza virus A consists of a single species, influenza A virus, which includes all of the influenza virus strains currently circulating among humans, including, for example, but not limited to, H1N1, H1N2, H2N2, H3N1, H3N2, H3N8, H5N1, H5N2, H5N3, H5N8, H5N9, H7N1, H7N2, H7N3, H7N4, H7N7, H9N2, and H10N7 serotypes. Exemplary influenza A viral strains include, but are not limited to, A/Aichi/2/68, A/Alaska/6/77, A/Alice, A/Ann Arbor/6/60, A/Bayern/7/95, A/Beijing/352/89, A/Beijing/353/89, A/Bethesda/1/85, A/California/10/78, A/Chick/Germany/N/49, A/Chile/1/83, A/Denver/1/57, A/Dunedin/6/83, A/Equine/Miami/1/63, A/FM/1/47, A/Great Lakes/0389/65, A/Guizhou/54/89, A/Hong Kong/77, A/Hong Kong/8/68, A/Hong Kong/483/97, A/Johannesburg/33/94, A/Kawasaki/9/86, A/Kiev/59/79, A/Korea/1/82, A/Korea/426/68, A/Leningrad/13/57, A/Los Angeles/2/87, A/MaI/302/54, A/Memphis/8/88, A/Nanchang/933/95, A/New Jersey/8/76, A/NT/60/68, A/NWS/33, A/Peking/2/79, A/Port Chalmers/1/73, A/PR/8/34, A/Shanghai/11/87, A/Shanghai/16/89, A/Shanghai/31/80, A/Singapore/1/57, A/Singapore/6/86, A/South Carolina/1/181918, A/Swine/1976/31, A/Swine/Iowa/15/30, A/Swine/New Jersey/8/76, A/Sydney/5/97, A/Taiwan/1/86, A/Taiwan/1/86A1, A/Texas/35/91, A/Texas/36/91, A/USSR/90/77, A/Victoria/3/75, A/Vietnam/1203/04, A/Washington D.C./897/80, A/Weiss/43, A/WS/33, A/WSN/33, A/Wuhan/359/95, A/Wyoming/1/87, and A/Yamagata/32/89, as well as derivatives, variants, and homologs thereof.

The genus Influenza virus B consists of a single species, influenza B virus, of which there is currently only one known serotype. Influenza B virus is almost exclusively a human pathogen, but is significantly less common and less genetically diverse than influenza A strains. Because of this limited genetic diversity, most humans acquire a certain degree of immunity to influenza B virus at an early age; however, the mutation frequency of the virus is sufficiently high enough to prevent lasting immunity by most humans, but not high enough to permit pandemic infection by influenza B virus across human populations. Exemplary influenza B viral serotypes include, but are not limited to, B/Allen/45, B/Ann Arbor/1/86, B/Bangkok/163/90, B/Beijing/184/93, B/Brigit, B/GL/1739/54, B/Hong Kong/330/2001, B/Hong Kong/5/72, B/Lee/40, B/Maryland/1/59, B/Mass/3/66, B/Oman/16296/2001, B/Panama/45/90, B/R22 Barbara, B/R5, B/R75, B/Russia/69, B/Shandong/7/97, B/Sichuan/379/99, B/Taiwan/2/62, B/Tecumseh/63/80, B/Texas/1/84, B/Victoria/2/87, and B/Yamagata/16/88, as well as derivatives, variants, and homologs thereof.

The genus Influenza virus C also consists of a single species, denoted influenza C virus, of which there is also currently only one known serotype. This serotype is known to infect both primates and porcines, and while infections of influenza C virus are rare, the resulting illness can be severe. Epidemics of influenza C virus are not uncommon in exposed populations, however, due to its rapid transmissibility in humans having close contact.

Polynucleotide and polypeptide sequences from each of these strains are contained within the publicly-available databases of the National Center for Biotechnology Information (National Library of Medicine, National Institutes of Health, Bethesda, Md., USA), and viral stocks may be obtained from the American Type Culture Collection (Manassas, Va., USA), or are otherwise publicly available.

Human influenza virus usually refers to influenza virus serotypes that are transmissible among humans. There are only three known influenza A virus HN serotypes that have circulated widely among humans in recent times: H1N1, H2N2, and H3N2. Many humans have acquired at least some level of immunity to these subtypes. All Influenza viruses, however, are known to mutate and change frequently. Influenza viruses are known to infect waterfowl and swine and to circulate among those hosts forming a breeding ground for new subtypes and strains separate from human populations. Because many serotypes (and particularly newly-arising subtypes) have a zero or low prevalence in human populations, there is little or no natural immunity against them in human populations. Such a population is referred to as being "naïve" to such serotypes. Accordingly, Influenza viruses might be expected to adapt over time to generate one or more highly virulent strains that will infect and spread catastrophically among naïve humans, as has been widely reported in the mainstream press.

The highly-virulent influenza H5N1 subtype (publicly referred to as the bird flu virus), for example, has been reported as having mutated sufficiently to become transmissible from avian hosts to humans. As this subtype has been limited to infecting avian populations in the past, there is little or no legacy of infection to have generated immunity within the human population. Thus, the human population is expected to be highly susceptible to H5N1.

To date, the H5N1 serotype does not appear to have mutated sufficiently to become efficiently transmitted from human to human. Nonetheless, because influenza viruses are constantly adapting, there is concern that H5N1 virus or another virulent influenza strain or serotype will arise that will be able to infect humans and spread easily from one person to another. It has been commonly suggested that if H5N1 virus were to gain the capacity to spread easily from person to person, a worldwide outbreak of disease (i.e., pandemic) would likely begin, resulting in millions of deaths.

Annual influenza outbreaks occur as a result of "antigenic drift." Antigenic drift is caused by mutations within antigenic (i.e., immunity stimulating) portions of viral proteins within viral subtypes circulating in host populations that alter the host's ability to recognize and defend effectively against the infecting virus, even when the virus has been circulating in the community for several years. The antigenic drift that diminishes existing immunity in a host population generally occurs within so-called immunodominant antigens or regions. Immunodominant antigens are those antigens belonging to a pathogen that are the most-easily and most-quickly recognized by the host immune system and, consequently, account for the vast majority of immune response to the invading pathogen. Typically, immunodominant antigens exist within regions of the pathogen that are most exposed to the environment, i.e., are on the external surfaces or on protruding elements of the pathogen, and so are most readily accessible to the host immune system.

In the case of influenza, the immunodominant HA and NA proteins protrude from the central capsid of the viral particle, and so they tend to interact most strongly with the host's internal environment and dominate the host immune response. Mutations occurring in the microbial genome that protect the microbe from the host immune system, these mutations are most readily found to affect the immunodominant antigens.

Conversely, non-immunodominant antigens are those that are capable of raising a host immune response but account for only a small amount of the total immune response. This is thought to happen because the non-immunodominant antigens are at least partially shielded from the host immune system, as in the case of an antigen that is located in a cleft or fold of the microbial surface or is surrounded by protruding elements of the microbe. In the case of influenza, non-immunodominant antigens occurring near the capsid surface are shielded from the host immune system by the immunodominant HA and NA spikes protruding from the surface. Non-immunodominant antigens tend to show less mutation in response to host immune pressure than do immunodominant antigens.

Antigenic shift occurs when there is an abrupt or sudden, major change in a virus. Antigenic shift is typically caused by the occurrence of new combinations of the HA and/or NA proteins on the surface of the virus, i.e., the creation of a new Influenza subtype. The appearance of a new influenza A virus subtype, to which most of the world's population is naïve, is the first step toward a pandemic. If the new Influenza subtype also has the capacity to spread easily from person to person, then a full-blown pandemic may be expected resulting in a global influenza outbreak infecting millions of humans.

The CDC and the leading authorities on disease prevention in the world recommend the single best way of preventing the flu is through annual vaccination. Conventional vaccines however, typically target the HA and NA antigens, and have been neither universally protective nor 100 percent effective at preventing the disease. Antigenic shift prevents flu vaccines from being universally protective or from maintaining effectiveness over many years. The ineffectiveness of conventional vaccines may also be due, in part, to antigenic drift and the resulting variation within antigenic portions of the HA and NA proteins most commonly recognized by the immune system (i.e., immunodominant antigens). As a result, many humans may find themselves susceptible to the flu virus without an effective method of treatment available since influenza is constantly improving its resistant to current treatments. This scenario is particularly concerning with respect to the H5N1 virus, which is highly virulent but for which there is currently no widely available commercial vaccine to immunize susceptible human populations.

Currently, flu vaccines are reformulated each year due to the yearly emergence of new strains, and generally induce limited immunity. In addition, to achieve a protective immune response, some vaccines are administered with high doses of antigen. This is particularly true for H5N1 vaccines. In addition, influenza vaccines, including H5N1 vaccines, typically present epitopes in the same order as the epitopes are found in nature, generally presenting as whole-viral proteins; consequently, relatively large amounts of protein are required to make an effective vaccine. As a result, each administration includes an increased cost associated with the dose amount, and there is increased difficulty in manufacturing enough doses to vaccinate the general public. Further, the use of larger proteins elevates the risk of undesirable immune responses in the recipient host.

Accordingly, it would be advantageous to administer a vaccine that provides protection against an infection over a broad range of different strains and/or variations of a pathogen, and a vaccine that is effective against multiple pathogens. It would also be advantageous to administer a single or limited number of vaccinations that would provide effective protection across a selection of different pathogens and a vaccine that could be effective in those individuals with limited immune system function. Such vaccines would be useful to treat many individuals and populations and may be useful to compliment conventional vaccines, all to provide comprehensive protection to as many individuals as possible against existing as well as new and emerging pathogens across a population.

SUMMARY OF THE INVENTION

The present invention provides new and useful compositions, as well as tools and methods for generating an immune response. In particular, the invention provides vaccines and methods developed from multiple antigenic regions of one or more pathogens.

One embodiment of the invention is directed to a composite antigen comprising a peptide with contiguous amino acid sequence derived from a plurality of antigenic epitopes of one or more pathogens that induces an immune response in a mammal that is protective against infection by the one or more pathogens. Preferably the plurality of epitopes contains one or more composite epitopes. Preferably the composite antigen contains a plurality of antigenic epitopes, comprising one or more repetitions of a same epitope, one or more repetitions of different epitopes, one or more repetitions of composite epitopes, or a combination thereof. Also preferably, the amino acid sequence of at least one epitope of the composite antigen does not exist naturally. Composite antigens can be used to treat or preferably prevent infection and disease associated with one or more pathogens including but not limited to viruses, bacteria, parasites, yeast, fungi, or a combination thereof. Preferably the pathogen is an influenza virus and the one or more antigenic epitopes are amino acid sequences of M1, M2, HA, NA, PB1, or PB2 protein, or a combination thereof. Exemplary composite sequences include, but are not limited to, SEQ ID NOs 4, 5, 8, 19, 20, 52, 53, 56 and 54, and SEQ ID NO 16, 65, 66, 67, 70 and 73.

Another embodiment of the invention is directed to composite antigens comprising an amino acid sequence containing amino acids that are in common between sequences of epitopes of multiple conserved regions, and the amino acids that differ between the sequences of epitopes of multiple conserved regions. Preferably, the amino acid sequence has the formula $An1BCAn2$, wherein A represents the amino acids that are in common between sequences of epitopes of multiple conserved regions, B and C represent the amino acids that differ between the sequences of epitopes of multiple conserved regions, wherein A, B, and C are naturally occurring amino acids, N1 and N2 total to less than 25, and the number of B and C amino acids is less than 3. Exemplary composite sequences include, but are not limited to SEQ ID NO. 6, 7, 21, 22, 54, 55, 58 or 59. Preferably the composite antigen contains multiple conserved regions of a peptide sequence derived from multiple serotypes of a same pathogen. Preferably the pathogen is influenza virus.

Another embodiment of the invention is directed to an antibody that is specifically reactive to the composite antigen of the invention.

Another embodiment of the invention is directed to polynucleotides that encode composite antigens of the invention.

Another embodiment of the invention is directed to methods for generating an immune response in a mammal comprising administering to the mammal the composite antigen of the invention. Preferably the immune response generated is protective against a number of different strains, serotypes or species of the one or more pathogens.

Another embodiment of the invention is directed to a vaccine comprising the composite antigen of the invention. Preferably the composite antigen is has the formula An1BCAn2, wherein A represents the amino acids that are in common between sequences of epitopes of multiple conserved regions, B and C represent the amino acids that differ between the sequences of epitopes of multiple conserved regions, wherein A, B, and C are naturally occurring amino acids, N1 and N2 total to less than 25, and the number of B and C amino acids is less than 3.

Other embodiments and advantages of the invention are set forth in part in the description, which follows, and in part, may be obvious from this description, or may be learned from the practice of the invention.

DESCRIPTION OF THE DRAWINGS

FIG. 1 Summary of ELISA antisera titers of peptides (or Pep) 3, 6, 9, 10 and 11 of H3N2 Influenza virus (Wuhan).

FIG. 7 Antisera titers for mice immunized with Pep 11 on H5N1 at various dilutions.

FIG. 8-1 Additional sequences and related information including SEQ ID NO 114.

FIG. 8-2 Additional sequences and related information.

FIG. 8-3 Additional sequences and related information including SEQ ID NO 114.

FIG. 8-4 Additional sequences and related information.

FIG. 8-6 Additional sequences and related information.

DESCRIPTION OF THE INVENTION

Figure 2:
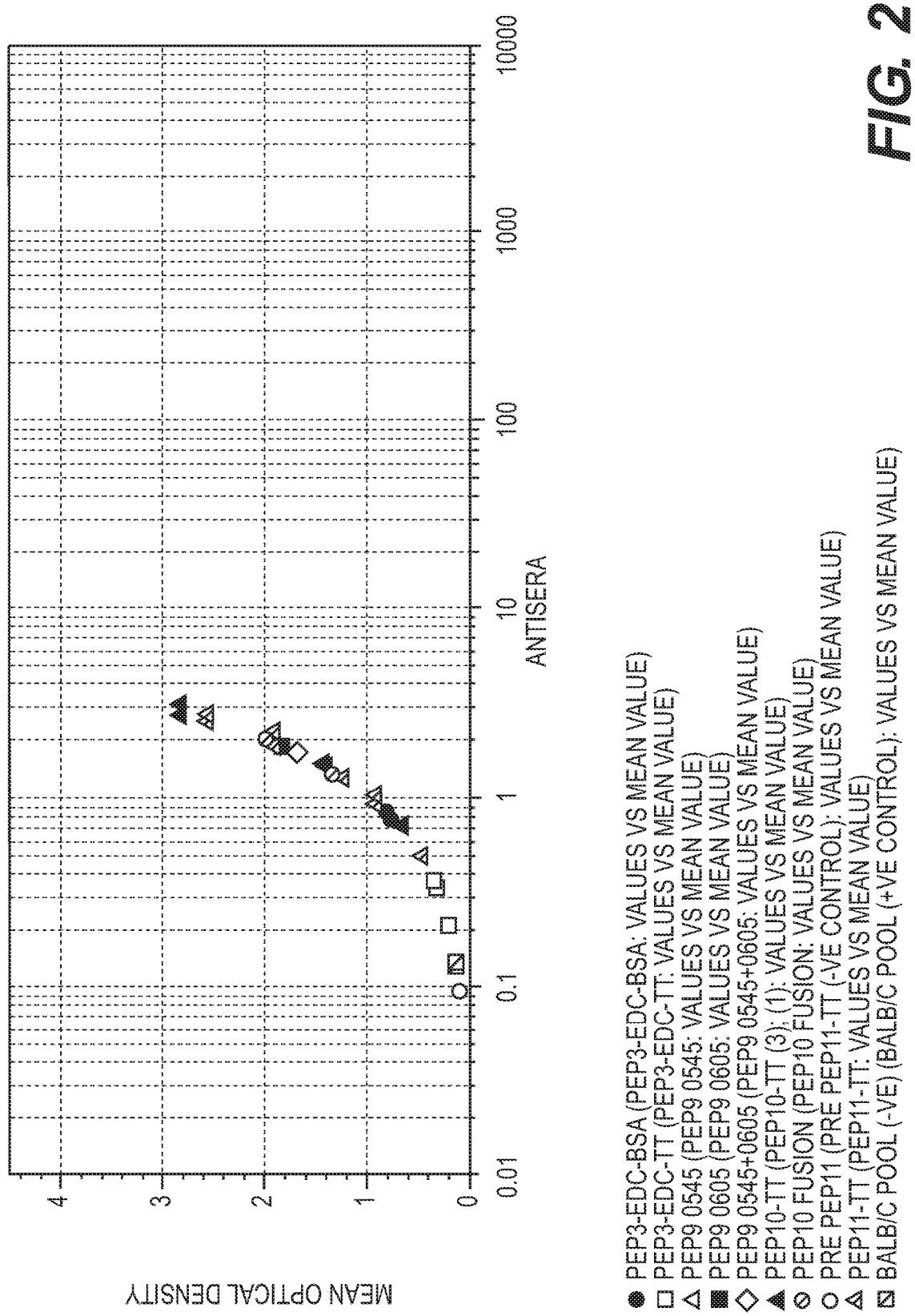
FIG. 2 Antisera mean ODs of mice immunized with different peptides of H3N2 Influenza virus (Wuhan 1:40).
Figure 3:
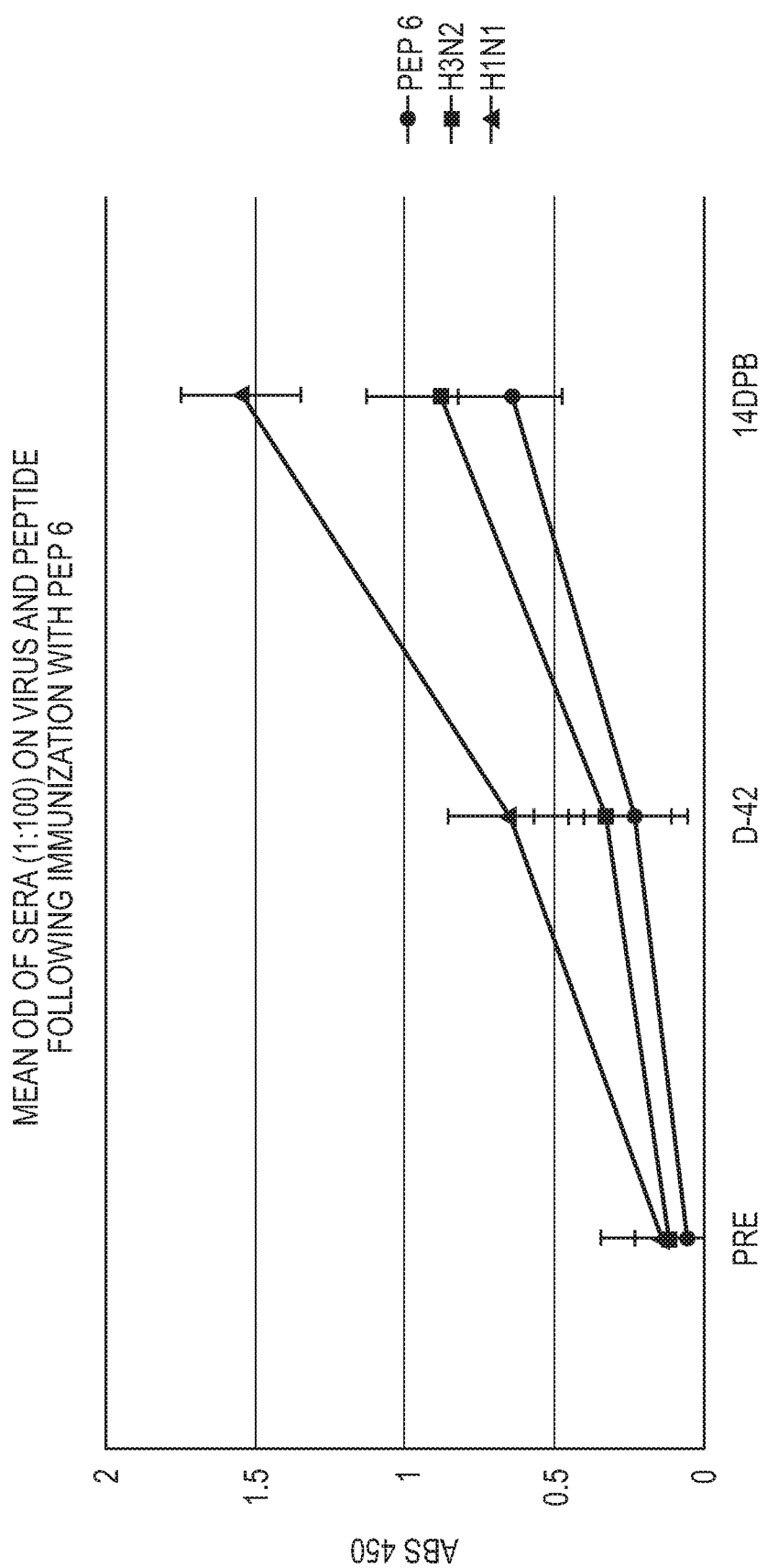
FIG. 3 Mean ODs of antisera (1:100) on virus and peptide following immunization with Pep 6
Figure 4:
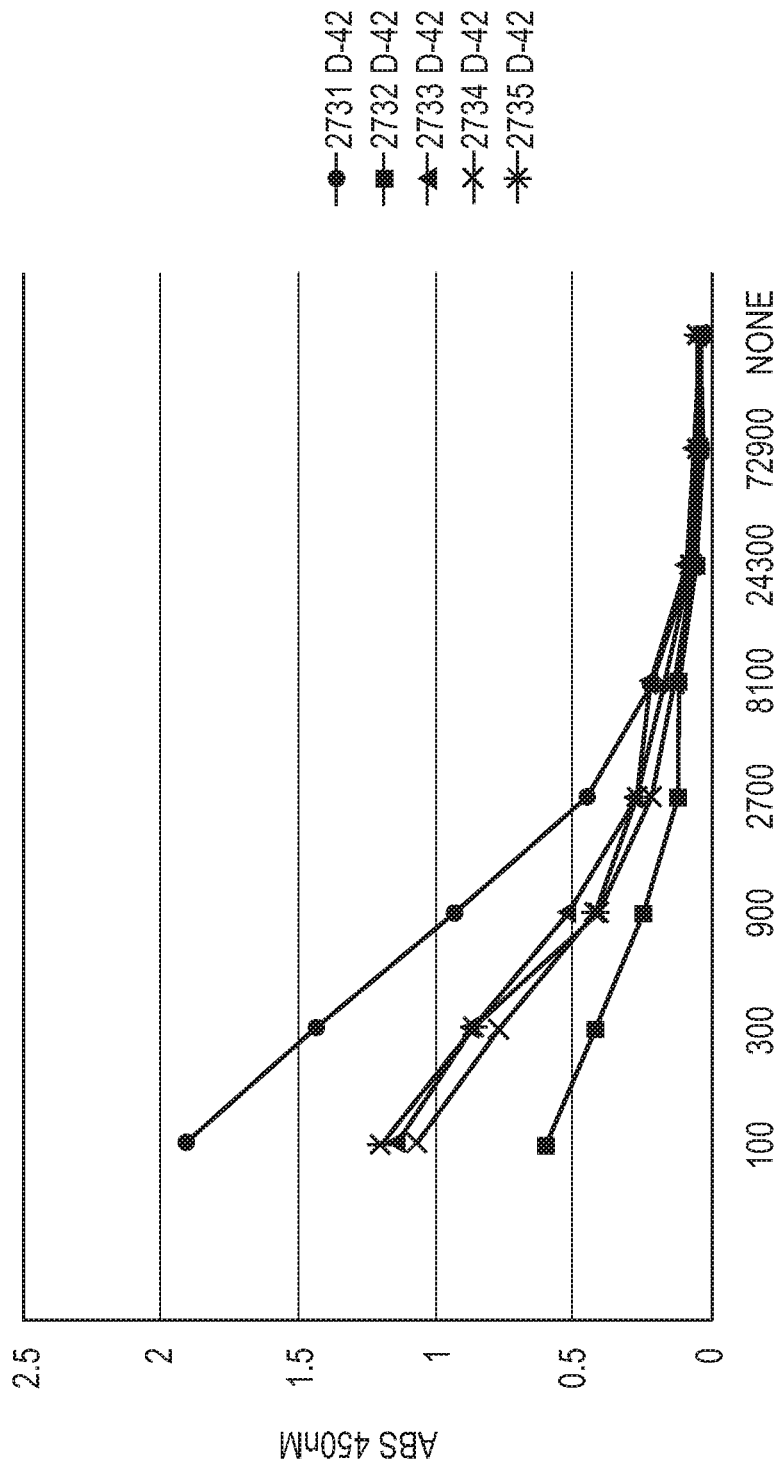
FIG. 4 Antisera titers for mice immunized with Pep 9 on H1N1 (Caledonia) virus at various dilutions.
Figure 5A:
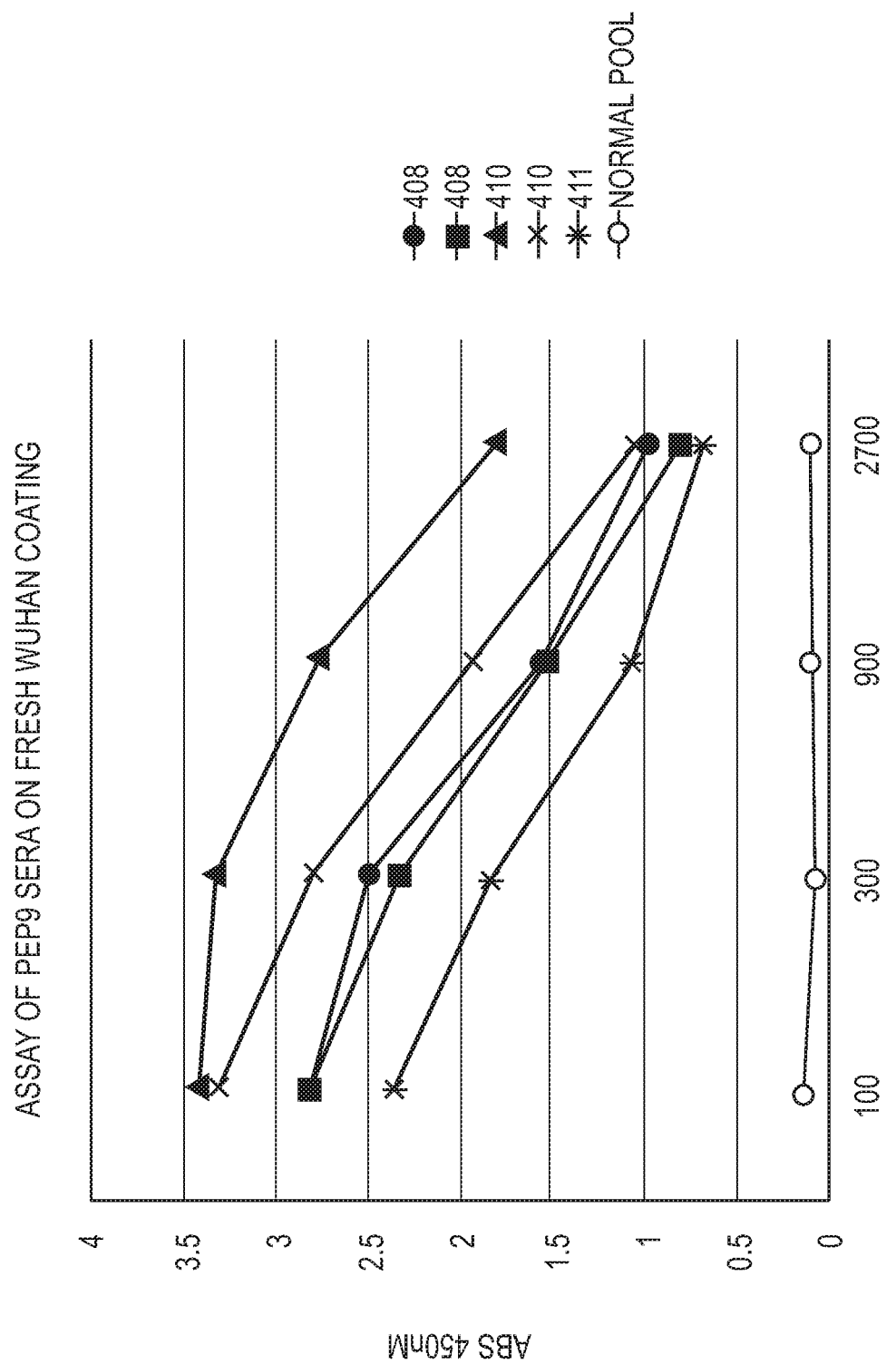
FIG. 5A Assay of Pep 9 sera on fresh Wuhan coating.
Figure 5B:
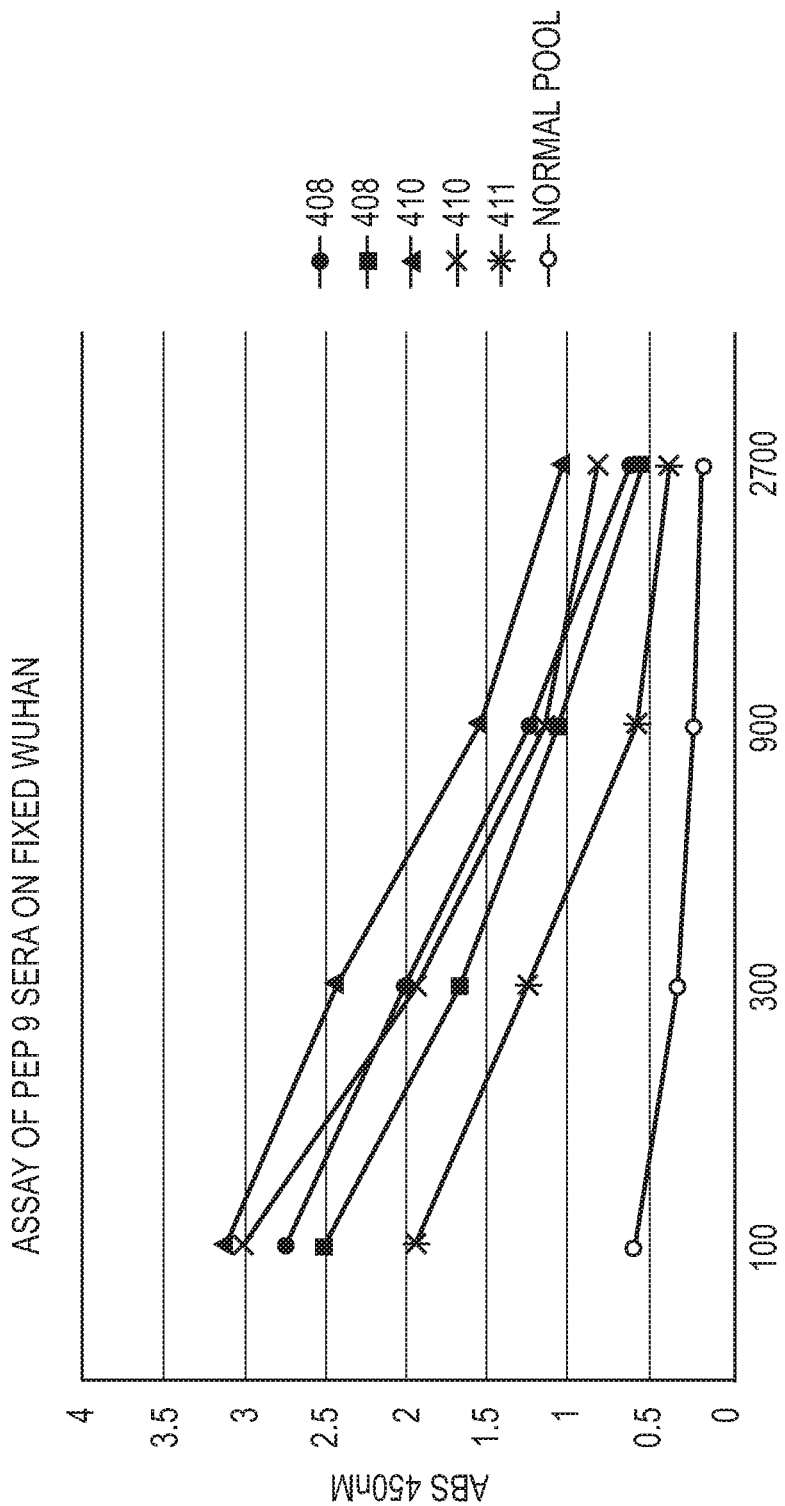
FIG. 5B Assay of Pep 9 sera on fixed Wuhan.
Figure 5C:
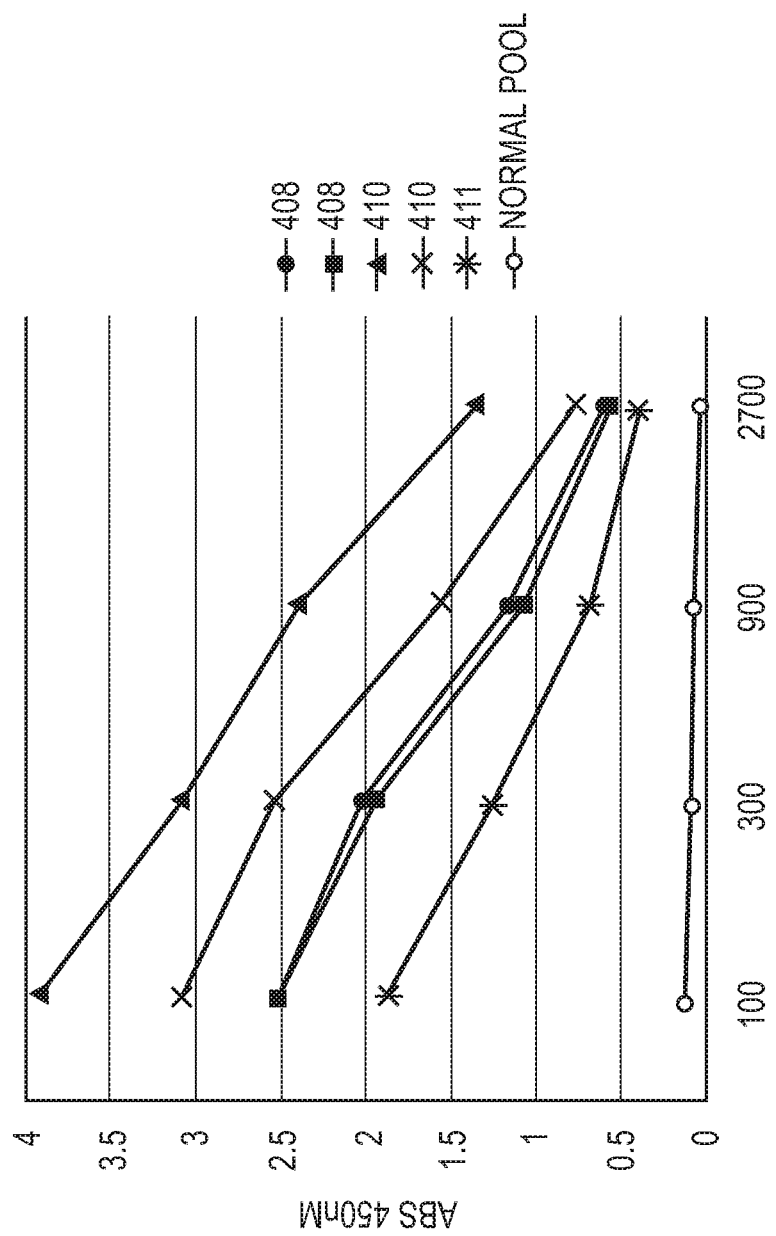
FIG. 5C Assay of Pep 9 sera on fresh Caledonia coating.
Figure 5D:
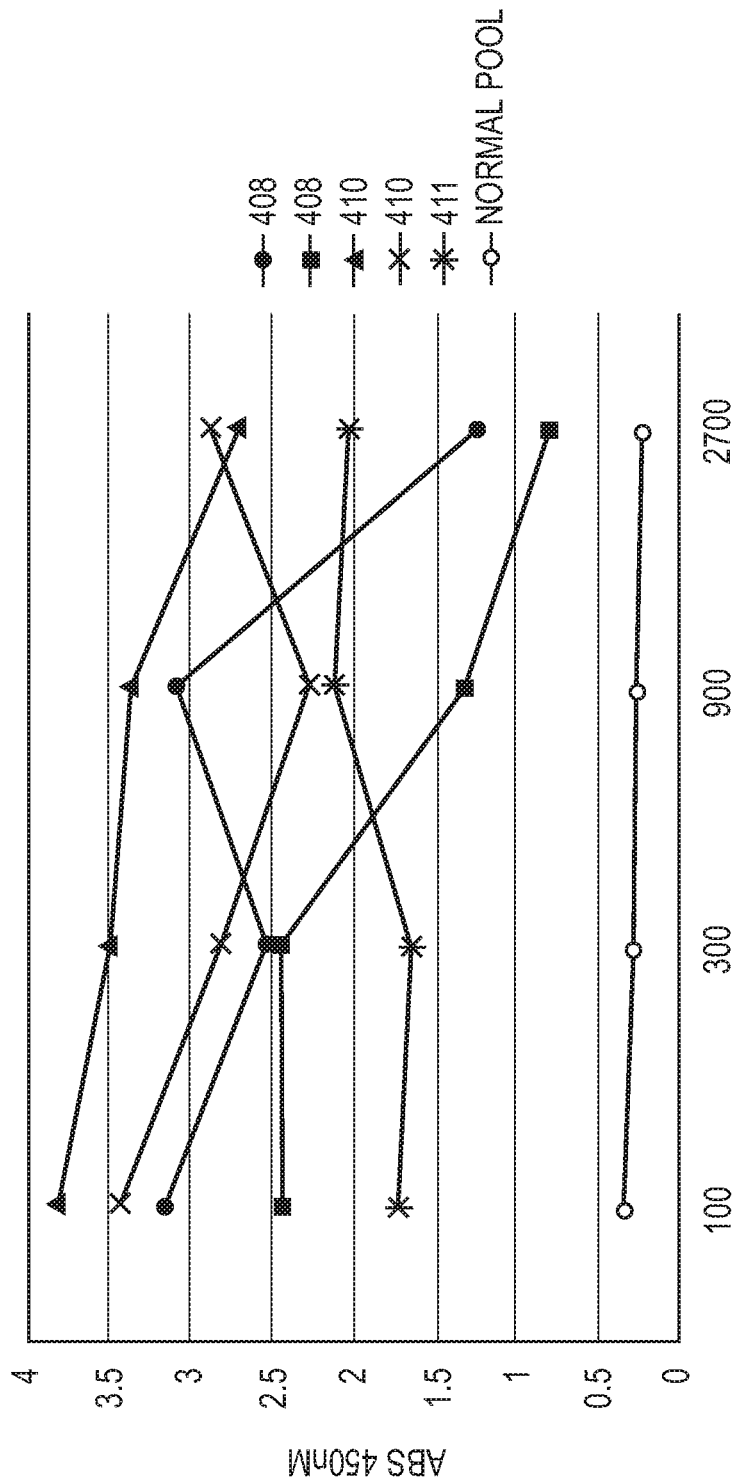
FIG. 5D Assay of Pep 9 sera on fixed Caledonia coating.

Vaccinations and vaccines are often the best mechanism for avoiding an infection and preventing the spread of debilitating and dangerous pathogens. With respect to viral infections and many bacterial infections, vaccinations are often the only effective option as treatment options are few and those that are available provide only limited effectiveness. Conventional vaccinations require a priori understanding or general identification of the existing antigenic regions of the pathogen. The pathogen itself is propagated and a suitable vaccine developed from heat-killed or otherwise attenuated microorganisms. Alternatively, an antigen or collection of antigens is identified that will generate a protective immune response upon administration. The need for a vaccine is especially urgent with respect to preventing infection by certain bacteria and viruses. Many bacteria and especially certain viruses mutate constantly often rendering the vaccine developed to the prior or originating bacteria or virus useless against the new strains that emerge. As a consequence, vaccines against infections are reformulated yearly and often administered at fairly high doses. The manufacturing costs are high and administering vaccines against pose a great many complications and associated risks to patients.

It has been surprisingly discovered that an effective vaccine can be produced from a composite antigen of the invention. Composite antigens are antigens that contains or are derived from a plurality of antigenic regions of a pathogen. Composite antigens of the invention may contain one epitope that represents a combination of conserved regions of two or more epitopes (e.g., the composite epitope as outlined herein), or a plurality of immunologically responsive regions derived from one or multiple sources (e.g., virus particles, parasites, bacteria, fungi, cells). These immunological regions are amino acid sequences or epitopes that are representative of sequences found at those antigenic regions of a pathogen or other antigen associated with an infection or a disease or, importantly, associated with stimulation of the immune system to provide protection against the pathogen.

One embodiment of the invention is directed to composite antigens. Composite antigens of the invention contain non-naturally occurring amino acid sequences that do not exist in nature and are otherwise artificially constructed. Each sequence of a composite antigen contains a plurality of immunologically responsive regions or epitopes of a pathogen, which are artificially arranged, preferably along a single amino acid sequence. The plurality may contain multiples of the same epitope, although not in a naturally occurring order, or multiples of a variety of different epitopes from one or more pathogens. Epitopes may be identical to known immunological regions of a pathogen, or entirely new constructs that have not previously existed and therefore artificially constructed. Preferably, the composite antigen of the invention induces killer T-cell ($T_C$ or CTL) responses, helper T-cell ($T_H$) responses, and specific antibody production in an inoculated mammal.

A "composite" antigen is an engineered, artificially created antigen made from two or more constituent epitopes, such that the resulting composite antigen has physical and/or chemical properties that differ from or are additive of the individual constituent epitopes. Preferable the composite antigen, when exposed to the immune system of a mammal, is capable of simultaneously generating an immunological response to each of the constituent epitope of the composite and preferably to a greater degree (e.g., as measurable from a cellular or humoral response to an identified pathogen) than the individual constituent epitopes. In addition, the composite antigen provides the added function of generating a protective immunological response in a patient when used as a vaccine and against each of the constituent epitopes. Preferably, the composite has the additional function of providing protection against not only the pathogens from which the constituents were derived, but related pathogens as well. These related pathogenic organisms may be strains or serotypes of the same species of organism, or different species of the same genus of organism, or different organisms entirely that are only related by a common epitope.

Another embodiment of the invention is directed to isolated epitopes. Isolated epitopes are regions obtained or derived from a protein or peptide of a pathogen that elicit a robust immunological response when administered to a mammal. Preferably, that robust response provides the mammal with an immunological protection against developing disease from exposure to the pathogen. A preferred example of an isolated epitope is a composite epitope, which is one artificially created from a combination of two or more highly conserved, although not identical, amino acid sequences of two or more different, but otherwise related pathogens. The pathogens may be of the same type, but of a different strain, serotype, or species or other relation. The composite epitope contains the conserved region that is in common between the related epitopes, and also contains the variable regions which differ. The sequences of a composite epitope that represents a combination of two conserved, but not identical sequences, may be illustrated as follows:

Sequence of Epitope 1 . . . AAAAABAAAAA . . .
Sequence of Epitope 2 . . . AAAAACAAAAA . . .
Composite Epitope . . . AAAAABCAAAAA . . .

wherein, "A" represents the amino acids in common between the two highly conserved epitopes, "B" and "C" represent the amino acids that differ, respectively, between two epitopes, each of "A", "B" and "C" can be any amino acid and any number of amino acids. Preferably the conserved region contains about 20 or less amino acids on each side of the variable amino acids, preferably about 15 or less, preferably about 10 or less, preferably about 8 or less, preferably about 6 or less, and more preferably about 4 or less. Preferably the amino acids that vary between two similar but not identical conserved regions are 5 or less, preferably 4 or less, preferably 3 or less, preferably 2 or less, and more preferably only 1.

A "composite epitope," similar to the composite antigen, is an engineered, artificially created single epitope made from two or more constituent epitopes, such that the resulting composite epitope has physical and/or chemical properties that differ from or are additive of the constituent epitopes. Preferable the composite epitope, when exposed to the immune system of a mammal, is capable of simultaneously generating an immunological response to each of the constituent epitopes of the composite and preferably to a greater degree than that achieved by either of the constituent epitopes individually. In addition, the composite epitope provides the added function of generating a protective immunological response in a patient when used as a vaccine and against each of the constituent epitopes. Preferably, the composite has the additional function of providing protection against not only the pathogens from which the constituents were derived, but related pathogens as well. These related pathogenic organisms may be strains or serotypes of the same species of organism, or different species of the same genus of organism, or different organisms entirely that are only related by a common epitope.

Composite epitopes of the invention are entirely artificial molecules that do not otherwise exist in nature and to which an immune system has not been otherwise exposed. Preferably, these conserved immunological regions that are combined as a composite epitope represent immunologically responsive regions of proteins and/or polypeptides that are highly conserved between related pathogens. Although a vaccine can be developed from a single composite epitope, in many instances the most effective vaccine may be developed from multiple, different composite epitopes.

Accordingly, composite antigens of the invention may contain one or more composite epitopes and/or one or more known epitopes to provide an effective vaccine. Although composite antigens may comprise a single composite epitope, a composite antigen would not comprise only a single known epitope. Preferably, the immunological response achieved from a vaccination with a composite antigen, or group of composite antigens, provides protection against infection caused by the original strains from which the sequence of the composite antigen was derived, and also provides immunological protection against other strains, serotypes and/or species that share one or more of the general conserved regions represented in the composite antigen. Thus, the resulting immune response achieved from a vaccination with a composite antigen is more broadly protective than can be achieved from a conventional single antigen vaccination against multiple strains, serotypes, and species or otherwise related pathogens regardless of antigenic drift that may take place in the evolution of the pathogen. Preferably, vaccines developed from composite antigens of the invention avoid any need for repeated or annual vaccinations, the associated complications and expenses of manufacture, and the elevated risks to the patient. These vaccines are useful to treat individuals and populations, thereby preventing infection, mortality and pandemics, and are useful to compliment conventional vaccines.

As discussed herein, the composite antigen preferably comprises a single chain of amino acids with a sequences derived from one or more composite epitopes, one or more composite epitopes plus one or more known epitopes, or a plurality of known epitopes, that may be the same or different. Epitope sequences may be repeated consecutively and uninterrupted along a composite sequence or interspersed among other sequences that may be single or a few amino acids as spacers or sequences that encode peptides (collectively spacers), and may be nonimmunogenic or immunogenic and capable of inducing a cellular (T cell) or humoral (B cell) immune response in a mammal. Peptides sequence from unrelated microbes may be combined into a single composite antigen. For example, viral sequences of selected immunoresponsive peptides may be interspersed with conserved sequences or epitopes selected from other microbes, such as, for example, bacteria such as *S. pneumococcus, P. auriginosa* or *S. aureus*. Preferred viral proteins, from which preferred epitopes may be selected, include, but are not limited to the influenza virus proteins PspA, PspC, HA, NA, M2e, *H. influenza* protein D, and coagulase.

An epitope of the composite antigen may be of any sequence and size, but is preferable composed of natural amino acids and is more than 5 but less than 35 amino acids in length, preferably less than 30, preferably between 5 and 25 amino acids in length, preferably between 8 and 20 amino acids in length, and more preferably between 5 and 15 amino acids in length.

Composite antigens preferably contain any number of composite and/or other epitopes. The most effective number of epitopes of a composite antigen against a particular pathogen, pathogen family, or group of pathogens may be determined by one skilled in the art from the disclosures of this application and using routine testing procedures. Composite antigens may be effective with one epitope, preferably with 2 or more, 3 or more 4 or more, 5 or more or greater. Optionally, composite antigens may include one or more spacers between epitopes which may be sequences of antigenic regions derived from the same or from one or more different pathogens, or sequences that serve as immunological primers or that otherwise provide a boost to the immune system. That boost may be generated from a sequence of amino acids that are known to stimulate the immune system, either directly or as an adjuvant. In one preferred embodiment, composite antigens useful to generate an immunological response against influenza virus comprise epitopes of HA and/or NA proteins, and/or new epitopes derived from similar conserved regions of different serotypes of influenza virus. Also preferred are composite antigens containing epitopes of proteins of *Mycobacterium tuberculosis* and *Clostridium tetani*, and/or new epitopes derived from similar conserved regions of different serotypes of these bacteria.

Another embodiment of the invention is directed to a contiguous sequence of one or more epitopes, which may comprise composite and/or known epitopes, from one or more pathogens in a sequence that does not exist naturally and must be artificially constructed. Preferably, a contiguous sequence of the invention contains one or more composite epitopes, which is a combination of the sequences of the conserved regions of epitopes that are common to multiple pathogens plus those amino acids that differ between the two conserved regions. For example, where two pathogens contain similar conserved regions that differ by only a single amino acid, the composite sequences would include the conserved region amino acids and each of the amino acids that differ between the two regions as discussed herein.

It is also preferable that a composite antigen of the invention contain a plurality of repeated epitopes and, optionally, epitopes conjugated with linker regions between or surrounding each epitope, and the plurality of epitopes be the same or different. Preferred linkers include amino acid sequences of antigenic regions of the same or of different pathogens, or amino acids sequences that aid in the generation of an immune response. Preferred examples include, but are not limited to any of the various antigenic regions of bacteria such as, but not limited to tuberculosis and virus such as, but not limited to influenza. It is also preferred that composite antigens contain epitopes that generate a T cell response, a B cell response, or both in conjunction with a specific response to the pathogen.

Another embodiment of the invention is directed to immunizing animals with the composite antigens of the invention. Antisera obtained from the immunized animals are reactive against the pathogens from which the composite antigen was derived. Another embodiment of the invention is therefore antisera obtained from the immunized animals, which may be further purified for testing or utilized therapeutically for administration to another mammal and thereby provides protection against infection from the one or more pathogens. It is also preferred that the antisera obtained provide a broad protection, not just against the pathogens from which the composite antigen was derived, but also from additional pathogens that may differ by strain, serotype, or even species.

Another embodiment of the invention is a vaccine composed of the composite antigen or antisera developed from the composite antigen of the invention. Preferably, the vaccines of the invention are less susceptible to variation of antigenicity due to antigenic shift of pathogens which reduces or eliminates the need for annual or repeated vaccination to maintain protection of patient populations against potential outbreaks of infection from new viral isolates. In addition, the vaccines of the invention generally and advantageously provide increased safety considerations, both in their manufacture and administration (due in part to a substantially decreased need for repeated administration), a relatively long shelf life in part due to minimized need to reformulate due to strain-specific shift and drift, an ability to target immune responses with high specificity for particular microbial epitopes, and an ability to prepare a single vaccine that is effective against multiple pathogens, each of which may be a different but know strain or species of the same pathogen. The invention encompasses antigenic and antibody compositions, methods of making such compositions, and methods for their use in the prevention, treatment, management, and/or prophylaxis of an infection. The compositions disclosed herein, as well as methods employing them, find particular use in the treatment or prevention of viral, bacterial, parasitic and/or fungal pathogenesis and infection using immunogenic compositions and methods superior to conventional treatments presently available in the art.

Another embodiment of the invention is directed to methods of preventing or controlling infection, such as, for example, an outbreak of viral, parasitic, fungal or bacterial infection, preferably but not limited to an influenza virus and/or a tuberculosis bacterial infection, in a selected mammalian population. The method includes at least the step of providing an immunologically effective amount of one or more of the disclosed immunogenic or vaccine compositions to a susceptible or an at-risk member of the population, for a time sufficient to prevent, reduce, lessen, alleviate, control, or delay the outbreak of such an infection in the general population.

Another embodiment of the invention is directed to methods for producing a protective immune response against infection, for example by influenza virus, in a mammal in need thereof. Such a method generally includes a step of providing to a mammal in need thereof, an immunologically-effective amount of one or more of the immunogenic compositions disclosed herein under conditions and for a time sufficient to produce such a protective immune response against one or more species, strains, or serotypes of an infectious organism. Additionally, the invention also provides a method for administering a prophylactic antiviral or antimicrobial composition to at least a first cell, tissue, organ, or organ system in a mammal that generally involves providing to such a mammal a prophylactically-effective amount of at least a first immunogenic composition as disclosed herein.

Another embodiment of the invention is directed to an immunogenic composition comprising the composite antigens of the invention having one or more repeated peptide sequences, or fragments, variants, or derivatives of such peptide sequences that are conserved across a plurality of proteins in the same or different pathogen. The conserved regions from which the composite sequence is derived may be conserved within subtypes of the same pathogen or different pathogens. Preferred pathogens include, but are not limited to bacteria, viruses, parasites, fungi and viruses.

Composite antigens of the invention may also be obtained or derived from the sequences of bacteria such as, for example, multiple or combined epitopes of the proteins and/or polypeptides of, for example, but not limited to *Streptococcus, Pseudomonas, Mycobacterium* such as *M. tuberculosis, Shigella, Campylobacter, Salmonella, Haemophilus influenza, Chlamydophila pneumonia, Corynebacterium diphtheriae, Clostridium tetani, Mycoplasma pneumonia, Staphylococcus aureus, Moraxella catarrhalis,*

*Legionella pneumophila, Bordetella pertussis, Escherichia coli*, such as *E. coli* 0157, and multiple or combined epitomes of conserved regions of any of the foregoing. Exemplary parasites from which sequences may be obtained or derived include but are not limited to *Plasmodium* such as *Plasmodium falciparum* and *Trypanosoma*. Exemplary fungi include, but are not limited to *Aspergillus fumigatus* or *Aspergillus flavus*. Exemplary viruses include, but are not limited to arena viruses, bunyaviruses, coronaviruses, filoviruses, hepadna viruses, herpes viruses, orthomyxoviruses, parvoviruses, picornaviruses, papillomaviruses, reoviruses, retroviruses, rhabdoviruses, and togaviruses. Preferably, the virus epitopes are obtained or derived from sequences of Influenza viruses (e.g., the paramyxoviruses).

In another preferred embodiment, the composite antigens contain a conserved region derived from an influenza virus subtypes (e.g., influenza viruses with varying HA or NA compositions, such as H1N1, H5N1, H3N2, and H2N2). Epitopes of conserved regions on NA or HA may also confer cross-subtype immunity. As an example, conserved epitopes on NA(N1) may confer enhanced immunity to H5N1 and H1N1. With respect to similar or homologous chemical compounds among influenza A subtypes and/or strains within a subtype, preferably these are at least about 80 percent, more preferably at least about 90 percent, more preferably at least about 95 percent identical, more preferably at least about 96 percent identical, more preferably at least about 97 percent identical, more preferably at least about 98 percent identical, more preferably at least about 99 percent identical, and even more preferably 100 percent identical (invariant). Preferably, at least one peptide sequence within the composite antigen is also conserved on homologous proteins (e.g., protein subunits) of at least two viral particles, preferably influenza particles. Proteins of influenza virus include, for example, expressed proteins in the virus structure, such as HA, NA, protein polymerases (PB1, PB2, PA), matrix proteins (M1, M2), and nucleoprotein ("NP"). Preferably, the conserved peptide sequences are conserved on at least two or more of the M1, M2, HA, NA, or one or more polymerase proteins.

In a preferred example, a selected sequence in the M1 and M2 proteins of the H5N1 influenza virus corresponds to the M1 and M2 proteins found in other H5N1 particles, and to the same sequence in the M1 and M2 proteins of the H3N2 influenza virus. In addition, while HA and NA proteins have highly variable regions, conserved sequences from HA and NA are found across many influenza strains and many subtypes (e.g., HA and NA sequences are conserved across H5N1 and H1N1). In a preferred embodiment of the invention, the composite sequences is derived from a conserved sequence present within variants or strains (viral isolates expressing substantially the same HA and NA proteins, but wherein the HA and NA protein amino acid sequences show some minor drift), of a single influenzavirus subtype and more preferably across at least two influenzavirus subtypes, e.g., subtypes of influenza A virus.

In another embodiment, the invention provides a composite peptide or polypeptide that includes at least one epitopic antigen, which comprises one or more repeatedly occurring epitope sequences, each of which is conserved across a plurality of homologous proteins that is conserved in a population of influenzavirus strains or serotypes, and a pharmaceutically acceptable carrier. In exemplary composite antigens, at least one epitopic sequence is repeated at least once, preferably at least twice times, more preferably at least three times. In other embodiments, the at least one epitopic sequence is repeated four or more times. Preferably, the composite sequences are identical with the sequences in the homologous protein subunits of at least two circulating viral isolates. In each embodiment, the compositions may include a pharmaceutically acceptable carrier.

In additional preferred embodiments, the composite peptide sequences include sequences derived from genome (i.e., RNA) segment 7 of the influenza virus, while in a more preferred embodiment, the sequences include at least portions of the M1 and M2 proteins. In other preferred embodiments, the composite sequences include sequences expressed from genome segments encoding the HA or NA proteins. Such sequences are less affected by subtype drift and more broadly protective against infections.

In additional embodiments, the composite antigen includes one or more T-cell stimulating epitopes, such as diphtheria toxoid, tetanus toxoid, a polysaccharide, a lipoprotein, or a derivative or any combination thereof (including fragments or variants thereof). Typically, the at least one repeated sequence of the composite antigen is contained within the same molecule as the T-cell stimulating epitopes. In the case of protein-based T-cell stimulating epitopes, the at least one repeated sequence of the composite antigen may be contained within the same polypeptide as the T-cell stimulating epitopes, may be conjugated thereto, or may be associated in other ways. Preferably, at least one repeated sequence is incorporated within or alongside the one or more T-cell stimulating epitopes in a composite antigen of the invention.

In additional embodiments, the composite antigens, with or without associated T-cell stimulating epitopes may include one or more polysaccharides or portions thereof. In preferred embodiments, at least one sequence of a composite antigen is conjugated to one or more polysaccharides. In other embodiments, one or more polysaccharides are conjugated to other portions of the composite antigen. Certain embodiments of the present invention are selected from polysaccharide vaccines, protein-polysaccharide conjugate vaccines, or combinations thereof.

Composite antigens of the invention may be synthesizing by in vitro chemical synthesis, solid-phase protein synthesis, and in vitro (cell-free) protein translation, or recombinantly engineered and expressed in bacterial cells, fungi, insect cells, mammalian cells, virus particles, yeast, and the like.

A preferred composite antigen includes at least one of the following elements: at least one repeated composite sequence; at least one T-cell epitope; at least one polysaccharide; at least one polynucleotide; at least one structural component; or a combination thereof. The at least one structural component may include one or more of: at least one linker segment; at least one sugar-binding moiety; at least one nucleotide-binding moiety; at least one protein-binding moiety; at least one enzymatic moiety; or a combination thereof. The invention encompasses methods of preparing an immunogenic composition, preferably a pharmaceutical composition, more preferably a vaccine, wherein a target antigen of the present invention is associated with a pharmaceutically acceptable diluent, excipient, or carrier, and may be used with most any adjuvant.

Within the context of the present invention, that a relatively small number of conservative or neutral substitutions (e.g., 1 or 2) may be made within the sequence of the composite antigen or epitope sequences disclosed herein, without substantially altering the immunological response to the peptide. In some cases, the substitution of one or more amino acids in a particular peptide may in fact serve to enhance or otherwise improve the ability of the peptide to elicit an immune or T-cell response in an animal that has been provided with a composition that comprises the modified peptide, or a polynucleotide that encodes the peptide. Suitable substitutions may generally be identified using computer programs and the effect of such substitutions may be confirmed based on the reactivity of the modified peptide with antisera and/or T-cells. Accordingly, within certain preferred embodiments, a peptide for use in the disclosed diagnostic and therapeutic methods may comprise a primary amino acid sequence in which one or more amino acid residues are substituted by one or more replacement amino acids, such that the ability of the modified peptide to react with antigen-specific antisera and/or T-cell lines or clones is not significantly less than that for the unmodified peptide.

As described above, preferred peptide variants are those that contain one or more conservative substitutions. A "conservative substitution" is one in which an amino acid is substituted for another amino acid that has similar properties, such that one skilled in the art of peptide chemistry would expect the secondary structure and hydropathic nature of the peptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Examples of amino acid substitutions that represent a conservative change include: (1) replacement of one or more Ala, Pro, Gly, Glu, Asp, Gln, Asn, Ser, or Thr; residues with one or more residues from the same group; (2) replacement of one or more Cys, Ser, Tyr, or Thr residues with one or more residues from the same group; (3) replacement of one or more Val, Ile, Leu, Met, Ala, or Phe residues with one or more residues from the same group; (4) replacement of one or more Lys, Arg, or His residues with one or more residues from the same group; and (5) replacement of one or more Phe, Tyr, Trp, or His residues with one or more residues from the same group. A variant may also, or alternatively, contain non-conservative changes, for example, by substituting one of the amino acid residues from group (1) with an amino acid residue from group (2), group (3), group (4), or group (5). Variants may also (or alternatively) be modified by, for example, the deletion or addition of amino acids that have minimal influence on the immunogenicity, secondary structure and hydropathic nature of the peptide.

Epitopes may be arranged in any order relative to one another in the composite sequence. The number of spacer amino acids between two or more of the epitopic sequences can be of any practical range, including, for example, from 1 or 2 amino acids to 3, 4, 5, 6, 7, 8, 9, or even 10 or more amino acids between adjacent epitopes.

Another embodiment of the invention is directed to polynucleotides including DNA, RNA and PNA constructs that encode the composite sequences of the invention. These polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials. As is appreciated by those of ordinary skill in the art that, as a result of the degeneracy of the genetic code, there are many nucleotide sequences that encode a given primary amino acid sequence. Some of these polynucleotides bear minimal homology to the nucleotide sequence of any native gene. Nonetheless, polynucleotides that vary due to differences in codon usage are specifically contemplated by the present invention. Polynucleotides that encode an immunogenic peptide may generally be used for production of the peptide, in vitro or in vivo. Any polynucleotide may be further modified to increase stability in vivo. Possible modifications include, but are not limited to, the addition of flanking sequences at the 5' and/or 3'-ends; the use of phosphorothioate or 2'-o-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Another embodiment of the invention encompasses methods of vaccinating a subject against Influenza that includes administering to a patient in need of influenza vaccination a therapeutically or prophylactically effective amount of an influenza vaccine, which influenza vaccine includes a composite antigen comprising one or more repeatedly occurring composite or other sequences, each of which is conserved across a plurality of homologous proteins in a plurality of influenza virus particles, and a pharmaceutically acceptable carrier, to provide a detectable immune response in the patient against influenza.

Another embodiment of the invention is directed to nucleotide or DNA vaccines encoding composite antigens of the invention. A DNA vaccine of the invention contains the genetic sequence of a composite antigen, plus other necessary sequences that provide for the expression of the composite antigen in cells. By injecting the mammal with the genetically engineered DNA, the composite antigen is produced in or preferably on cells, which the mammal's immune system recognizes and thereby generates a humoral or cellular response to the composite antigen, and therefore the pathogen. DNA vaccines have a number of advantages over conventional vaccines, including the ability to induce a more general and complete immune response in the mammal. Accordingly, DNA vaccines can be used to protect a mammal against disease caused from many different pathogenic organisms of viral, bacterial, and parasitic origin as well as certain tumors.

DNA vaccines typically comprise a bacterial DNA contained that encodes the composite antigen contained in vectors or plasmids that have been genetically modified to transcribe and translate the composite antigenic sequences into specific protein sequences derived from a pathogen. By way of example, the vaccine DNA is injected into the cells of the body, where the cellular machinery transcribed and translates the DNA into the composite antigen. Composite antigens, being non-natural and unrecognized by the mammalian immune system, are processed by cells and the processed proteins, preferably the epitopes, displayed on cell surfaces. Upon recognition of these composite antigens as foreign, the mammal's immune system generates an appropriate immune response that protects the mammal from infection. In addition, DNA vaccine of the invention are preferably codon optimized for expression in the mammalian cells of interest, such as but not limited to mouse or human cells. In a preferred embodiment, codon optimization involves selecting a desired codon usage bias (the frequency of occurrence of synonymous codons in coding DNA) for the particular cell type so that the desired peptide sequence is expressed.

Another embodiment of the invention is directed to therapeutic and prophylactic agents in a pharmaceutically acceptable composition for administration to a cell or an animal, either alone, or in combination with one or more other modalities of prophylaxis and/or therapy. Therapeutic and prophylactic agents of the invention include composite antigens, composite epitopes, compositions containing composite antigens and epitopes, composite sequences, DNA vaccines of the invention, antibodies of the invention, and/or T cells primed or exposed to composite antigens of the invention. The formulation of pharmaceutically-acceptable excipients and carrier solutions is well known to those of ordinary skill in the art, as is the development of suitable dosing and treatment regimens for using the particular compositions described herein in a variety of treatment regimens.

The amount of immunogenic composition(s) and the time needed for the administration of such immunogenic composition(s) will be within the purview of the ordinary-skilled artisan having benefit of the present teachings. The administration of a therapeutically-effective, pharmaceutically-effective, and/or prophylactically-effective amount of the disclosed immunogenic compositions may be achieved by a single administration, such as for example, a single injection of a sufficient quantity of the delivered agent to provide the desired benefit to the patient undergoing such a procedure. Alternatively, in some circumstances, it may be desirable to provide multiple, or successive administrations of the immunogenic compositions, either over a relatively short, or even a relatively prolonged period of time, as may be determined by the medical practitioner overseeing the administration of such compositions to the selected individual.

The immunogenic compositions and vaccines of the present invention are preferably administered in a manner compatible with the dosage formulation, and in such an amount as will be prophylactically or therapeutically effective and preferably immunogenic. The quantity to be administered depends on the subject to be treated, including, e.g., the capacity of the patient's immune system to mount an immune response, and the degree of protection desired. Suitable dosage ranges may be on the order of several hundred micrograms (μg) of active ingredient per vaccination with a preferred range from about 0.1 μg to 2000 μg (even though higher amounts, such as, e.g., in the range of about 1 to about 10 mg are also contemplated), such as in the range from about 0.5 μg to 1000 μg, preferably in the range from about 1 μg to about 500 μg and especially in the range from about 10 μg to about 100 μg. Suitable regimens for initial administration and booster shots are also variable but are typified by an initial administration followed by optional but preferred subsequent inoculations or other periodic administrations.

In certain embodiments, the dose would consist of the range of about 1 μg to about 1 mg total protein or target antigen. In one exemplary embodiment, the vaccine dosage range is about 0.1 μg to about 10 mg. However, one may prefer to adjust dosage based on the amount of peptide delivered. In either case, these ranges are merely guidelines from which one of ordinary skill in the art may deviate according to conventional dosing techniques. Precise dosages may be determined by assessing the immunogenicity of the conjugate produced in the appropriate host so that an immunologically effective dose is delivered. An immunologically effective dose is one that stimulates the immune system of the patient to establish an immune response to the immunogenic composition or vaccine. Preferably, a level of immunological memory sufficient to provide long-term protection against disease caused by microbial infection is obtained. The immunogenic compositions or vaccines of the invention may be preferably formulated with an adjuvant. By "long-term" it is preferably meant over a period of time of at least about 6 months, over at least about 1 year, over at least about 2 to 5 or even at least about 2 to about 10 years or longer.

Another embodiment of the invention is directed to antibodies that are specific for the composite antigens as described here and conservative variants thereof. Antibodies specific for these polypeptides are useful, e.g., in both diagnostic and therapeutic purposes, e.g., related to the activity, distribution, and expression of target polypeptides. Antibodies of the invention may be classes IgG, IgM, IgA, IgD or IgE and include, but are not limited to, polyclonal antibodies, monoclonal antibodies, multiple or single chain antibodies, including single chain Fv (sFv or scFv) antibodies in which a variable heavy and a variable light chain are joined together (directly or through a peptide linker) to form a continuous polypeptide, and humanized or chimeric antibodies.

Antibodies specific for the composite peptides of the invention can be generated by methods well known in the art. Such antibodies can include, but are not limited to, polyclonal, monoclonal, chimeric, humanized, single chain, Fab fragments and fragments produced by an Fab expression library. Numerous methods for producing polyclonal and monoclonal antibodies are known to those of skill in the art, and can be adapted to produce antibodies specific for the polypeptides of the invention, and/or encoded by the polynucleotide sequences of the invention (see, e.g., Coligan Current Protocols in Immunology Wiley/Greene, NY; Paul (ed.) (1991); (1998) Fundamental Immunology Fourth Edition, Lippincott-Raven, Lippincott Williams & Wilkins; Harlow and Lane (1989) Antibodies: A Laboratory Manual, Cold Spring Harbor Press, NY, USA; Stites et al. (Eds.) Basic and Clinical Immunology (4th ed.) Lange Medical Publications, Los Altos, Calif., USA and references cited therein; Goding, Monoclonal Antibodies: Principles and Practice (2d ed.) Academic Press, New York, N.Y., USA; 1986; and Kohler and Milstein (1975).

The following examples illustrate embodiments of the invention, but should not be viewed as limiting the scope of the invention.

EXAMPLES

Sequences

The following is a list of exemplary sequence. These sequences include composite sequences as well as sequences of interest that can be combined to form composite sequences of the invention:

| | | |
|---|---|---|
| SEQ ID NO 1 | DWSGYSGSFVQHPELTGLD (N1 sequence; H1 N5 |
| SEQ ID NO 2 | ETPIRNE (N1 epitope) |
| SEQ ID NO 3 | FVIREPFISCSHLEC (Pep 5) |
| SEQ ID NO 4 | GNFIAP (HA epitope; Pep 1) |
| SEQ ID NO 5 | GNLIAP (HA epitope; Pep 2) |
| SEQ ID NO 6 | GNLFIAP (composite sequence of SEQ ID NOs

| SEQ ID NO | Sequence |
|---|---|
| SEQ ID NO 7 | GNLIFAP (composite sequence of SEQ ID NOs 4 and 5) |
| SEQ ID NO 8 | HYEECSCY (NA epitope; Pep 10) |
| SEQ ID NO 9 | LLTEVETPIR |
| SEQ ID NO 10 | LLTEVETPIRN |
| SEQ ID NO 11 | LLTEVETPIRNE |
| SEQ ID NO 12 | DWSGYSGSFVQHPELTGL (N4 sequence; H1 N5) |
| SEQ ID NO 13 | EVETPIRNE |
| SEQ ID NO 14 | FLLPEDETPIRNEWGLLTDDETPIRYIKANSKFIGITE |
| SEQ ID NO 15 | GNLFIAPGNLFIAPHYEECSCYHYEECSCYQYIKANSKFIGITEHYEECSCYTPIRNETPIRNE |
| SEQ ID NO 16 | GNLFIAPGNLFIAPQYIKANSKFIGITEGNLFIAP (composite of SEQ ID NO 6, SEQ ID NO 6, SEQ ID NO 60, and SEQ ID NO 6) |
| SEQ ID NO 17 | HYEECSCYDWSGYSGSFVQHPELTGLHYEECSCYQYIKANSKFIGITE |
| SEQ ID NO 18 | ITGFAPFSKDNSIRLSAGGDIWVTREPYVSCDP |
| SEQ ID NO 19 | IWGIHHP (HA epitope) |
| SEQ ID NO 20 | IWGVHHP (HA epitope) |
| SEQ ID NO 21 | IWGVIHHP (composite of SEQ ID NOs. 19 and 20) |
| SEQ ID NO 22 | IWGIVHHP (composite of SEQ ID NOs. 19 and 20) |
| SEQ ID NO 23 | KSCINTRCFYVELIRGR |
| SEQ ID NO 24 | LLTEVETPIRNESLLTEVETPIRNEWG (M2e epitope) |
| SEQ ID NO 25 | LLTEVETPIRNEW (M2e epitope) |
| SEQ ID NO 26 | LLTEVETPIRNEWG (M2e epitope) |
| SEQ ID NO 27 | LTEVETPIRNE (M2e epitope) |
| SEQ ID NO 28 | LTEVETPIRNEW (M2e epitope) |
| SEQ ID NO 29 | LTEVETPIRNEWG (M2e epitope) |
| SEQ ID NO 30 | MSLLTEVET (M2e epitope) |
| SEQ ID NO 31 | MSLLTEVETP (M2e epitope) |
| SEQ ID NO 32 | MSLLTEVETPI (M2e epitope) |
| SEQ ID NO 33 | MSLLTEVETPIR (M2e epitope) |
| SEQ ID NO 34 | MSLLTEVETPIRN (M2e epitope) |
| SEQ ID NO 35 | MSLLTEVETPIRNE (M2e epitopes) |
| SEQ ID NO 36 | MSLLTEVETPIRNETPIRNE (M2e epitope) |
| SEQ ID NO 37 | MSLLTEVETPIRNEW (M2e epitope) |
| SEQ ID NO 38 | MSLLTEVETPIRNEWG (M2e epitope) |
| SEQ ID NO 39 | MSLLTEVETPIRNEWGCRCNDSSD (M2e epitope) |
| SEQ ID NO 40 | SLLTEVET (M2e epitope) |
| SEQ ID NO 41 | SLLTEVETPIRNE (M2e epitope) |
| SEQ ID NO 42 | SLLTEVETPIRNEW (M2e epitope) |
| SEQ ID NO 43 | SLLTEVETPIRNEWG (M2e epitope) |
| SEQ ID NO 44 | SLLTEVETPIRNEWGTPIRNE (M2e epitope) |
| SEQ ID NO 45 | SLLTEVETPIRNEWGTPIRNETPIRNE (M2e epitope) |
| SEQ ID NO 46 | SLLTEVETPIRNEWGTPIRNETPIRNETPIRNE (M2e epitopes) |
| SEQ ID NO 47 | SLLTEVETPIRNEWGLLTEVETPIRQYIKANSKFIGITE (M2e epitope) |
| SEQ ID NO 48 | TEVETPIRNE (M2e epitope) |
| SEQ ID NO 49 | TPIRNE |
| SEQ ID NO 50 | VETPIRNE |
| SEQ ID NO 51 | VTREPYVSCDPKSCINRCFYVELIRGRVTREPYVSCDPWYIKANSKFIGITE |
| SEQ ID NO 52 | WGIHHP (HA conserved region; Pep 5) |
| SEQ ID NO 53 | WGVHHP (HA conserved region; Pep 4) |
| SEQ ID NO 54 | WGVIHHP (composite of SEQ ID NOs 52 and 53; Pep 6) |
| SEQ ID NO 55 | WGIVHHP (composite of SEQ ID NOs 52 and 53; Pep 7) |
| SEQ ID NO 56 | YIWGIHHP |
| SEQ ID NO 57 | YIWGVHHP |
| SEQ ID NO 58 | YIWGVIHHP (composite of SEQ ID NOs 56 and 57) |
| SEQ ID NO 59 | YIWGIVHHP (composite of SEQ ID NOs 56 and 57) |
| SEQ ID NO 60 | QYIKANSKFIGITE |
| SEQ ID NO 61 | PIRNEWGCRCNDSSD |
| SEQ ID NO 65 | SEYAYGSFVRTVSLPVGADEGNLFIAPWGVIHHPHYEECSCYGLPVEYLQVPSPSMGRDIKVQFQSGGANSPALYLLDGLRAQDDFSGWDINTPAFEWYDQSGLSVVMPVGGQSSFYSDWYQPACRKAGCQTYKWETFLTSELPGWLQANRHVQPTGSAVVGLSMAASSALTLAIYHPQQFVYAGAMSGLLDPSQAMGPTLIGLAMGDAGGYKASDMWGPKEDPAWQRNDPLLNVGKLIANNTRVWVYCGNGKPSDLGGNNLPAKFLEGFVRTSNIKFQDAYNAGGHNGVFDFPDSGTHSWEYWGAQLNAMKPDLQRHWVPRPTPGPPQGAFDFPDSGTHSWEYWGAQLNAMKPDLQRHWVPRPTPGPPQGA (Sequence for DNA vaccine development 373 amino acids; has a TB conserved regions on each side of Pep 11) |
| SEQ ID NO 66 | GNLFIAPWGVIHHPHYEECSCY (SEQ ID NOs 6, 54, and 8; Pep 11) |
| SEQ ID NO 67 | WGVIHHPGNLFIAPHYEECSCY (SEQ ID NOs 54, 6, and 8) |
| SEQ ID NO 68 | SRPGLPVEYLQVPSPSMGRDIKVQFQSGGANSPALYLLDGLRAQDDFSGWDINTPAFEWYDQSGLSVVMPVGGQSSFYSDWYQPACGKAGCQTYKWETFLTSELPGWLQANRHVKPTGSAVVGLSMAASSALTLAIYHPQQFVYAGAMSGLLDPSQAMGPTLIGLAMGDAGGYKASDMWGPKEDPAWQRNDPLLNVGKLIANNTRVWVYCGNGKPSDLGGNNLPAKFLEGFVRTSNIKFQDAYNA |

-continued

GGGHNGVFDFPDSGTHSWEYWGAQLNAMKPDLQRA
LGATPNTGPAPQGA (TB coding region
sequence of 85a)

SEQ ID NO 69
TCCCGGCCGGGCTTGCCGGTGGAGTACCTGCAGGT
GCCGTCGCCGTCGATGGGCCGTGACATCAAGGTCC
AATTCCAAAGTGGTGGTGCCAACTCGCCCGCCCTG
TACCTGCTCGACGGCCTGCGCGCGCAGGACGACTT
CAGCGGCTGGGACATCAACACCCCGGCGTTCGAGT
GGTACGACCAGTCGGGCCTGTCGGTGGTCATGCCG
GTGGGTGGCCAGTCAAGCTTCTACTCCGACTGGTA
CCAGCCCGCCTGCGGCAAGGCCGGTTGCCAGACTT
ACAAGTGGGAGACCTTCCTGACCAGCGAGCTGCCG
GGGTGGCTGCAGGCCAACAGGCACGTCAAGCCCAC
CGGAAGCGCCGTCGTCGGTCTTTCGATGGCTGCTT
CTTCGGCGCTGACGCTGGCGATCTATCACCCCCAG
CAGTTCGTCTACGCGGGAGCGATGTCGGGCCTGTT
GGACCCCTCCCAGGCGATGGGTCCCACCCTGATCG
GCCTGGCGATGGGTGACGCTGGCGGCTACAAGGCC
TCCGACATGTGGGGCCCGAAGGAGGACCCGGCGTG
GCAGCGCAACGACCCGCTGTTGAACGTCGGGAAGC
TGATCGCCAACAACACCCGCGTCTGGGTGTACTGC
GGCAACGGCAAGCCGTCGGATCTGGGTGGCAACAA
CCTGCCGGCCAAGTTCCTCGAGGGCTTCGTGCGGA
CCAGCAACATCAAGTTCCAAGACGCCTACAACGCC
GGTGGCGGCCACAACGGCGTGTTCGACTTCCCGGA
CAGCGGTACGCACAGCTGGGAGTACTGGGGCGCGC
AGCTCAACGCTATGAAGCCCGACCTGCAACGGGCA
CTGGGTGCCACGCCCAACACCGGGCCCGCGCCCCA
GGGCGCC
(nucleotide sequence corresponding
to TB sequence 85a or SEQ ID NO 64)

SEQ ID NO 70
SEFAYGSFVRTVSLPVGADEGNLFIAPWGVIHHPH
YEECSCYSRPGLPVEYLQVPSPSMGRDIKVQFQSG
GANSPALYLLDGLRAQDDFSGWDINTTPAFEWYDQ
SGLSVVMPVGGQSSFYSDWYQPACGKAGCQTYKWE
TFLTSELPGWLQANRHVKPTGSAVVGLSMAASSAL
TLAIYHPQQFVYAGAMSGLLDPSQAMGPTLIGLAM
GDAGGYKASDMWGPKEDPAWQRNDPLLNVGKLIAN
NTRVWVYCGNGKPSDLGGNNLPAKFLEGFVRTSNI
KFQDAYNAGGGHNGVFDFPDSGTHSWEYWGAQLNA
MKPDLQRALGATPNTGPAPQGA (336 amino
acid sequence comprising HSPx, Pep
11 and TB 85a)

SEQ ID NO 71
TTTGGGCCCATTATGTCGGAATTCGCGTACGGTTC
CTTCGTTCGCACGGTGTCGCTGCCGGTAGGTGCTG
ACGAG**GGGAATCTAttcATTGCTCCTTGGGGGGTT
attCACCACCCGCATTATGAGGAATGTTCCTGTTA
C**TCCCGGCCGGGCTTGCCGGTGGAGTACCTGCAGG
TGCCGTCGCCGTCGATGGGCCGTGACATCAAGGTC
CAATTCCAAAGTGGTGGTGCCAACTCGCCCGCCCT
GTACCTGCTCGACGGCCTGCGCGCGCAGGACGACT
TCAGCGGCTGGGACATCAACACCCCGGCGTTCGAG
TGGTACGACCAGTCGGGCCTGTCGGTGGTCATGCC
GGTGGGTGGCCAGTCAAGCTTCTACTCCGACTGGT
ACCAGCCCGCCTGCGGCAAGGCCGGTTGCCAGACT
TACAAGTGGGAGACCTTCCTGACCAGCGAGCTGCC
GGGGTGGCTGCAGGCCAACAGGCACGTCAAGCCCA
CCGGAAGCGCCGTCGTCGGTCTTTCGATGGCTGCT
TCTTCGGCGCTGACGCTGGCGATCTATCACCCCCA
GCAGTTCGTCTACGCGGGAGCGATGTCGGGCCTGT
TGGACCCCTCCCAGGCGATGGGTCCCACCCTGATC
GGCCTGGCGATGGGTGACGCTGGCGGCTACAAGGC
CTCCGACATGTGGGGCCCGAAGGAGGACCCGGCGT
GGCAGCGCAACGACCCGCTGTTGAACGTCGGGAAG
CTGATCGCCAACAACACCCGCGTCTGGGTGTACTG
CGGCAACGGCAAGCCGTCGGATCTGGGTGGCAACA
ACCTGCCGGCCAAGTTCCTCGAGGGCTTCGTGCGG
ACCAGCAACATCAAGTTCCAAGACGCCTACAACGC
CGGTGGCGGCCACAACGGCGTGTTCGACTTCCCGG
ACAGCGGTACGCACAGCTGGGAGTACTGGGGCGCG
CAGCTCAACGCTATGAAGCCCGACCTGCAACGGGC
ACTGGGTGCCACGCCCAACACCGGGCCCGCGCCCC
AGGGCGCCTAGTTTCTTAAGTTT Underlined sequences:
Start and stop codons
Afl II Restriction Site (NEB Buffer 4)
Note:
multi T Spacer between stop and Afl II RE
Apa I Restriction Site (NEB Buffer 4)
Note:
Spacer between start and Apa I RE is Kozak
minimal translation initiation site Bold sequences:
HA1 sequence bolded and underlined
(SEQ ID NO 72)
HA2 sequence bolded (SEQ ID NO 73
NA1 sequence bolded and underlined
(SEQ ID NO 74)

SEQ ID NO 72 GGGAATCTAttcATTGCTCCT

SEQ ID NO 73 TGGGGGGTTattCACCACCCG

SEQ ID NO 74 CATTATGAGGAATGTTCCTGTTAC

SEQ ID NO 75 SEFAYGSFVRTVSLPVGADE
(Heat Shock protein sequence of
epitope HSPx derived from
*Mycobacterium tuberculosis* H37Rv
(NC_000962.2)

SEQ ID NO 76
TCGGAATTCGCGTACGGTTCCTTCGTTCGCACGGT
GTCGCTGCCGGTAGGTGCTGACGAG
(nucleotide sequence corresponding
to HSPx; SEQ ID NO 66)

SEQ ID NO 77 GNLFIAPWGVIHHPHYEECSCY (underlined
sequences are epitopes HA
{composite} and NA, respectively,
of Influenza A; Pep 11)

SEQ ID NO 78
GGGAATCTAttcATTGCTCCTTGGGGGGTTattCA
CCACCCGCATTATGAGGAATGTTCCTGTTAC
(Pep 11- SEQ ID NO 68)

SEQ ID NO 79
TCGGAATTCGCGTACGGTTCCTTCGTTCGCACGGT
GTCGCTGCCGGTAGGTGCTGACGAGGGGAATCTAt
tcATTGCTCCTTGGGGGGTTattCACCACCCGCAT
TATGAGGAATGTTCCTGTTACTCCCGGCCGGGCTT
GCCGGTGGAGTACCTGCAGGTGCCGTCGCCGTCGA
TGGGCCGTGACATCAAGGTCCAATTCCAAAGTGGT
GGTGCCAACTCGCCCGCCCTGTACCTGCTCGACGG
CCTGCGCGCGCAGGACGACTTCAGCGGCTGGGACA
TCAACACCCCGGCGTTCGAGTGGTACGACCAGTCG
GGCCTGTCGGTGGTCATGCCGGTGGGTGGCCAGTC
AAGCTTCTACTCCGACTGGTACCAGCCCGCCTGCG
GCAAGGCCGGTTGCCAGACTTACAAGTGGGAGACC
TTCCTGACCAGCGAGCTGCCGGGGTGGCTGCAGGC
CAACAGGCACGTCAAGCCCACCGGAAGCGCCGTCG
TCGGTCTTTCGATGGCTGCTTCTTCGGCGCTGACG
CTGGCGATCTATCACCCCCAGCAGTTCGTCTACGC
GGGAGCGATGTCGGGCCTGTTGGACCCCTCCCAGG
CGATGGGTCCCACCCTGATCGGCCTGGCGATGGGT
GACGCTGGCGGCTACAAGGCCTCCGACATGTGGGG
CCCGAAGGAGGACCCGGCGTGGCAGCGCAACGACC
CGCTGTTGAACGTCGGGAAGCTGATCGCCAACAAC
ACCCGCGTCTGGGTGTACTGCGGCAACGGCAAGCC
GTCGGATCTGGGTGGCAACAACCTGCCGGCCAAGT
TCCTCGAGGGCTTCGTGCGGACCAGCAACATCAAG
TTCCAAGACGCCTACAACGCCGGTGGCGGCCACAA
CGGCGTGTTCGACTTCCCGGACAGCGGTACGCACA
GCTGGGAGTACTGGGGCGCGCAGCTCAACGCTATG
AAGCCCGACCTGCAACGGGCACTGGGTGCCACGCC
CAACACCGGGCCCGCGCCCCAGGGCGCC (1008
nucleotide DNA construct of
composite peptide comprising TB
epitopes at each end with an
influenza sequence in the middle -continued

| | |
|---|---|
| | which is composed of three epitopes- 2 HA composites {underlined} with an NA epitope between them). |
| SEQ ID NO 80 | CAGAGNFIAP |
| SEQ ID NO 81 | CAGAGNLIAP |
| SEQ ID NO 82 | CAGAGNLFIAP |
| SEQ ID NO 83 | CAGAWGVHHP |
| SEQ ID NO 84 | CAGAWGIHHP |
| SEQ ID NO 85 | CAGAWGVIHHP |
| SEQ ID NO 86 | CAGAWGIVHHP |
| SEQ ID NO 87 | GNLIAPWGVIHHP |
| SEQ ID NO 88 | CAGAGNLIAPWGVIHHP |
| SEQ ID NO 89 | GNLFIAPWGVIHHP |
| SEQ ID NO 90 | CAGAGNLFIAPWGVIHHP |
| SEQ ID NO 91 | HYEECSCY |
| SEQ ID NO 92 | CAGAHYEECSCY |
| SEQ ID NO 93 | GNLFIAPWGVIHHPHYEECSCY |
| SEQ ID NO 94 | CAGAGNLFIAPWGVIHHPHYEECSCY |
| SEQ ID NO 95 | GNLFIAPWGVIHHPGNLFIAPWGVIHHP |
| SEQ ID NO 96 | CAGAGNLFIAPWGVIHHPGNLFIAPWGVIHHP |
| SEQ ID NO 97 | HYEECSCYGNLFIAPWGVIHHP |
| SEQ ID NO 98 | GNLFIAPHYEECSCYWGVIHHP |
| SEQ ID NO 99 | SLLTEVETPIRNEWGLLTEVETPIRQYIKANSKFI GITE |
| SEQ ID NO 100 | GNLFIAPGNLFIAPQYIKANSKFIGITEGNLFIAP |
| SEQ ID NO 101 | HYEECSCYDWSGYSGSFVQHPELTGLHYEECSCYQ YIKANSKFIGITE |
| SEQ ID NO 102 | VTREPYVSCDPKSCINRCFYVELIRGRVTREPYVS CDPQYIKANSKFIGITE |
| SEQ ID NO 103 | DWSGYSGSFVQHPELTGL |
| SEQ ID NO 104 | ITGFAPFSKDNSIRLSAGGDIWVTREPYVSCDP |
| SEQ ID NO 105 | KSCINRCFYVELIRGR |
| SEQ ID NO 106 | GNLFIAPRYAFA |
| SEQ ID NO 107 | CAGAGNLFIAPRYAFA |
| SEQ ID NO 108 | GNLVVPRYAFA |
| SEQ ID NO 109 | CAGAGNLVVPRYAFA |
| SEQ ID NO 110 | GNLIAPRYAFA |
| SEQ ID NO 111 | CAGAGNLIAPRYAFA |
| SEQ ID NO 112 | GNLVVP |
| SEQ ID NO 113 | CAGAGNLVVP |
| SEQ ID NO 114 | FVIREPFISCSHLEC |

-continued

| | |
|---|---|
| SEQ ID NO 115 | CAGAFVIREPFISCSHLEC |
| SEQ ID NO 116 | CAGA |

FIG. 1 shows titers as determined by ELISA of mice vaccinated with Pep 6, Pep 9, Pep 10 or Pep 11. As can be seen, vaccinations with Pep 9, Pep 10 and Pep 11 provided a generally strong repose to the native antigen and the highest titers in mice.

FIG. 2 shows mean OD values of sera from mice immunized peptides derived from the Wuhan strain of Influenza (H3N2). Results indicate that Pep 10 and Pep 11 provide a significant immune response as compared to unvaccinated mice (the Balb/c pool) and mice vaccinated with Pep 3.

FIG. 3 shows mean OD values of antisera (titered at 1:100) following immunization with Pep 6. As can be seen, Pep 6 the antisera reacted strongly with viruses of both H1N1 and H3N2.

FIG. 4 shows antisera titers of mice immunized with Pep 9 as reacted with Influenza strain Caledonia virus (H1N1) at various dilutions. As seen, Pep 9 reacts strongly with whole virus.

FIG. 5 shows four graphs (A-D), each depicting the absorbance of Pep 9 sera to one of four substrates: (A) fresh Wuhan virus; (B) fixed Wuhan virus; (C) fresh Caledonia virus; and (D) fixed Caledonia virus. As shown, Pep 9 sera reacting strongly in with all substrates tested.

FIG. 6 shows the titers from mice immunized with Pep 9 as captured with substrates of fresh or fixed Wuhan or Caledonia virus substrates. Again, Pep 9 antisera were strongly reactive with each and the amount of binding observed for many of the antisera tested was similar between fresh and fixed.

FIG. 7 shows antisera titers of mice immunized with Pep 11 as captured with various dilutions of substrates of H5N1. As can be seen, binding was observed with both sera tested.

A composite antigen that contains previously determined conserved surface protein epitopes of hemagglutinin and neuraminidase from Influenza A viruses (several subtypes including human H1, H3 and high-path H5) was constructed. Also included were proteins segments from HspX and 85a from *Mycobacterium tuberculosis*. The expressed protein hybrid construct included the following: NH2+----HspX-HA1-HA2-NA1-85a----COO— wherein, HspX is 20 amino acids from *Mycobacterium tuberculosis* HspX protein; HA1 is a 7 amino acid highly conserved hybrid region influenza A hemagglutinin protein; HA2 is a 7 amino acid highly conserved hybrid region of influenza A hemagglutinin protein; NA1 is an 8 amino acid highly conserve hybrid region of influenza A neuraminidase protein; and 85a is 294 amino acids from the 85 kD 85a protein of *Mycobacterium tuberculosis*. The mature corresponding protein sequence is the 336 amino acid sequence of SEQ ID NO 70.

The composite antigen vaccine is constructed using the pVAX1 (Invitrogen Inc, Cat # V260-20) by recombinant methods. Briefly, a single stranded (ss) DNA polymer corresponding to SEQ ID 70 is synthesized. The ssDNA sequence also include: 1) a 5' ApaI restriction endonuclease recognition site and a 3' Afl II restriction site for directional insertion into pVAX1 cloning vector, 2) a ATT minimal Kozak translation initiation sequence at the 5' end, 3) a ATG start codon, and 4) a 3' TAG termination (stop) codon. The nucleotide sequence in its entirety will consist of 1038 nucleotides which is SEQ ID NO 71.

This single stranded nucleotide sequence is used as a template to generate double stranded amplicon by polymerase chain reaction. Following PCR amplification the amplicon is subjected to restriction endonuclease digestion, ligated into pVAX1 and transformed into *E. Coli* bacteria using standard transformation and screening methods with Kanamycin selection. Plasmids containing recombinant insert are grown in overnight culture and purified using known plasmid extraction methods. Concentrations of recombinant pVAX1 plasmid are subjected to DNA sequencing and utilized in downstream transfection experiments in mice.

Figure 6:
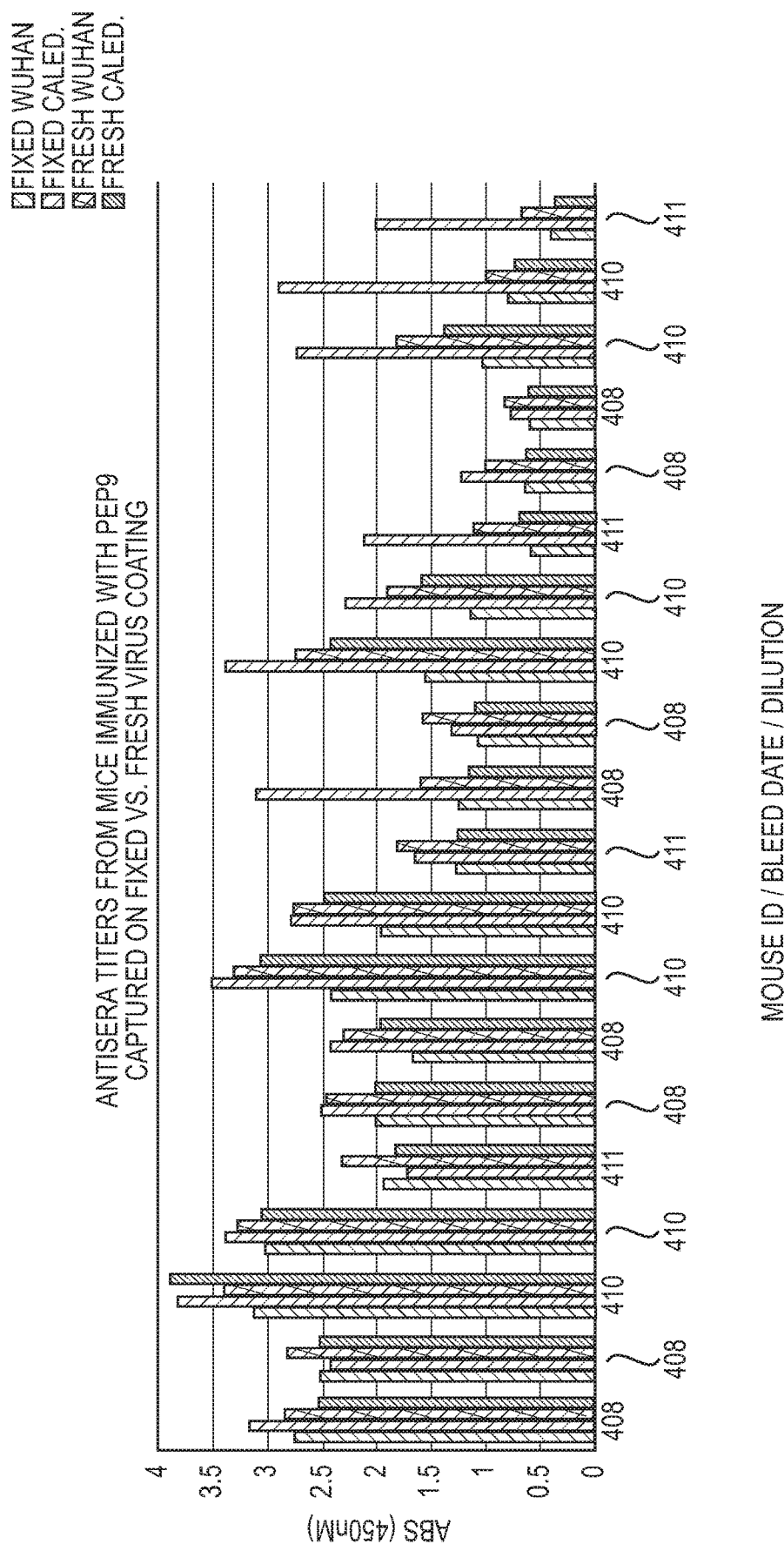
FIG. 6 Antisera titers from mice immunized with Pep 9 captured on fixed vs. Fresh coatings of Wuhan and Caledonia.

FIGS. 8-1 to 8-6 list a large number of sequences that include conserved or otherwise targeted regions of various genetic sequence of interest, and composite sequences of the invention.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A method of treating, preventing, or inhibiting symptoms of an influenza virus infection comprising:
providing an immunogenic preparation that contains at least two peptides, wherein at least one of the two peptides comprises an amino acid sequence that is at least 95% identical to any one of SEQ ID NOs: 6, 14-17, 47, and 54-55; and at least one of the two peptides comprises a T-cell stimulating epitope; and
administering the immunogenic preparation to a patient to generate an immunological response to the infection.

2. The method of claim 1, wherein the influenza virus comprises one or more of H1N1, H1N7, H2N2, H3N1, H3N2, H3N8, H5N1, H5N2, H5N3, H5N8, H5N9, H7N1, H7N2, H7N3, H7N4, H7N7 or H9N2.

3. The method of claim 1, wherein at least one peptide comprises the sequence of SEQ ID NO 6.

4. The method of claim 1, wherein at least one peptide comprises the sequence of SEQ ID NO 14.

5. The method of claim 1, wherein at least one peptide comprises the sequence of SEQ ID NO 15.

6. The method of claim 1, wherein at least one peptide comprises the sequence of SEQ ID NO 16.

7. The method of claim 1, wherein at least one peptide comprises the sequence of SEQ ID NO 17.

8. The method of claim 1, wherein at least one peptide comprises the sequence of SEQ ID NO 54.

9. The method of claim 1, wherein at least one peptide comprises the sequence of SEQ ID NO 55.

10. The method of claim 1, wherein each of the at least two peptides comprises an amino acid sequence that is at least 95% identical to any one of SEQ ID NOs: 6, 14-17, 47, and 54-55.

11. The method of claim 1, wherein the T-cell stimulating epitope comprises a fragment, derivative, or variant of CRM, diphtheria toxoid, tetanus toxoid, lipoprotein, or combinations thereof.

12. The method of claim 1, wherein the at least two peptides and the T-cell stimulating epitope are conjugated.

13. The method of claim 1, wherein the immune response comprises a cellular or antibody-mediated immune response against the infection.

14. The method of claim 13, wherein the cellular or antibody-mediated immune response comprises one or more of production of antibodies, B cells, T Helper cell, or cytotoxic T cells directed against the infection.

15. The method of claim 1, wherein the immunogenic preparation comprises an adjuvant.

16. The method of claim 1, wherein the immunogenic preparation does not include an adjuvant.

17. The method of claim 1, wherein the immunogenic preparation is formulated for local or system administration.

18. The method of claim 1, wherein the immunogenic preparation is formulated as microcapsules, microparticles, microspheres, nanocapsules, nanoparticles, nanospheres, or combinations thereof.

19. The method of claim 1, wherein administering comprises a single dose of the immunogenic preparation.

20. The method of claim 1, wherein administering comprises multiple doses of the immunogenic preparation.

21. The method of claim 1, wherein administration is intradermal, intramuscular, intranasal, intravenous, oral, parenteral, subcutaneous, transcutaneous, or transdermal.

22. The method of claim 1, wherein administration is a prophylactically or therapeutically effective amount.

23. A method of treating, preventing, or inhibiting symptoms of an influenza virus infection comprising:
providing an immunogenic preparation that contains at least two peptides, wherein at least one of the two peptides comprises an amino acid sequence that is at least 95% identical to any one of SEQ ID NOs: 6, 14-17, 47, and 54-55; and at least one of the two peptides comprises a T-cell stimulating epitope;
administering the immunogenic preparation to a mammal to generate an immunological response containing antibodies responsive to the immunogenic preparation; and
collecting antibodies generated.

24. The method of claim 23, further comprising administering the antibodies collected to a patient suspected of having or actually having an influenza virus infection.

25. A method of treating, preventing or inhibiting symptoms of an influenza virus infection, comprising:
providing an immunogenic preparation that contains a composite antigen, wherein said composite antigen comprises a sequence derived from two different antigenic epitopes,
wherein the two different antigenic epitopes comprise similar sequences at the N- and C-terminal portions and a different amino acid sequences in the middle portion, and wherein said two different epitopes are derived from the one or more pathogens,
wherein said composite antigen comprises the formula A1BCA2, wherein:
1) A1 is the consensus sequence between the two epitopes that are the common amino acids at the N-terminus of each epitope, and wherein A1 is less than 30 amino acids;
2) B represents the one or two middle amino acid residue(s) from the first epitope that differ from the second epitope;
3) C represents the one or two middle amino acid residue(s) from the second epitope that differ from the first epitope;
4) A2 is the consensus sequence between the two epitopes that are the common amino acids at the C-terminus of each epitope, and wherein A2 is less than 30 amino acids;
administering the immunogenic preparation to a patient to generate an immunological response to the infection.

26. The method of claim 25, wherein said antigen is linked to one or more additional epitopes, one or more additional composite epitopes, or a combination thereof.

27. The method of claim 25, wherein the antigenic epitopes are derived from M1, M2, HA, NA, PB1, or PB2 proteins of Influenza virus, or a combination thereof.

28. The method of claim 25, wherein the two different antigenic epitopes comprise SEQ ID NOs 4 and 5, or SEQ ID NOs 80 and 81, or SEQ ID NOs 83 and 84.

29. The method of claim 25, wherein the composite antigenic sequence comprises SEQ ID NOs: 6, 21, 22, 54, 55, 58, 59, 82, 85, or 86.

30. The method of claim 25, wherein the different epitopes of the immunogenic composition are derived from different serotypes of influenza virus.

* * * * *